United States Patent
Bjartmar et al.

(10) Patent No.: US 11,510,944 B2
(45) Date of Patent: *Nov. 29, 2022

(54) BIS-CHOLINE TETRATHIOMOLYBDATE FOR TREATING WILSON DISEASE

(71) Applicant: Alexion Pharmaceuticals, Inc., Boston, MA (US)

(72) Inventors: Carl Bjartmar, Stockholm (SE); Karl-Heinz Weiss, Stockholm (SE); Michael Schilsky, Stockholm (SE); Frederick Askari, Stockholm (SE); Anna Czlonkowska, Stockholm (SE); Peter Ferenci, Stockholm (SE); Peter Hedera, Stockholm (SE); Aftab Ala, Stockholm (SE)

(73) Assignee: Alexion Pharmaceuticals, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/770,022

(22) PCT Filed: Dec. 4, 2018

(86) PCT No.: PCT/EP2018/083551
§ 371 (c)(1),
(2) Date: Jun. 4, 2020

(87) PCT Pub. No.: WO2019/110619
PCT Pub. Date: Jun. 13, 2019

(65) Prior Publication Data
US 2021/0137972 A1    May 13, 2021

Related U.S. Application Data

(60) Provisional application No. 62/750,595, filed on Oct. 25, 2018, provisional application No. 62/741,313, (Continued)

(51) Int. Cl.
A61K 33/24 (2019.01)
A61P 3/00 (2006.01)
A61K 9/00 (2006.01)

(52) U.S. Cl.
CPC ............ *A61K 33/24* (2013.01); *A61K 9/0053* (2013.01); *A61P 3/00* (2018.01)

(58) Field of Classification Search
None
See application file for complete search history.

(56) References Cited

U.S. PATENT DOCUMENTS 7,189,865 B2    3/2007    Ternansky et al.
9,623,021 B2    4/2017    Narayanan et al.
(Continued)

FOREIGN PATENT DOCUMENTS

RU    2604666 C2    12/2016
WO    2007084818 A2    7/2007

OTHER PUBLICATIONS

Brewer et al. "Initial Therapy of Patients with Wilson's Disease with Tetrathiomolybdate." Arch. Neurol. 1991, 48, p. 42-47.
(Continued)

*Primary Examiner* — Aradhana Sasan
(74) *Attorney, Agent, or Firm* — McDonnell, Boehnen, Hulbert & Berghoff LLP

(57) ABSTRACT

Methods for treating Wilson Disease with bis-choline tetrathiomolybdate therapy are provided. The methods may include administering 15 mg or between 30 and 90 mg of bis-choline tetrathiomolybdate once daily to a patient exhibiting NCC corrected, alamine aminotransferase (ALT), hemoglobin, platelets, or neutrophils levels meeting specified criteria. The methods may include modifying treatment
(Continued)

by decreasing or increasing the daily dose of bis-choline tetrathiomolybdate or discontinuing treatment for a period of time.

21 Claims, 23 Drawing Sheets

Related U.S. Application Data filed on Oct. 4, 2018, provisional application No. 62/669,095, filed on May 9, 2018, provisional application No. 62/655,568, filed on Apr. 10, 2018, provisional application No. 62/646,553, filed on Mar. 22, 2018, provisional application No. 62/594,184, filed on Dec. 4, 2017.

(56) References Cited

U.S. PATENT DOCUMENTS

| | | | |
|---|---|---|---|
| 2004/0019087 A1* | 1/2004 | Ternansky | A61P 25/28 514/357 |
| 2007/0207191 A1 | 9/2007 | Kanzer et al. | |
| 2021/0093588 A1* | 4/2021 | Bjartmar | A61K 9/28 |
| 2021/0177894 A1* | 6/2021 | Bjartmar | A61P 3/00 |

OTHER PUBLICATIONS

European Association for the Study of the Liver (EASL). "Clinical Practice Guidelines: Wilson's Disease." J. Hepatology. 2012, 56, p. 671-685.
Weiss et al. "Bis-choline tetrathiomolybdate in patients with Wilson's disease: an open-label, multicentre, phase 2 study." Lancet Gastroenterol Hepatol. 2017, 2, p. 869-876.
Hellman et al. "Mechanisms of copper incorporation into human ceruloplasmin." J. Biol. Chem. 2002, 48, p. 46632-46638.
Czlonkowska et al. "Unified Wilson's Disease Rating Scale—a proposal for the neurological scoring of Wilson's disease patients." Neurol Neurochir Pol. 2007, 41, p. 1-12.
Litwin et al. "Early neurological worsening in patients with Wilson's disease." Neurol Sci. 2015, 335, p. 162-167.
Wiernicka et al. "Gastrointestinal side effects in children with Wilson's disease treated with zinc sulphate." World J. Gastroenterol. 2013, 19, p. 4356-4362.
Wiess et al. "WTX101 in patients newly diagnosed with Wilson disease: final results of a global, prospective phase 2 trail." J. Hepatology. 2017, 66, p. S88.
Schilsky et al. "An ongoing Extension of a Phase 2 Study of WTX101 in Newly Diagnosed Wilson Disease Patients." Hepatology. 2017, 66, p. 429A.
Wiess et al. "Long-term efficacy and safety of WTX101 in Wilson disease: Data from an ongoing extension of a phase 2 study (WTX 101-201)." The International Liver Congress 2018 Abstract Book. Posters Thursday, Apr. 12, 2018. J. Hepatology. 2018, 68.
International Search Report and Written Opinion for International Application No. PCT/EP2018/083551, dated Mar. 3, 2019.
Müller et al. "Transition metal thiometalates: Properties and significance in complex and bioinorganics chemistry." Angewandte Chemie, International Edition in English. 1981, vol. 20, p. 934-955.
Binnie et al. "On the preparation, properties, and structure of cuprous ammonium thiomolybdate." Inorganic Chemistry. 1970, vol. 9, p. 1449-1452.
Laurie et al. "The copper-molybdenum antagonism in ruminants. III. reaction of copper(II) with tetrathiomolybdate (VI)." Inorganica Chimica Acta. 1986, vol. 123, p. 193-196.
Laurie et al. "Thiomolybdates—Simple but very versatile reagents." European Journal of Inorganic Chemistry. 2000, p. 2443-2450.
Walshe et al. "Copper: Its role in the pathogenesis of liver disease." Seminars in Liver Disease. 1984, vol. 4, p. 252-263.
Fabregues et al. "Ammonium tetrathiobolybdate in the decoppering phase treatment of Wilson's disease with neurological symptoms: A case series." Brain and Behavior. 2020, vol. 10(e01596) p. 1-7.
Chandrasekaran et al. "Aging of ammonium tetrathiomolybdate(VI) in air: an example of induced electron transfer by external oxidant, oxygen." Journal of the Less-Common Metals. 1987, vol. 134, p. L23-L25.
Ogra et al. "Metabolic fate of the insoluble copper/tetrathiomolybdate complex formed in the liver of LEC rats with excess tetrathiomolybdate." Journal of Inorganic Biochemistry. 2000, vol. 78, p. 123-128.
Maiti et al. "Diverse biological roles of the tetrathiomolybdate anion." Coordination Chemistry Reviews. 2021, ahead of publication, DOI: 110.1016/j.ccr.2020.213635.
Suttle et al. "Recent studies of the copper-molybdenum antagonism." Proceedings of the Nutrition Society. 1974, vol. 33, p. 299-305.
Brewer et al. "Treatment of Wilson Disease With Ammonium Tetrathiomolybdate." Arch Neurol, 2006, vol. 63, p. 521-527.
Brewer. "Tetrathiomolybdate anticopper therapy for Wilson's disease inhibits angiogenesis, fibrosis and inflammation." J. Cell. Mo.l Med., 2003, vol. 7, No. 1, p. 11-20.
Weiss et al. "An Ongoing Phase 2 Multi-Centre Open Label Study of WTC101 in Newly Diagnosed Wilson Disease Patients—Early Obersavations.", Journal of Hepatology, 2016, vol. 64, supplement 2, p. S145-S146.
Roberts et al. "Diagnosis and Treatment of Wilson Disease: An Update", AASLD Practice Guidelines, Hepatology, 2008, vol. 47, No. 6, p. 2089-2111.
Aggarwal et al. "Update on Wilson Disease", In International Review of Neurobiology. Elsevier, 2013, vol. 110, p. 313-348.
Aggarwal et al. "Advances in Treatment of Wilson Disease", Tremor and Other Hyperkinetic Movements, 2018, vol. 8, No. 525, p. 1-13.
Albarede et al. "Medical applications of Cu, Zn, and S isotope effects." Metallomics, 2016, vol. 8, p. 1056-1070.
Alvarez et al. "Tetrathiomolybdate Inhibits Copper Trafficking Proteins Through Metal Cluster Formation." Sciencexpress, 2009, 10.1126/science.1179907.
Alvarez et al. "Tetrathiomolybdate Inhibits Copper Trafficking Proteins Through Metal Cluster Formation." Science, 2010, vol. 327, No. 5963, p. 331-334.
Alvarez et al. "Tetrathiomolybdate Inhibits Copper Trafficking Proteins Through Metal Cluster Formation: Supplemental Material." Science, 2010, vol. 327, No. 5963, p. 331-334.
Avan et al. "Wilson's Disease Should be Treated with Zinc rather than Trientine or Penicillamine." Neuropediatrics, 2017, vol. 48, No. 5, p. 394-395.
Brewer et al. "Treatment of Wilson's disease with tetrathiomolybdate: V. control of free copper by tetrathiomolybdate and a comparison with trientine." Translational Research, 2009, vol. 154, No. 2, p. 70-77.
Chan et al. "Pharmacologic evaluation of ammonium tetrathiomolybdate after intravenous and oral administration to healthy dogs." AJVR, 2015, vol. 76, No. 5, p. 445-453.
Czlonkowska et al. "D-penicillamine versus zinc sulfate as first-line therapy for Wilson's disease." European Journal of Neurology, 2014, vol. 21, p. 599-606.
Czlonkowska et al. "Wilson's disease—cause of mortality in 164 patients during 1992-2003 observation period." J. Neurol. 2005, vol. 252, p. 698-703.
Danks, D. M. "Copper-induced dystonia secondary to cholestatic liver disease." The Lancent, 1990, vol. 335, p. 410.
De Bie et al. "Molecular pathogenesis of Wilson and Menkes disease: correlation of mutations with molecular defects and disease phenotypes." J. Med. Genet., 2007, vol. 44, p. 673-688.
Danks, D. M. "Chapter 68: Disorders of Copper Transport," In The Metabolic and Molecular Bases of Inherited Disease, 7th ed.; Sriver, C.R,; Beaudet, A.L., Sly, W.S., Valle, D.; McGraw-Hill,:New York. 1995; p. 2211-2235.
Dyson et al. "Ammonium tetrathiomolybdate following ischemia/reperfusion injury: Chemistry, pharmacology, and impact of a new class of sulfide donor in preclinical injury models." PLOS Medicine, 2017, https://doi.org/10.1371/journal.pmed.1002310, p. 1-24.

(56) References Cited

OTHER PUBLICATIONS

Gibbs et al. "Liver copper concentration in Wilson's disease: Effect of treatment with 'anti-copper' agents." Journal of Gastroenterology and Hepatology, 1990, vol. 5, p. 420-424.
Halverson et al. "A Mechanism for the Copper-Molybdenum Interrelationship." J. Nutrition, 1960, vol. 71, p. 95-100.
Harada, M. "Pathogenesis and management of Wilson disease." Hepatology Research, 2014, vol. 44, p. 395-402.
Harper et al. "Reversible Pancytopenia Secondary to Treatment with Tetrathiomolybdate." British Journal of Haematology, 1986, vol. 64, No. 4, p. 851-853.
Hartard et al. "Wilson's disease with cerebral manifestation: monitoring therapy by CSF copper concentration." J. Neurol., 1993, vol. 241, p. 101-107.
Haywood et al. "Metal (molybdenum, copper) accumulation and retention in brain, pituitary and other organs of ammonium tetrathiomolybdate-treated sheep " British Journal of Nutrition, 1998, vol. 79, p. 329-331.
Hedera, P. "Updated on the clinical management of Wilson's disease." The Application of Clinical Genetics, 2017, vol. 10, p. 9-19.
Hefter et al. "Long-term outcome of neurological Wilson's disease." Parkinsonism and Related Disorders, 2018, vol. 49, p. 48-53.
Dalma, H. "Extrahepatic Manifestations of Wilson Disease." Ph.D. Dissertation, Semmelweis University, Budapest, 2003.
Houwen, R. "Bis-choline tetrathiomolybdate for Wilson's disease." Lancet Gastroenterol Hepatol, 2017, http://dx.doi.org/10.1016/S2468-1253(17)30325-4, p. 1-2.
Komatsu et al. "Excretion of copper complexed with thiomolybdate into the bile and blood in LEC rats." Chemico-Biological Interactions, 2000, vol. 124, p. 217-231.
Li et al. "Current Drug Managements of Wilson's Disease: From West to East." Current Neuropharmacology, 2016, vol. 14, p. 322-325.
Liu et al. "Epidemiology, diagnosis, and treatment of Wilson's disease." Intractable & Rare Diseases Research, 2017, vol. 6, No. 4, p. 249-255.
Lorincz, M. T. "Chapter 18: Wilson disease and related copper disorders." In Handbook of Clinical Neurology, Geschwind, D.H, Paulson, H.L, and Klein, C.; Elsevier, 2018, vol. 147 (3rd series), p. 279-292.
Mason, J. "Thiomolybdates: Mediators of Molybdenum Toxicity and Enzyme Inhibitors." Toxicology, 1986, vol. 42, p. 99-109.
McQuaid et al. "A Comparison of the Effects of Penicillamine, Trientine, and Trithiomolybdate on [35S]-Labeled Metallothionein In Vitro; Implications for Wilson's Disease Therapy." Journal of Inorganic Biochemistry, 1990, vol. 41, p. 87-92.
Medici et al. "Adverse Reaction after Tetrathiomolybdate Treatment for Wilson's Disease: A Case Report." Movement Disorders, 2006, vol. 21, No. 11, p. 2030-2032.
Medici et al. "Tetrathiomolybdate, a copper chelator for the treatment of Wilson disease, pulmonary fibrosis and other indications." IDrugs, 2008, vol. 11, No. 8, p. 592-606.
Pfeiffer, R. F. "Wilson's Disease." Seminars in Neurology, 2007, vol. 27, No. 2, p. 123-132.
Pierson et al. "The Function of ATPase Copper Transporter ATP7B in Intestine." Gastroenterology, 2018, vol. 154, p. 168-180.
Roberts, E. A. "Update on the Diagnosis and Management of Wilson Disease." Current Gastroenterology Reports, 2018, vol. 20, No. 56, p. 1-12.
Rodriguez-Castro et al. "Wilson's disease: A review of what we have learned." World Journal of Hepatology, 2014, vol. 7, No. 29, p. 2859-2870.
Schilsky, M. L. "Diagnosis and Long-Term Management of Wilson Disease." Gastroenterology & Hepatology, 2007, vol. 3, No. 1, p. 27-29.
Smirnova et al. "Copper(I)-binding properties of de-coppering drugs for the treatment of Wilson disease. α-Lipoic acid as a potential anti-copper agent." Scientific Reports, 2018, vol. 8, No. 1463, p. 1-9.

Stuerenburg, H. J. "CSF copper concentrations, blood-brain barrier function, and coeruloplasmin synthesis during the treatment of Wilson's disease." J. Neural Transm, 2000, vol. 107, p. 321-329.
Suzuki, et al. "Selective removal of copper bound to metallothionein in the liver of LEC rats by tetrathiomolybdate." Toxicology, 1993, vol. 83., p. 149-158.
Suzuki et al. "Mechanisms for Removal of Copper form Metallothionein by Tetrathiomolybdate." Journal of Inorganic Biochemistry, 1994, vol. 54, p. 157-165.
Suzuki et al. "Molybdenum and Copper Kinetics after Tetrathiomolybdate Injection in LEG Rats: Specific role of Serum Albumin." J. Trace Elements Med. Biol., 1995, vol. 9, p. 170-175.
Walshe, J. M. "Tetrathiomolybdate (MoS4) as an "anti-copper" agent in man." In Orphan Diseases and Orphan Drugs; Scheinburg, I. H., Walshe, J. M.; Manchester University Press, 1986; p. 76-85.
Walshe, J. M. "Wilson's Disease Patients Can Be Decoppered." The Lancet, 1989, https://doi.org/10.1016/S0140-6736(89)90419-4, p. 228.
Walshe et al. "Chelation treatment of neurological Wilson's disease." Quarteriy Journal of Medicine, 1993, vol. 86, p. 197-204.
Walshe, J. M. "Monitoring Copper in Wilson's Disease." Advances in Clinical Chemistry, 2010, vol. 50, p. 151-163.
Weiss et al. "WTX101—an investigational drug for the treatment of Wilson disease." Expert Opinion on Investigational Drugs, 2018, vol. 27, No. 6, p. 561-567.
Woods et al. "Spectral and Kinetic Studies on the Binding of Trithiomolybdate to Bovine and Canine Serum Albumin In Vitro: The Interaction with Copper." Journal of Inorganic Biochemistry, 1987, vol. 30, p. 261-272.
Allen et al. "Involvement of Organic Molybdenum Compounds in the Interaction between Copper, Molybdenum, and Sulfur." Journal of Inorganic Biochemistry, 1986, vol. 27, p. 95-112.
Bremner et al. "Copper Metabolism in Rats Given Di- or Trithiomolybdates." Journal of Inorganic Biochemistry, 1982, vol. 16, p. 109-119.
Comar et al. "Molybdenum Metabolism and Interrelationships with Copper and Phosphorus." Journal of Biological Chemistry, 1949, vol. 180, No. 2, p. 913-922.
Czachor et al. "Reduction of copper and metallothionein in toxic milk mice by tetrathiomolybdate, but not deferiprone." Journal of Inorganic Biochemistry, 2002, vol. 88, p. 213-222.
Dick et al. "Thiomolybdates and the copper-molybdenum-sulphur interaction in ruminant nutrition." J. agric. Sci. Camb., 1975, vol. 85, p. 567-568.
Dick et al. "Some Preliminary Observations On The Effect Of Molybdenum On Copper Metabolism In Herbivorous Animals." The Australian Veterinary Journal, 1945, vol. 21, p. 70-72.
George et al. "Tetrathiomolybdate causes formation of hepatic copper-molybdenum cluster in an animal model of Wilson's disease: Abstract." J. Am. Chem. Soc., 2003, vol. 125, No. 7, p. 1704-1705.
George et al. "Tetrathiomolybdate causes formation of hepatic copper-molybdenum cluster in an animal model of Wilson's disease." J. Am. Chem. Soc., 2003, vol. 125, No. 7, p. 1704-1705.
Gooneratne et al. "An investigation of the effects of intravenous administration of thiomolybdate on copper metabolism in chronic Cu-poisoned sheep." Br. J. Nutr., 1981, vol. 46, p. 469-480.
Gooneratne et al. "Intravenous administration of thiomolybdate for the prevention and treatment of chronic copper poisoning in sheep" Br. J. Nutr., 1981, vol. 46, p. 457-467.
Gould et al. "Role of the rumen in copper and thiomolybdate absorption." Nutrition Research Reviews, 2011, vol. 24, p. 176-182.
Howell et al. "Effect of Intravenously Administered Tetrathiomolybdate on Plasma Copper Concentrations of Copper-loaded Sheep" J. Comp. Path., 1990, vol. 103, p. 321-334.
Humphries et al. "Use of ammonium tetrathiomolybdate in the treatment of copper poisoning in sheep." The Veterinary Record, 1986, vol. 119, No. 24, p. 596-598.
Jones, H. B. "X-ray microanalysis of liver and kidney in copper loaded sheep with and without thiomolybdate administration." Research in Veterinary Science, 1984, vol. 37, p. 273-282.

(56) References Cited

OTHER PUBLICATIONS

Ke et al. "Enhancement of tetrathiomolybdate-induced biliary copper excretion in sheep by general anaesthesia and the effect on copper excretion in urine and bile." Research in Veterinary Science, 1989, vol. 46, p. 344-348.
Klein et al. "Tetrathiomolybdate in the treatment of acute hepatitis in an animal model for Wilson disease." Journal of Hepatology, 2004, vol. 40, p. 409-416.
Kumaratilake et al. "Effects of intravenously administered tetrathiomolybdate on the distribution of copper in th liver and kidney of copper loaded sheep: a histochemical study." Research in Veterinary Science, 1987, vol. 42, p. 154-161.
Kumaratilake et al. "Intravenously Administered Tetrathiomolybdate and the Removal of Copper from the Liver of Copper-loaded Sheep." J. Comp. Path. 1989, vol. 101, p. 177-199.
Lannon et al. "The Inhibition of Bovine Ceruloplasmin Oxidase Activity by Thiomolybdates in Vivo an in Vitro: A Reversible Interaction." Journal of Inorganic Biochemistry, 1986, vol. 26, p. 107-115.
Mason et al. "Accumulation of copper on albumin in bovine plasma in vivo after intravenous trithiomolybdate administration." Research in Veterinary Science, 1986, vol. 41, p. 108-113.
Mason et al. "Studies of the changes in systemic copper metabolism and excretion produced by the intravenous administration of trithiomolybdate in sheep." British Journal of Nutrition, 1988, vol. 59, p. 289-300.
Mills et al. "Copper and Molybdenum Absorption by Rats Given Ammonium Tetrathiomolybdate." Journal of Inorganic Biochemistry, 1981, vol. 14, p. 163-175.
Ogra et al. "Systematic Dispositions of Molybdenum and Copper after Tetrathiomolybdate Injection in LEC Rats." J. Trace Elements Med. Biol., 1995, vol. 9, p. 165-169.
Ogra et al. "Mechanism of selective copper removal by tetrathiomolybdate from metallothionein in LEC rats." Toxicology, 1996, vol. 106, p. 75-83.
Ogra et al. "Effect of glutathion depletion on removal of copper from LEC rat livers by tetrathiomolybdate." Journal of Inorganic Biochemistry, 2010, vol. 104, p. 858-862.
Ogra et al. "Removal and efflux of copper from Cu-metallothionein as Cu/tetrathiomolybdate complex in LEC rats." Research Communications in Molecular Pathology and Pharmacology, 1995, vol. 88, No. 2, p. 196-204.
Reed et al. "Animals models of Wilson disease." Journal of Neurochemistry, 2018, vol. 146, p. 356-373.
Song et al. "Tetrathiomolybdate Protects against Bile Duct Ligation-Induced Cholestic Liver Injury and Fibrosis." Journal of Pharmacology and Experimental Therapeutics, 2008, vol. 325, No. 2, p. 409-4016.
Spence et al. "A Sequential Study of the Skeletal Abnormalities which Develope in Rats Given a Small Dietary Supplement of Ammonium Tetrathiomolybdate." J. Comp. Path., 1980, vol. 90, p. 139-153.
Sugawara et al. "Removal of Copper form the Liver of Long-Evans Cinnamon (LEC) Rats by Tetrathiomolybdate (TTM) Injection: The Main Excretion Route is via Blood, not Bile." Research Communications in Molecular Pathology and Pharmacology, 1994, vol. 85, No. 2, p. 217-226.
Sugawara et al. "The Effect of Subcutaneous Tetrathiomolybdate Administration on Copper and Iron Metabolism, Including their Regional Redistribution in the Brain, in the Long-Evans Cinnamon Rat, a bona fide Animal Model for Wilson's Disease." Pharmacology & Toxicology, 1999, vol. 82, p. 211-217.
Sugawara et al. "Therapeutic Effects of Tetrathiomolybdate on Hepatic Dysfunction Occurring Naturally in Long-Evans Cinnamon (LEC) Rats: A Bona Fide Animal Model for Wilson's Disease." Research Communications in Molecular Pathology and Pharmacology, 1999, vol. 103, No. 2, p. 177-187.
Wang et al. "The Uptake and Intracellular Distribution of [35S] Trithiomolybdate in Bovine Liver In Vivo." Journal of Inorganic Biochemistry, 1987, vol. 31, p. 85-93.
Wang et al. "Treatment of copper poisoning in goats by the injection of trithiomolybdate." Small Ruminant Research, 1992, vol. 8, p. 31-40.
Wang et al. "Studies on the Uptake and Subsequent Tissue Distribution of [35S] Trithiomolybdate in Rats: Effects on Metallothionein Copper in Liver, Kidney, and Intestine." Journal of Inorganic Biochemistry, 1988, vol. 33, p. 19-29.
Zhang et al. "Effects of tetrathiomolybdate and penicillamine on brain hydroxyl radical and fee copper levels: A microdialysis study in vivo." Biochemical and Biophysical Research Communications, 2015, vol. 458, p. 82-95.
Lozeron, P. et al., "Inhibitory rTMS applied on somatosensory cortex in Wilson's disease patients with hand Tystonia." J. Neural. Transm., vol. 124, No. 10, 2017, pp. 1161-1170.

\* cited by examiner

BIS-CHOLINE TETRATHIOMOLYBDATE FOR TREATING WILSON DISEASE

CROSS-REFERENCE TO RELATED APPLICATIONS

The present application is a national stage application under 35 U.S.C. § 371 of International Application No. PCT/EP2018/083551, filed Dec. 4, 2018, which claims priority to U.S. Provisional Application No. 62/594,184, filed Dec. 4, 2017; U.S. Provisional Application No. 62/646,553, filed Mar. 22, 2018; U.S. Provisional Application No. 62/655,568, filed Apr. 10, 2018; U.S. Provisional Application No. 62/669,095, filed May 9, 2018; U.S. Provisional Application No. 62/741,313, filed Oct. 4, 2018; and U.S. Provisional Application No. 62/750,595, filed Oct. 25, 2018, each of which is incorporated herein by reference in its entirety for all purposes.

BACKGROUND

Wilson Disease (WD) is an autosomal recessive disorder of impaired copper (Cu) metabolism. Mutations in the ATP7B gene result in deficient production of the Cu-transporter ATPase2, leading to impaired incorporation of Cu into ceruloplasmin, impaired biliary excretion of Cu, increased free and albumin-bound Cu, and Cu accumulation in liver, brain, and other tissues, with resulting organ damage and dysfunction. The prevalence of WD is estimated at 1 in 30,000 people, corresponding to approximately 10,000 individuals in the United States and approximately 15,000 individuals in the European Union.

Typical clinical presentation of WD is in adolescence to early adulthood. Genetic screening and genotype-phenotype correlation is complicated by a multitude of associated ATP7B mutations; most individuals with WD are compound heterozygotes. Initial signs and symptoms of WD are predominantly hepatic (~40%), neurologic (~40%), or psychiatric (~20%), but patients often develop combined hepatic and neuropsychiatric disease. Untreated or inadequately treated patients have progressive morbidity, and mortality is usually secondary to decompensated hepatic cirrhosis and liver failure. Liver transplantation is the only effective therapy for WD-associated acute liver failure; other causes of death associated with WD include hepatic malignancy and neurologic deterioration with severe inanition.

The liver represents one of the main Cu storage organs in humans. In healthy people, intracellular Cu homeostasis is tightly regulated. Copper is incorporated into cells by Cu transporter 1 (CTR1), and then transported from CTR1 to Cu chaperones such as the Cu chaperones for antioxidant 1, cytochrome c oxidase, and superoxide dismutase. Copper accompanying the chaperone is delivered to a specific Cu-requiring enzyme. If excess amounts of Cu appear, the excess Cu is bound to metallothionein (MT) as monovalent Cu (Cu+) via Cu thiolate bridges by abundant cysteine residues in MT, thus leading to a detoxification of Cu through a reduction of its redox potential.

In WD patients, excretion of Cu is impaired due to the ATPase2 deficiency. This results in an accumulation of Cu, mainly in the liver and brain, but also in other organs. Within the buffer capacity of MT, no apparent toxicity of Cu exists because MT tightly binds Cu. However, beyond the Cu buffering capacity of MT, free Cu ions appear and this excessive amount of free intracellular Cu triggers pro-oxidant properties, leading to an increased risk of tissue/organ damages with clinical manifestations as a result. It is assumed that the toxicity of Cu in WD is mediated by the free or loosely bound Cu that is not tightly bound to MT due to the Cu overload.

Treatment goals in WD focus on compensating for the impaired Cu excretion caused by the ATPase2 deficiency. The current treatments for WD are general chelator therapies D-penicillamine (CUPRIMINE®, Valeant Pharmaceuticals, DEPEN®, Meda Pharmaceuticals) and trientine (SYPRINE®, Aton Pharma, Inc.), which non-specifically chelate Cu and promote urinary Cu excretion. In addition, zinc (Zn), which blocks dietary uptake of Cu, is used mainly for maintenance treatment. Zinc impairs the absorption of Cu by the induction of MT in the gastrointestinal (GI) tract.

Disease control in patients with neurological symptoms at WD diagnosis is an area of particular concern. More than a third of patients presenting with neurological symptoms show no improvement after 4 years of treatment with chelators. This failure to respond to chelation therapy with neurological presentation may reflect irreversible damage to the nervous system. Also, in a recent study, approximately 50% of patients had residual neurological symptoms despite years of therapy on a Cu-modulating agent. Worsening of neurological symptoms on initiation of treatment has been reported in approximately 25% of patients initiated on penicillamine and trientine, and up to 50% of those patients never recover. The mechanism behind this "paradoxical" neurological worsening is believed to be a mobilisation of Cu from the liver leading to Cu elevations in blood and the central nervous system causing neurological deterioration. This theory is supported by non-clinical data.

Currently available drugs for treating WD have high rates of treatment discontinuation due to adverse events and treatment failure. Their adverse event profiles and complicated dosing regimens lead to poor treatment compliance and high rates of treatment failure, a major concern in a disease such as WD that requires life-long treatment.

Tetrathiomolybdate in the form of an ammonium salt has been demonstrated to provide Cu control and improvement of hepatic function after even a single dose. The majority of clinical and non-clinical safety and toxicity testing for tetrathiomolybdate-based treatments have been carried out using ammonium as the cationic counterion.

The drug absorption of an orally administered active agent may be influenced by food ingested prior to or after the active agent is administered. Food may influence drug absorption through several mechanisms. The food may affect the absorption by interacting with the active agent or the pharmaceutical formulation in the gastrointestinal tract, by stimulating bile flow, by changing the gastrointestinal pH, by increasing splanchnic blood flow, or by delaying gastric emptying. Thus, the bioavailability of an active agent may be affected by the ingestion of food within about 2 hours before or about 1 hour after the administration of an active agent.

Nonetheless, it is difficult to predict, de novo, whether or not a particular active agent or pharmaceutical formulation will exhibit a food effect. Furthermore, even if present, the food effect for an active agent or pharmaceutical formulation may result in an increase or a decrease in bioavailability in the fed conditions compared to the administration of an equivalent dose under fasted conditions. In cases where there is a substantial food effect (i.e., food ingestion prior to or after dose administration causes a substantial increase or decrease in drug absorption relative to administration in the fasted state), the pharmaceutical formulations administered in the fed conditions are not bioequivalent to the same pharmaceutical formulations administered under fasted conditions.

This lack of bioequivalence may have profound clinical consequences. For example, administering a pharmaceutical composition with food may provide dangerously high drug blood plasma levels of the active agent resulting clinical adverse effects. Alternatively, administering a pharmaceutical composition under fasted conditions may provide an efficacious dose whereas administering the composition with food may provide sub-therapeutic drug blood plasma levels such that the fed dose is not efficacious.

Thus, there is a need to develop methods for treating Wilson Disease that are efficacious in improving Cu metabolism, reducing toxic free Cu, and maintaining normal Cu levels to improve patients' symptoms, without the side-effects associated with currently available treatments.

SUMMARY OF THE INVENTION

The present disclosure relates to methods for treating Wilson Disease with bis-choline tetrathiomolybdate therapy. In some embodiments bis-choline tetrathiomolybdate has the structure:

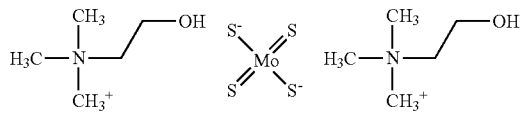

In some embodiments, the disclosure relates to methods of treating Wilson Disease in a patient by administering 15 mg of bis-choline tetrathiomolybdate once daily or once every day. In some embodiments, the disclosure relates to methods of treating Wilson Disease in a patient by administering from 30 to 90 mg of bis-choline tetrathiomolybdate daily. In further embodiments, the disclosure relates to methods of treating Wilson Disease in a patient by administering from 30 to 90 mg of bis-choline tetrathiomolybdate daily, where the patient has one or more of the following: an $NCC_{corrected}$ greater than 2.3 μm/L, alanine aminotransferase (ALT) level less than 80 IU/mL, hemoglobin of greater than 8 g/dL, platelets greater than 30,000/4, or neutrophils greater than 1,000/4, or $1 \times 10^3$/μL.

In some embodiments the disclosure relates to methods of modifying bis-choline tetrathiomolybdate administration to a patient with Wilson Disease undergoing bis-choline tetrathiomolybdate treatment by decreasing the daily dose of bis-choline tetrathiomolybdate or by increasing the daily dose of bis-choline tetrathiomolybdate.

In one aspect, the present disclosure further provides methods for decreasing or increasing the daily dose of bis-choline tetrathiomolybdate in a patient exhibiting an abnormal test result, including optionally discontinuing treatment for a period of time.

In another aspect, the present disclosure provides pharmaceutical compositions for treating Wilson Disease in a patient comprising bis-choline tetrathiomolybdate. In another aspect, the present disclosure provides kits for treating Wilson Disease, comprising at least three sets of pharmaceutical dosage units; and instructions for use.

In another aspect, the present disclosure relates to methods for treating Wilson Disease in a patient in need thereof comprising administering bis-choline tetrathiomolybdate in a fasted state. In certain aspects, bis-choline tetrathiomolybdate is administered as an enterically coated formulation.

In yet another aspect, the present disclosure relates to methods of treating Wilson Disease in a patient in need thereof comprising administering bis-choline tetrathiomolybdate for about 24 weeks or longer, about 36 weeks or longer, about 48 weeks or longer, about 60 weeks or longer, about 72 weeks or longer, about 84 weeks or longer, about 92 weeks or longer, about 120 weeks or longer, about 132 weeks or longer, or about 144 weeks or longer.

In certain embodiments, the disclosure is directed to a pharmaceutical composition comprising 15 mg of bis-choline tetrathiomolybdate for use in treating Wilson Disease in a patient in need thereof. In particular embodiments, the pharmaceutical composition comprising 15 mg of bis-choline tetrathiomolybdate is suitable for once daily dosing. In further embodiments, the pharmaceutical composition is suitable for once every other day dosing. In still further embodiments, the pharmaceutical composition is a delayed-release pharmaceutical composition. In yet further embodiments, the pharmaceutical composition is in the form of a tablet or capsule. In even further embodiments, the pharmaceutical composition is in the form of a tablet. In particular embodiments, the pharmaceutical composition is in the form of an enterically coated tablet.

In certain embodiments of the disclosure, the patient exhibits a reduction in $NCC_{corrected}$ as measured after 24 weeks of administration as compared to the patient's $NCC_{corrected}$ as measured prior to administration, such as a 20%, 35%, 50%, or 75%, reduction in $NCC_{corrected}$ as measured after 24 weeks of administration as compared to the patient's $NCC_{corrected}$ as measured prior to administration.

In particular embodiments of the disclosure, the patient exhibits a reduction in $NCC_{corrected}$ as measured after 48 weeks of administration as compared to the patient's $NCC_{corrected}$ as measured prior to administration, such as a 20%, 35%, 50%, or 75%, reduction in $NCC_{corrected}$ as measured after 48 weeks of administration as compared to the patient's $NCC_{corrected}$ as measured prior to administration.

In particular embodiments of the disclosure, the patient exhibits a reduction in $NCC_{corrected}$ as measured after 72 weeks of administration as compared to the patient's $NCC_{corrected}$ as measured prior to administration, such as a 20%, 35%, 50%, or 75%, reduction in $NCC_{corrected}$ as measured after 72 weeks of administration as compared to the patient's $NCC_{corrected}$ as measured prior to administration.

In certain embodiments, the disclosure is directed to a pharmaceutical composition comprising bis-choline tetrathiomolybdate for use in treating Wilson Disease in a patient in need thereof, wherein 30, 45, 60, 75, or 90 mg of bis-choline tetrathiomolybdate is administered daily and the patient has one or more of the following:
  a) an $NCC_{corrected}$ greater than 2.3 μm/L;
  b) alanine aminotransferase (ALT) level less than 80 IU/mL;
  c) hemoglobin of greater than 8 g/dL;
  d) platelets greater than 30,000/μL; or
  e) neutrophils greater than $10^3$/μL.

In particular embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is reduced when said patient exhibits an alanine aminotransferase (ALT) level at least twice that of the ALT level exhibited when starting bis-choline tetrathiomolybdate treatment. In certain embodiments, if the patient was on a 15 mg once daily dose of bis-choline tetrathiomolybdate, the dose is reduced to 15 mg bis-choline tetrathiomolybdate every other day; if the patient was on a 30 mg once daily dose of bis-choline tetrathiomolybdate, the dose is reduced to 15 mg bis-choline tetrathiomolybdate once daily; if the patent was on a 45 mg once daily dose of bis-choline tetrathiomolybdate, the dose is reduced to 30 mg bis-choline tetrathiomolybdate once daily; if the patent was on a 60 mg once daily dose of bis-choline tetrathiomolybdate, the dose is reduced to 45 mg bis-choline tetrathiomolybdate once daily; if the patent was on a 75 mg once daily dose of bis-choline tetrathiomolybdate, the dose is reduced to 60 mg bis-choline tetrathiomolybdate once daily; or if the patent was on a 90 mg once daily dose of bis-choline tetrathiomolybdate, the dose is reduced to 75 mg bis-choline tetrathiomolybdate once daily.

In further embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is reduced when said patient exhibits an alanine aminotransferase (ALT) level at least twice least twice the upper limit of normal (ULN). In still further embodiments, if the patient was on a 15 mg once daily dose of bis-choline tetrathiomolybdate, the dose is reduced to 15 mg bis-choline tetrathiomolybdate every other day; if the patient was on a 30 mg once daily dose of bis-choline tetrathiomolybdate, the dose is reduced to 15 mg bis-choline tetrathiomolybdate once daily; if the patent was on a 45 mg once daily dose of bis-choline tetrathiomolybdate, the dose is reduced to 30 mg bis-choline tetrathiomolybdate once daily; if the patent was on a 60 mg once daily dose of bis-choline tetrathiomolybdate, the dose is reduced to 45 mg bis-choline tetrathiomolybdate once daily; if the patent was on a 75 mg once daily dose of bis-choline tetrathiomolybdate, the dose is reduced to 60 mg bis-choline tetrathiomolybdate once daily; or if the patent was on a 90 mg once daily dose of bis-choline tetrathiomolybdate, the dose is reduced to 75 mg bis-choline tetrathiomolybdate once daily. In yet further embodiments, the ULN is 30-45 IU/mL. In more particular embodiments, the ULN is 34 IU/mL. In still more particular embodiments, the ULN is 40 IU/mL.

In particular embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is reduced when said patient exhibits a hemoglobin level of 70% or less than the hemoglobin level exhibited when starting bis-choline tetrathiomolybdate treatment. In certain embodiments, if the patient was on a 15 mg once daily dose of bis-choline tetrathiomolybdate, the dose is reduced to 15 mg bis-choline tetrathiomolybdate every other day; if the patient was on a 30 mg once daily dose of bis-choline tetrathiomolybdate, the dose is reduced to 15 mg bis-choline tetrathiomolybdate once daily; if the patent was on a 45 mg once daily dose of bis-choline tetrathiomolybdate, the dose is reduced to 30 mg bis-choline tetrathiomolybdate once daily; if the patent was on a 60 mg once daily dose of bis-choline tetrathiomolybdate, the dose is reduced to 45 mg bis-choline tetrathiomolybdate once daily; if the patent was on a 75 mg once daily dose of bis-choline tetrathiomolybdate, the dose is reduced to 60 mg bis-choline tetrathiomolybdate once daily; or if the patent was on a 90 mg once daily dose of bis-choline tetrathiomolybdate, the dose is reduced to 75 mg bis-choline tetrathiomolybdate once daily.

In particular embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is reduced when said patient exhibits a platelet level of 70% or less than the platelet level exhibited when starting bis-choline tetrathiomolybdate treatment. In certain embodiments, if the patient was on a 15 mg once daily dose of bis-choline tetrathiomolybdate, the dose is reduced to 15 mg bis-choline tetrathiomolybdate every other day; if the patient was on a 30 mg once daily dose of bis-choline tetrathiomolybdate, the dose is reduced to 15 mg bis-choline tetrathiomolybdate once daily; if the patent was on a 45 mg once daily dose of bis-choline tetrathiomolybdate, the dose is reduced to 30 mg bis-choline tetrathiomolybdate once daily; if the patent was on a 60 mg once daily dose of bis-choline tetrathiomolybdate, the dose is reduced to 45 mg bis-choline tetrathiomolybdate once daily; if the patent was on a 75 mg once daily dose of bis-choline tetrathiomolybdate, the dose is reduced to 60 mg bis-choline tetrathiomolybdate once daily; or if the patent was on a 90 mg once daily dose of bis-choline tetrathiomolybdate, the dose is reduced to 75 mg bis-choline tetrathiomolybdate once daily.

In particular embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is reduced when said patient exhibits a neutrophils level of 70% or less than the neutrophils level exhibited when starting bis-choline tetrathiomolybdate treatment. In certain embodiments, if the patient was on a 15 mg once daily dose of bis-choline tetrathiomolybdate, the dose is reduced to 15 mg bis-choline tetrathiomolybdate every other day; if the patient was on a 30 mg once daily dose of bis-choline tetrathiomolybdate, the dose is reduced to 15 mg bis-choline tetrathiomolybdate once daily; if the patent was on a 45 mg once daily dose of bis-choline tetrathiomolybdate, the dose is reduced to 30 mg bis-choline tetrathiomolybdate once daily; if the patent was on a 60 mg once daily dose of bis-choline tetrathiomolybdate, the dose is reduced to 45 mg bis-choline tetrathiomolybdate once daily; if the patent was on a 75 mg once daily dose of bis-choline tetrathiomolybdate, the dose is reduced to 60 mg bis-choline tetrathiomolybdate once daily; or if the patent was on a 90 mg once daily dose of bis-choline tetrathiomolybdate, the dose is reduced to 75 mg bis-choline tetrathiomolybdate once daily.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits an alanine aminotransferase (ALT) level greater than five times that of the ALT level exhibited when starting bis-choline tetrathiomolybdate treatment, and once said patient exhibits an ALT level less than twice that of the level exhibited when starting bis-choline tetrathiomolybdate treatment, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits an alanine aminotransferase (ALT) level greater than 200 IU/ml, and once said patient exhibits an ALT level less than twice that of the level exhibited when starting bis-choline tetrathiomolybdate treatment, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits a hemoglobin level of less than 8 g/dL, and once said patient exhibits a hemoglobin level equivalent to that exhibited when starting bis-choline tetrathiomolybdate treatment, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of his-choline tetrathiomolybdate for use in treating Wilson Disease in a patient undergoing bis-choline tetrathiomolybdate treatment, wherein the daily dose of bis-choline tetrathiomolybdate is discontinued when said patient exhibits platelet levels of less than 30,000 µL, and once said patient exhibits a platelet level equivalent to that exhibited when starting bis-choline tetrathiomolybdate treatment, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits neutrophils levels of less than $1.0\times10^3/\mu L$, and once said patient exhibits a neutrophils level equivalent to that exhibited when starting bis-choline tetrathiomolybdate treatment, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits bilirubin level greater than 2.4 mg/dL and alanine aminotransferase (ALT) levels greater than 120 IU/mL, and once said patient exhibits a bilirubin level below the upper limit of normal, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg his-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure is directed to a pharmaceutical composition of bis-choline tetrathiomolybdate for use in treating Wilson Disease in a patient undergoing bis-choline tetrathiomolybdate treatment, wherein the daily dose of bis-choline tetrathiomolybdate is discontinued when said patient exhibits bilirubin level greater than twice the upper limit of normal for bilirubin and alanine aminotransferase (ALT) levels greater than three times the ULN for ALT, and once said patient exhibits a bilirubin level below the upper limit of normal, treatment is resumed at 15 mg bis-choline tetrathiomolybdate every other day if the patient was on a 15 mg every other day dose of bis-choline tetrathiomolybdate prior to discontinuing bis-choline tetrathiomolybdate, or 15 mg bis-choline tetrathiomolybdate daily if the patient was on a 15 to 90 mg once daily dose of bis-choline tetrathiomolybdate prior to discontinuing bis-choline tetrathiomolybdate.

In certain embodiments, the disclosure provides a composition comprising bis-choline tetrathiomolybdate for use in a method of treating Wilson Disease in a patient. In some embodiments, the composition is defined according to any of the compositions disclosed herein. In some embodiments, the composition is for use in any of the methods disclosed herein. In some embodiments, the patient is defined as disclosed herein.

In certain embodiments, the disclosure is directed to a pharmaceutical composition of bis-choline tetrathiomolybdate for use in treating Wilson Disease wherein the composition is administered in the fasted state. In further embodiments the pharmaceutical composition comprises 15 mg of bis-choline tetrathiomolybdate. In still further embodiments the pharmaceutical composition is an enterically coated tablet.

In certain embodiments, the disclosure relates to the above methods of treating Wilson Disease comprising administering bis-choline tetrathiomolybdate to patients with Wilson Disease and modifying bis-choline tetrathiomolybdate to patients with Wilson Disease wherein the patient has cirrhosis.

In certain embodiments, the disclosure relates to the above methods of treating Wilson Disease comprising administering bis-choline tetrathiomolybdate to patients with Wilson Disease and modifying bis-choline tetrathiomolybdate to patients with Wilson Disease wherein the patient does not have cirrhosis.

In particular embodiments, the disclosure relates to the above methods of treating Wilson Disease comprising administering bis-choline tetrathiomolybdate to patients with Wilson Disease and modifying bis-choline tetrathiomolybdate to patients with Wilson Disease, wherein the patient exhibits one or more phenotype of Wilson Disease selected from total tremor; total gait; dystonia; limb agility and coordination; and rigidity; preferably wherein the patient exhibits total tremor or limb agility and coordination or both. In further embodiments, the a) total tremor phenotype comprises one or more neurological manifestation of Wilson Disease according to the Unified Wilson Disease Rating Scale (UWDRS) part III selected from: resting tremor; head tremor; arms—postural tremor and wing-beating tremor; postural tremor—legs; and jaw tremor; b) total gait phenotype comprises one or more neurological manifestation of Wilson Disease according to the Unified Wilson Disease Rating Scale (UWDRS) part III selected from: arising from chair; posture—trunk dystonia, ataxia of stance, and parkinsonism; gait—leg dystonia, ataxia, and parkinsonism; c) dystonia phenotype comprises one or more neurological manifestation of Wilson Disease according to the Unified Wilson Disease Rating Scale (UWDRS) part III selected from: oromandibular dystonia; cervical dystonia; arm and hand dystonia; trunk dystonia; and gait—leg dystonia; d) limb agility and coordination phenotype comprises one or more neurological manifestation of Wilson Disease according to the Unified Wilson Disease Rating Scale (UWDRS) part III selected from: finger taps; rapid alternate hand movements; handwriting; finger-to-nose test; and leg agility; e) rigidity phenotype comprises one or more neurological manifestation of Wilson Disease according to the Unified Wilson Disease Rating Scale (UWDRS) part III selected from arms, legs, and neck.

In still further embodiments, the a) total tremor phenotype is characterized by a UWDRS part III score of 30-45; b) total gait phenotype is characterized by a UWDRS part III score of 20-32; c) dystonia phenotype is characterized by a UWDRS part III score of 15-28; d) limb agility and coordination phenotype is characterized by a UWDRS part III score of 20-36; and e) rigidity phenotype is characterized by a UWDRS part III score of 10-20.

In particular embodiments, the disclosure relates to the above methods of treating Wilson Disease comprising administering bis-choline tetrathiomolybdate to patients with Wilson Disease and modifying bis-choline tetrathiomolybdate to patients with Wilson Disease, wherein the patient exhibits a neurological manifestation of Wilson Disease according to the Unified Wilson Disease Rating Scale (UWDRS) part III selected from handwriting, leg agility, and a combination thereof. In further embodiments, the patient exhibits a score for handwriting according to the UWDRS part III of 2-4; a score for leg agility according to the UWDRS part III of 2-8; or a score for handwriting and leg agility according to the UWDRS part III of 4-12. In still further embodiments, the patient exhibits an improvement in the one or more neurological manifestation of Wilson Disease according to the UWDRS part III following administration of the composition. In yet further embodiments the patient exhibits a reduction in the UWDRS part III score of one or more of: a) 5-25 for total tremor phenotype; b) 5-20 for total gait phenotype; c) 5-15 for dystonia phenotype; d) 5-20 for limb agility and coordination phenotype; and e) 5-15 for rigidity phenotype.

In yet other embodiments, the patient exhibits one or more of a reduction in the UWDRS part III score for handwriting of 1-3; a reduction in the UWDRS part III score for leg agility of 1-6; and a reduction in the UWDRS part III score for handwriting and leg agility of 2-9.

In particular embodiments, the disclosure provides a composition as described herein for use in treating Wilson Disease wherein the patient exhibits one or more phenotype of Wilson Disease selected from total tremor; total gait; dystonia; limb agility and coordination; and rigidity; preferably wherein the patient exhibits total tremor or limb agility and coordination or both. In further embodiments, the a) total tremor phenotype comprises one or more neurological manifestation of Wilson Disease according to the Unified Wilson Disease Rating Scale (UWDRS) part III selected from: resting tremor; head tremor; arms—postural tremor and wing-beating tremor; postural tremor—legs; and jaw tremor; b) total gait phenotype comprises one or more neurological manifestation of Wilson Disease according to the Unified Wilson Disease Rating Scale (UWDRS) part III selected from: arising from chair; posture—trunk dystonia, ataxia of stance, and parkinsonism; gait—leg dystonia, ataxia, and parkinsonism; c) dystonia phenotype comprises one or more neurological manifestation of Wilson Disease according to the Unified Wilson Disease Rating Scale (UWDRS) part III selected from: oromandibular dystonia; cervical dystonia; arm and hand dystonia; trunk dystonia; and gait—leg dystonia; d) limb agility and coordination phenotype comprises one or more neurological manifestation of Wilson Disease according to the Unified Wilson Disease Rating Scale (UWDRS) part III selected from: finger taps; rapid alternate hand movements; handwriting; finger-to-nose test; and leg agility; e) rigidity phenotype comprises one or more neurological manifestation of Wilson Disease according to the Unified Wilson Disease Rating Scale (UWDRS) part III selected from arms, legs, and neck.

In still further embodiments, the a) total tremor phenotype is characterized by a UWDRS part III score of 30-45; b) total gait phenotype is characterized by a UWDRS part III score of 20-32; c) dystonia phenotype is characterized by a UWDRS part III score of 15-28; d) limb agility and coordination phenotype is characterized by a UWDRS part III score of 20-36; and e) rigidity phenotype is characterized by a UWDRS part III score of 10-20.

In particular embodiments, the disclosure provides a composition as described herein for use in treating Wilson Disease wherein the patient exhibits a neurological manifestation of Wilson Disease according to the Unified Wilson Disease Rating Scale (UWDRS) part III selected from handwriting, leg agility, and a combination thereof. In further embodiments, the patient exhibits a score for handwriting according to the UWDRS part III of 2-4; a score for leg agility according to the UWDRS part III of 2-8; or a score for handwriting and leg agility according to the UWDRS part III of 4-12. In still further embodiments, the patient exhibits an improvement in the one or more neurological manifestation of Wilson Disease according to the UWDRS part III following administration of the composition. In yet further embodiments the patient exhibits a reduction in the UWDRS part III score of one or more of: a) 5-25 for total tremor phenotype; b) 5-20 for total gait phenotype; c) 5-15 for dystonia phenotype; d) 5-20 for limb agility and coordination phenotype; and e) 5-15 for rigidity phenotype.

In yet other embodiments, the patient exhibits one or more of a reduction in the UWDRS part III score for handwriting of 1-3; a reduction in the UWDRS part III score for leg agility of 1-6; and a reduction in the UWDRS part III score for handwriting and leg agility of 2-9.

In particular embodiments, the disclosure provides a composition as described herein for use in treating Wilson Disease wherein the patient has cirrhosis In particular embodiments, the disclosure provides a composition as described herein for use in treating Wilson Disease wherein the patient does not have cirrhosis.

Additional aspects and embodiments will be apparent from the detailed description that follows.

BRIEF DESCRIPTION OF THE D WINGS

FIG. 1 depicts the Trial Profile.

FIG. 2 depicts Changes in $NCC_{corrected}$ concentrations over time. Changes from baseline are least-squares mean (SE) for between 19 and 25 patients at each timepoint. One patient discontinued treatment at week 23, but within the specified window for inclusion of the $NCC_{corrected}$ measurement as a value for week 24. p-values are versus baseline.

FIG. 3 depicts changes in disability and neurological status over time. Changes from baseline Unified Wilson's Disease Rating Scale (UWDRS part II) scores (disability; A) and part III scores (neurological signs; B) are least-squares mean (SE) for between 21 and 28 patients.

Figure 10A:
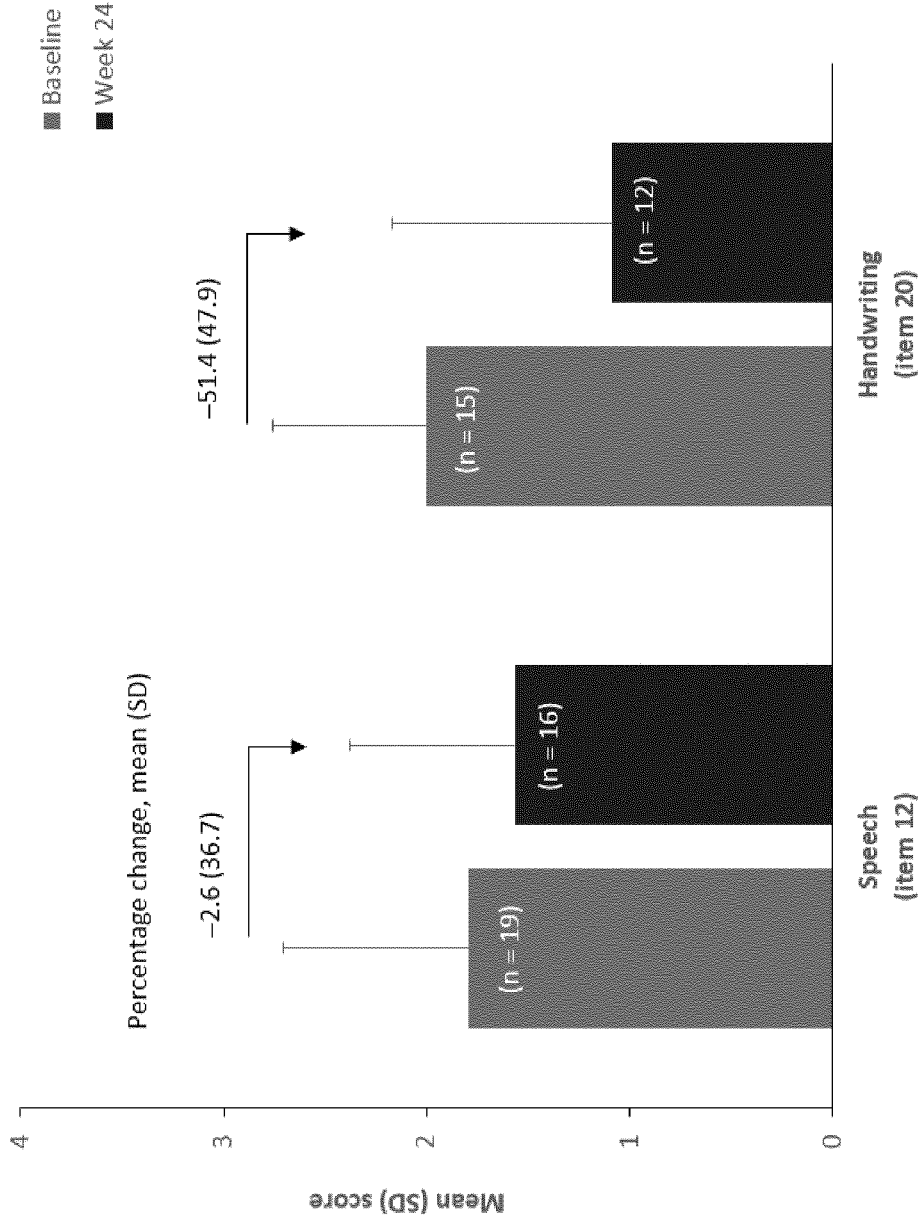
Figure 10B:
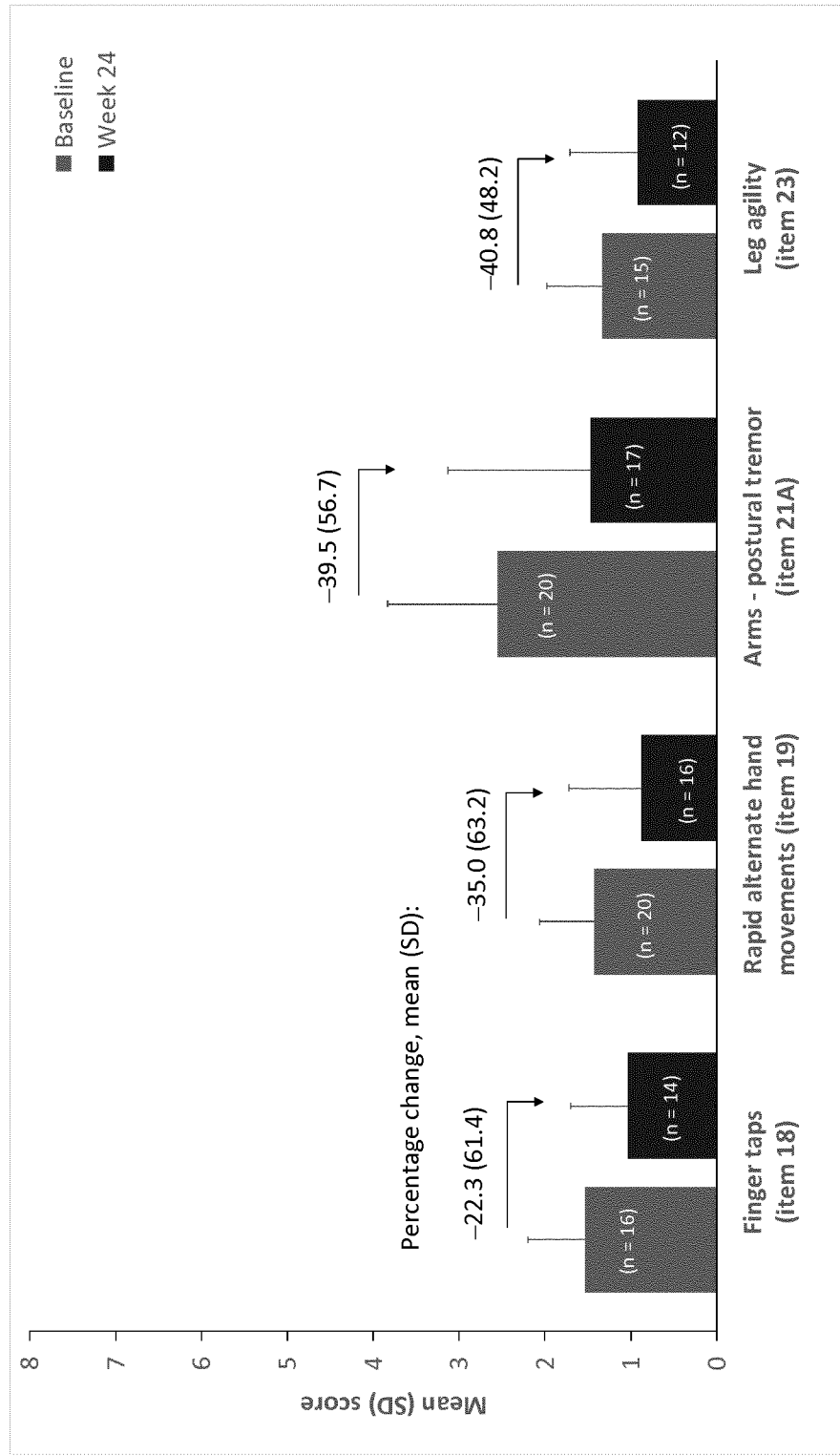

FIGS. 10A-10B depict UWDRS neurological status (part III) item scores for the study population. FIG. 10A shows items with a maximum score of 4. FIG. 10A shows items with a maximum score of 8.

Figure 11A:
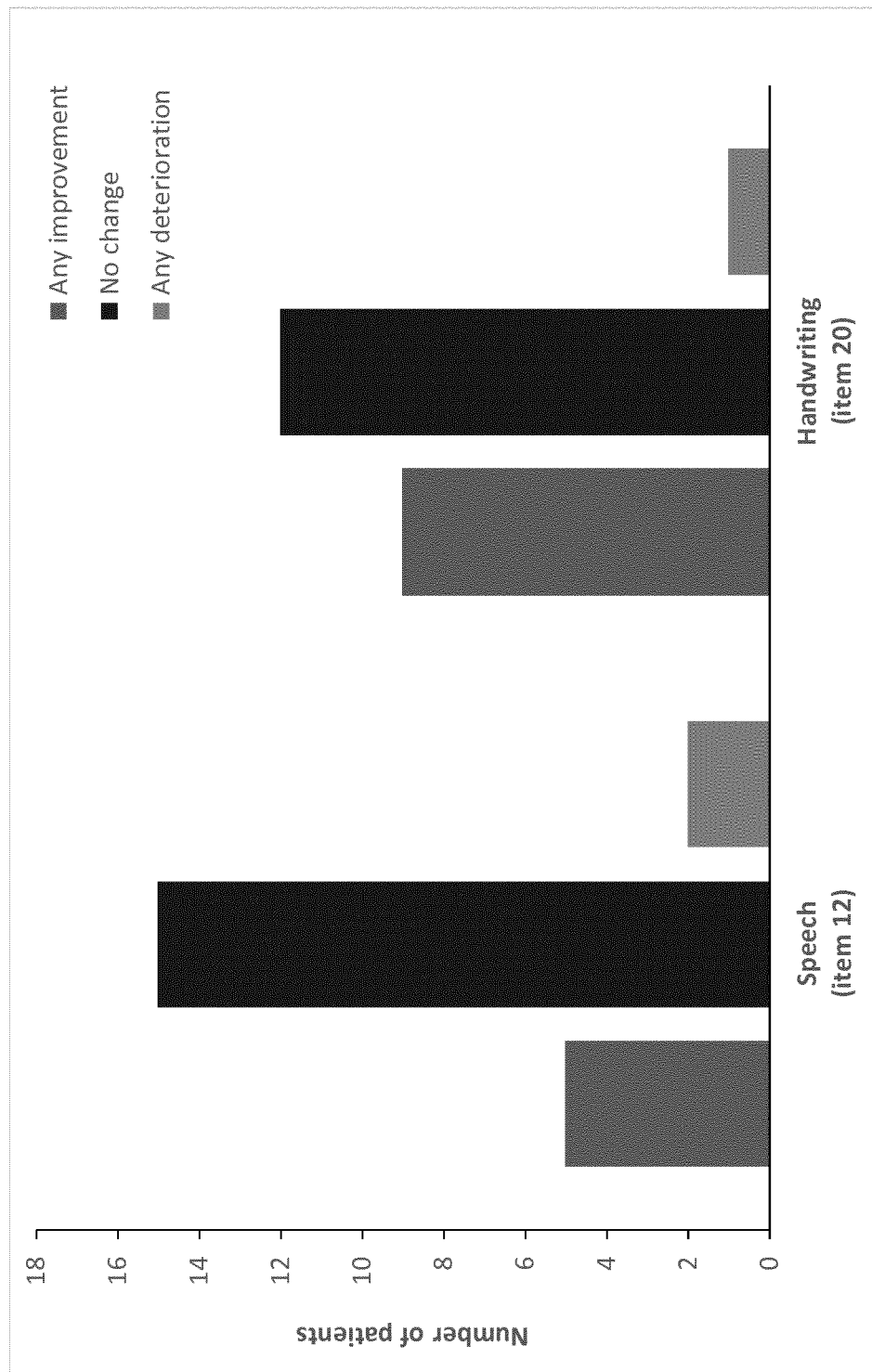
Figure 11B:
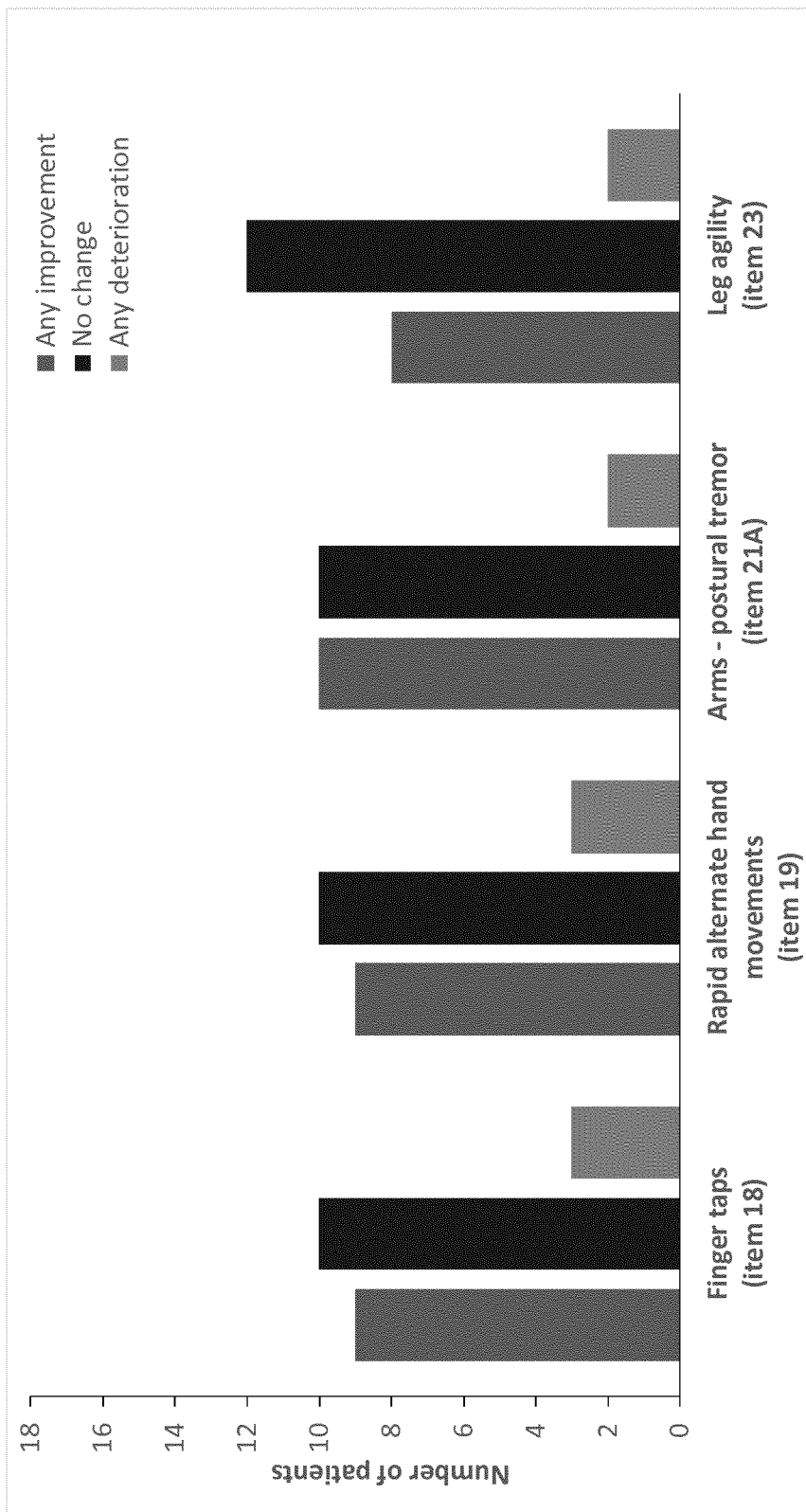

FIGS. 11A-11B depict numbers of patients with changes in UWDRS neurological status (part III) item scores between baseline and week 24. Data are from all patients with data for the given item, including those with zero scores at baseline (n=22 in each case). FIG. 11A shows items with a maximum score of 4. FIG. 11B shows items with a maximum score of 8.

Figure 12:
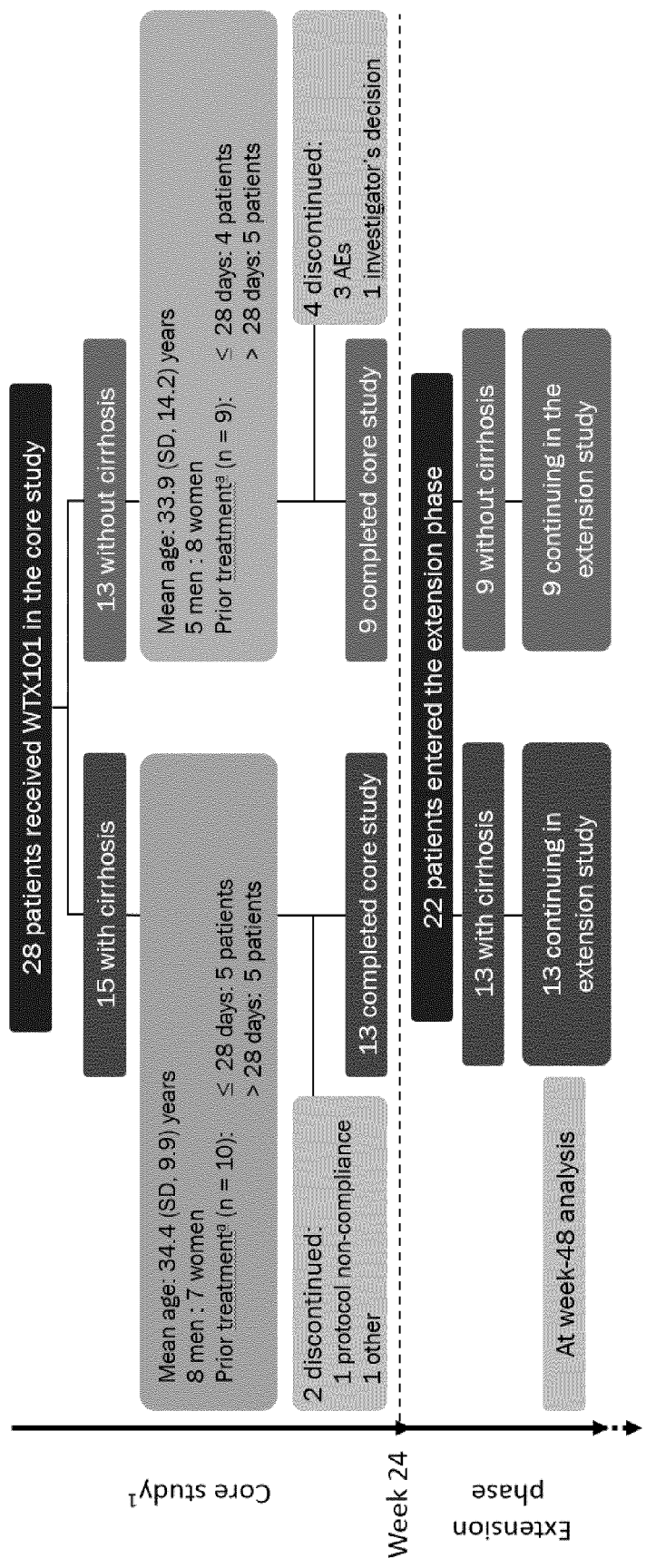

FIG. 12 depicts patient flow for the extension study.

Figure 13:
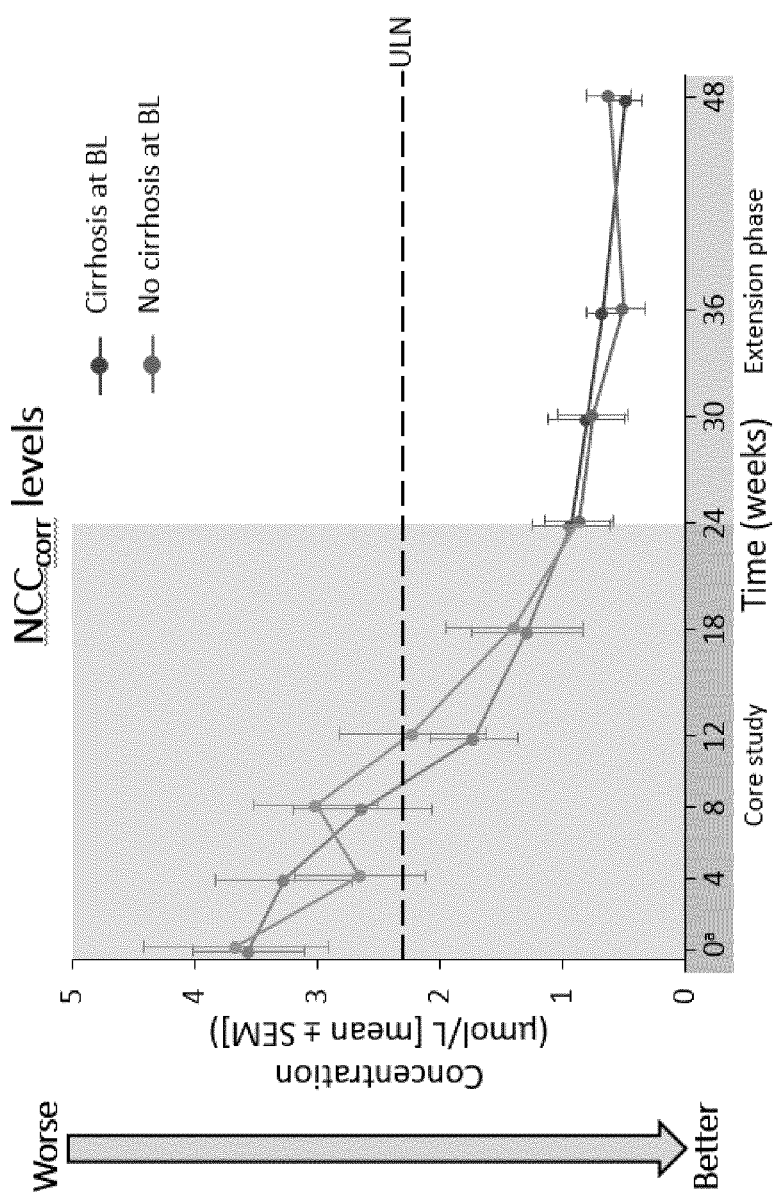

FIG. 13 depicts $NCC_{corr}$ levels for patients with and without cirrhosis. NCC levels were not corrected at baseline, as no WTX101 had been received. BL, baseline; LLN, lower limit of normal reference range (0.8 µmol/L); ULN, upper limit of normal reference range (2.3 µmol/L); $NCC_{corr}$, non-ceruloplasmin bound copper corrected for the amount of copper bound in the tetrathiomolybdate-copper-albumin complex; SEM, standard error of the mean.

Figure 14:
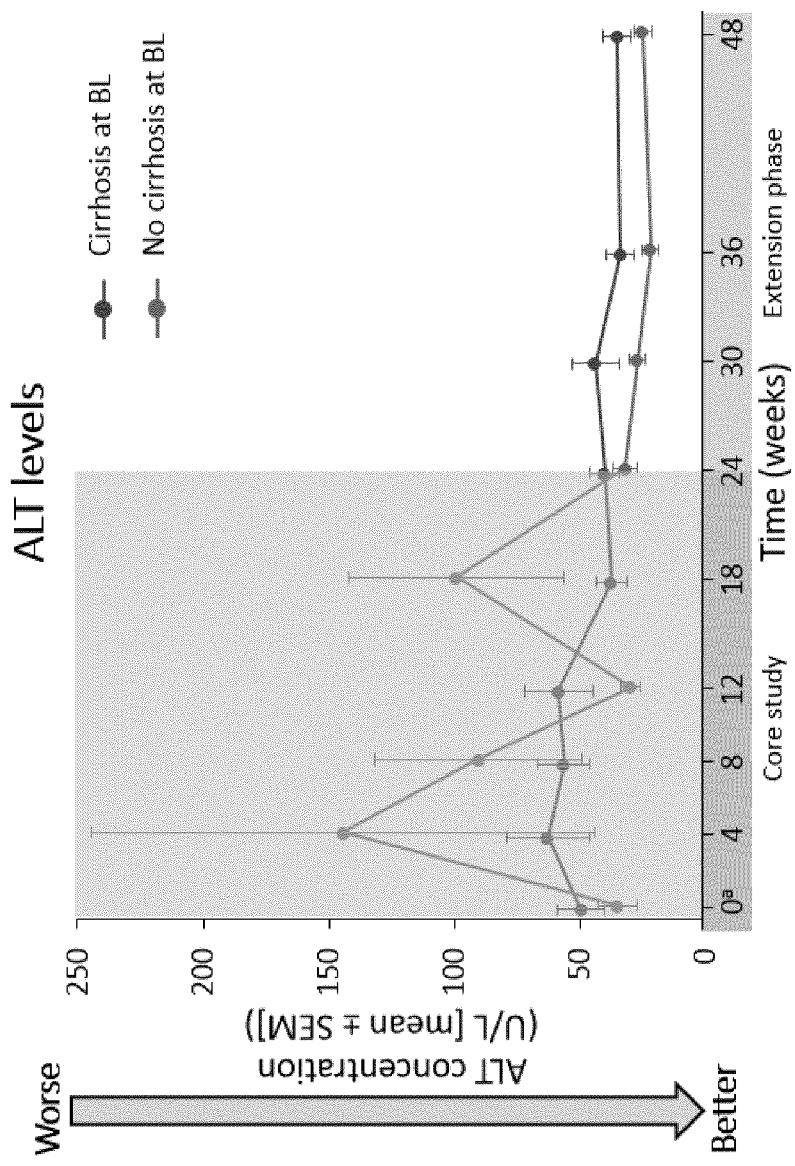
Figure 15:
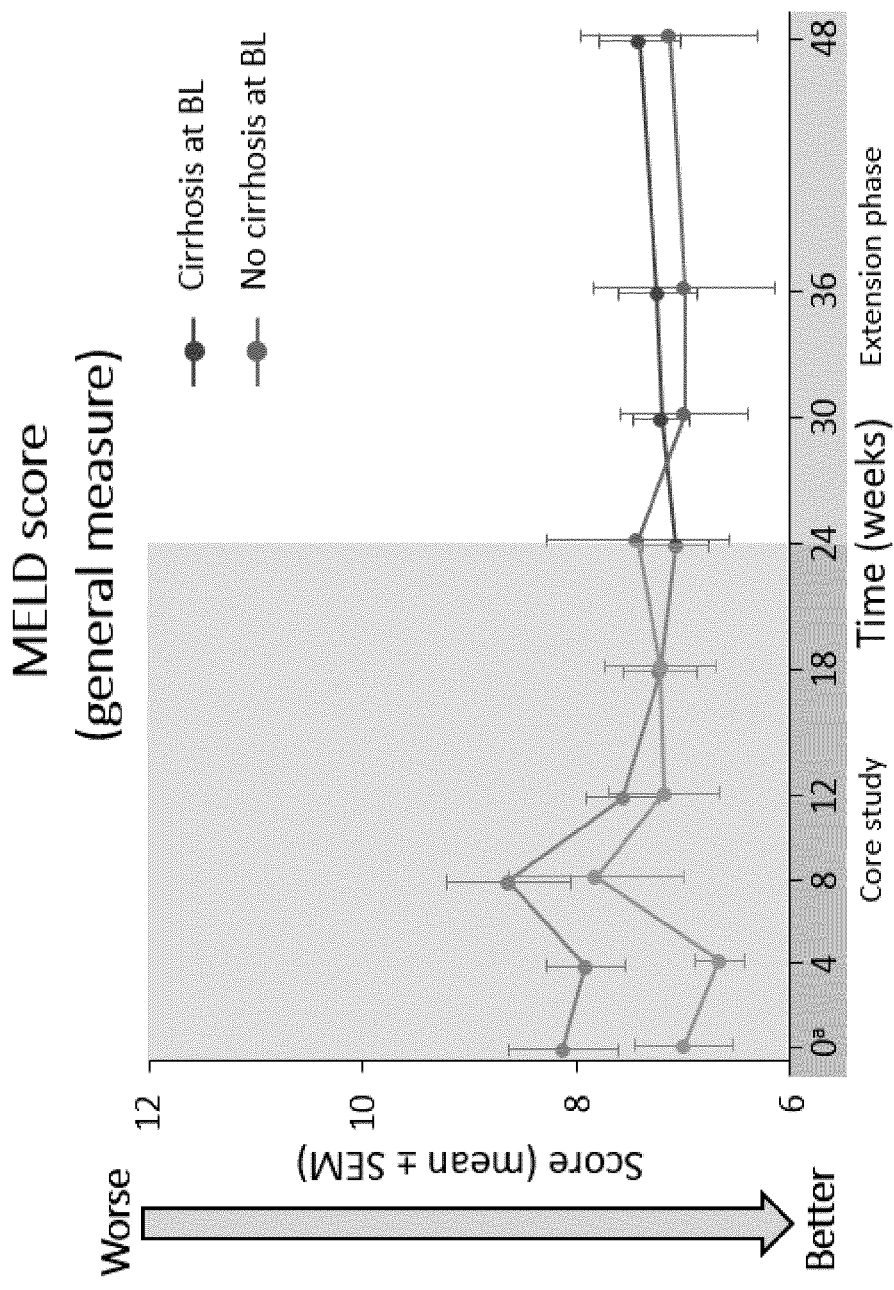
Figure 16:
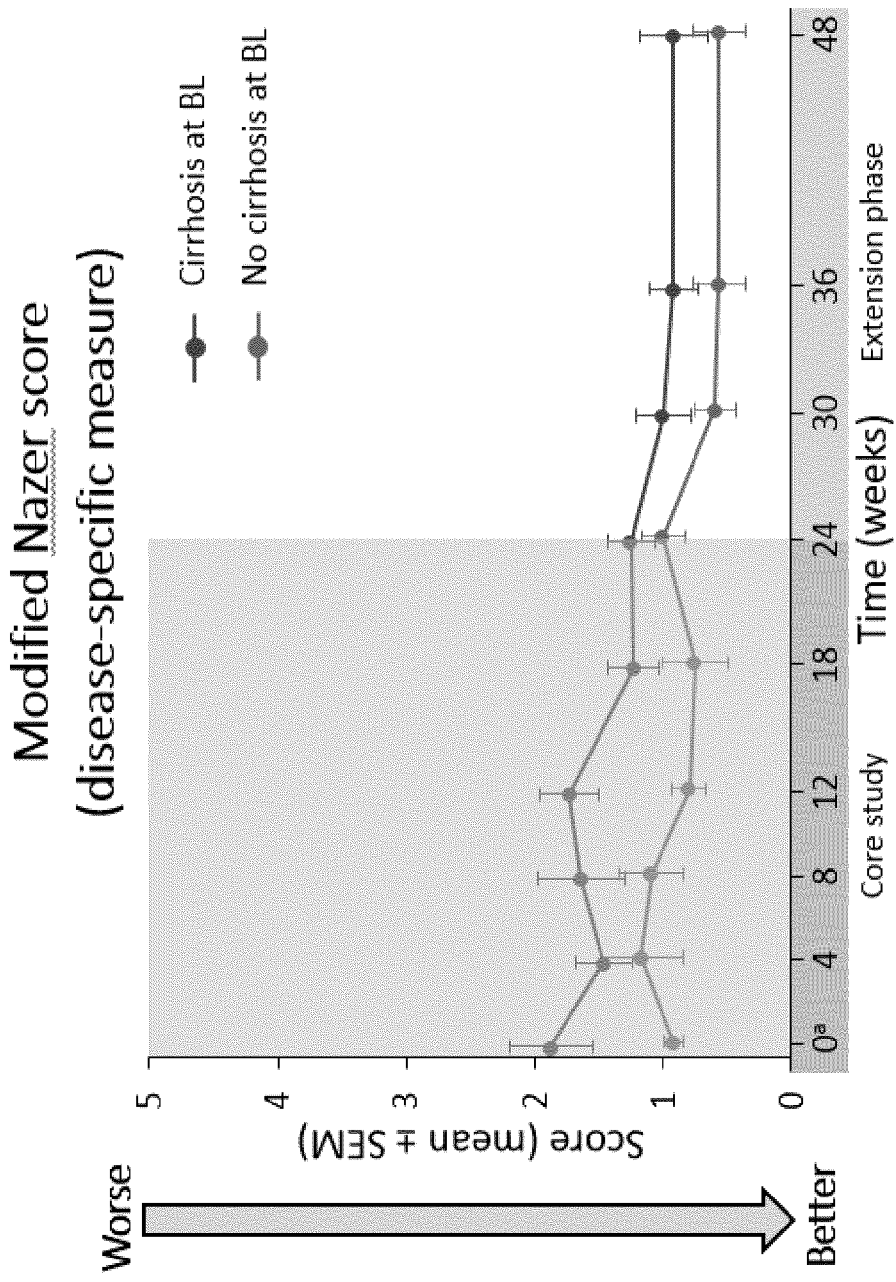

FIG. 14 depicts ALT levels for patients with and without cirrhosis. ALT, alanine aminotransferase; BL, baseline; SEM, standard error of the mean FIG. 15 depicts MELD score (liver disease severity; score range, 6-40) for patients with and without cirrhosis. BL, baseline; MELD, model for end-stage liver disease; SEM, standard error of the mean FIG. 16 depicts modified Nazer score (prognostic index; score range, 0-20) for patients with and without cirrhosis.

Figure 17A:
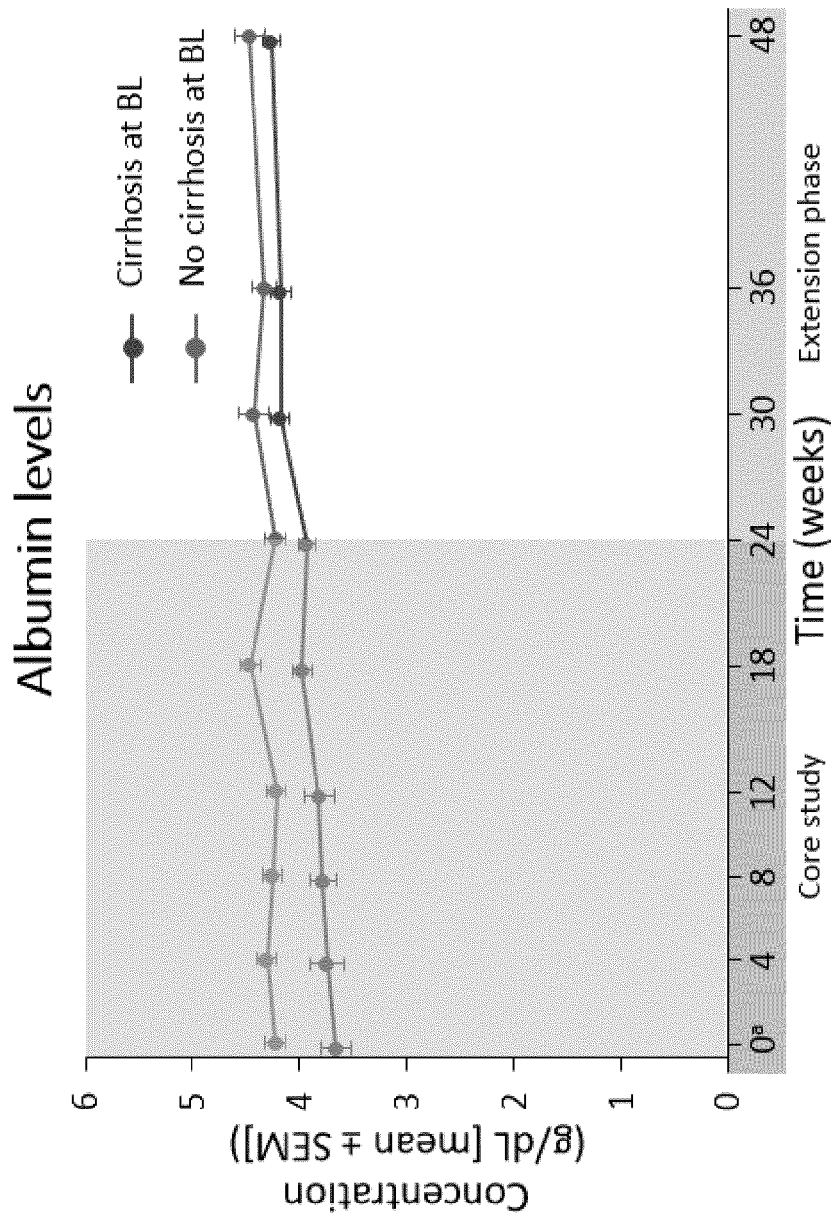
Figure 17B:
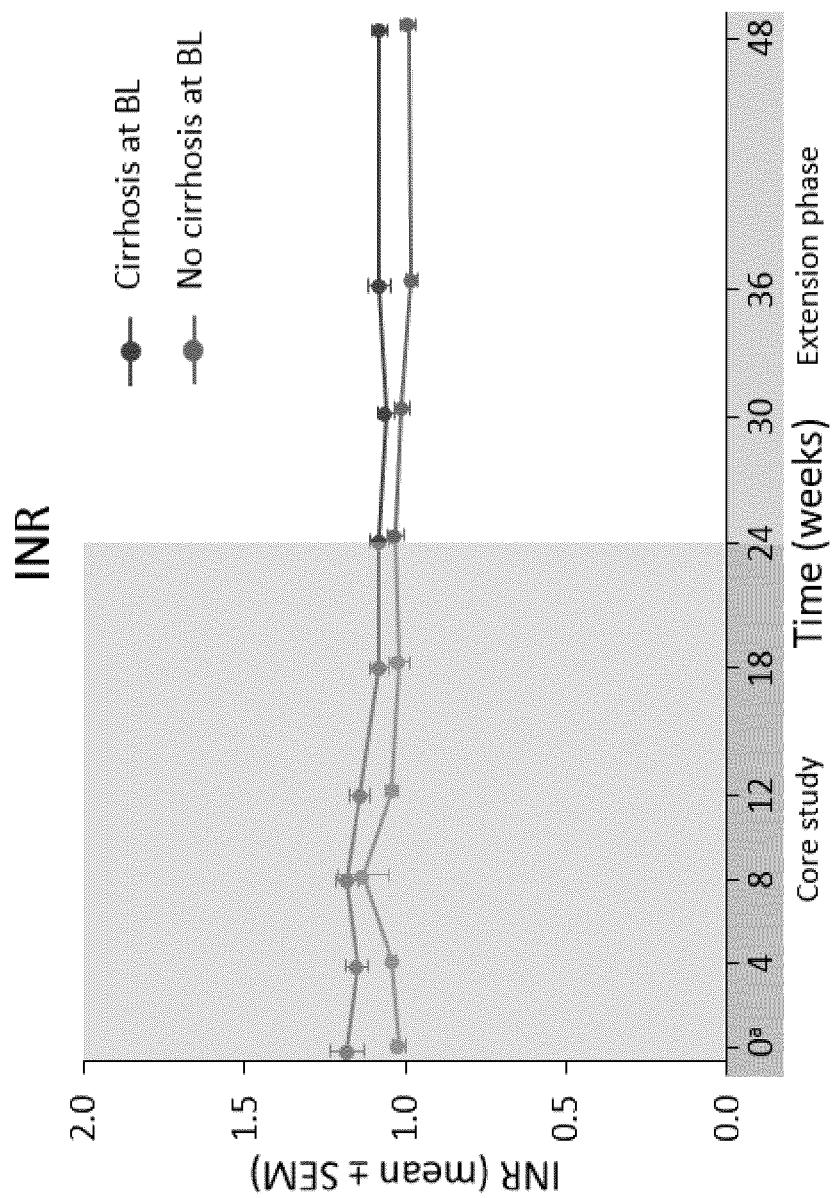
Figure 18:
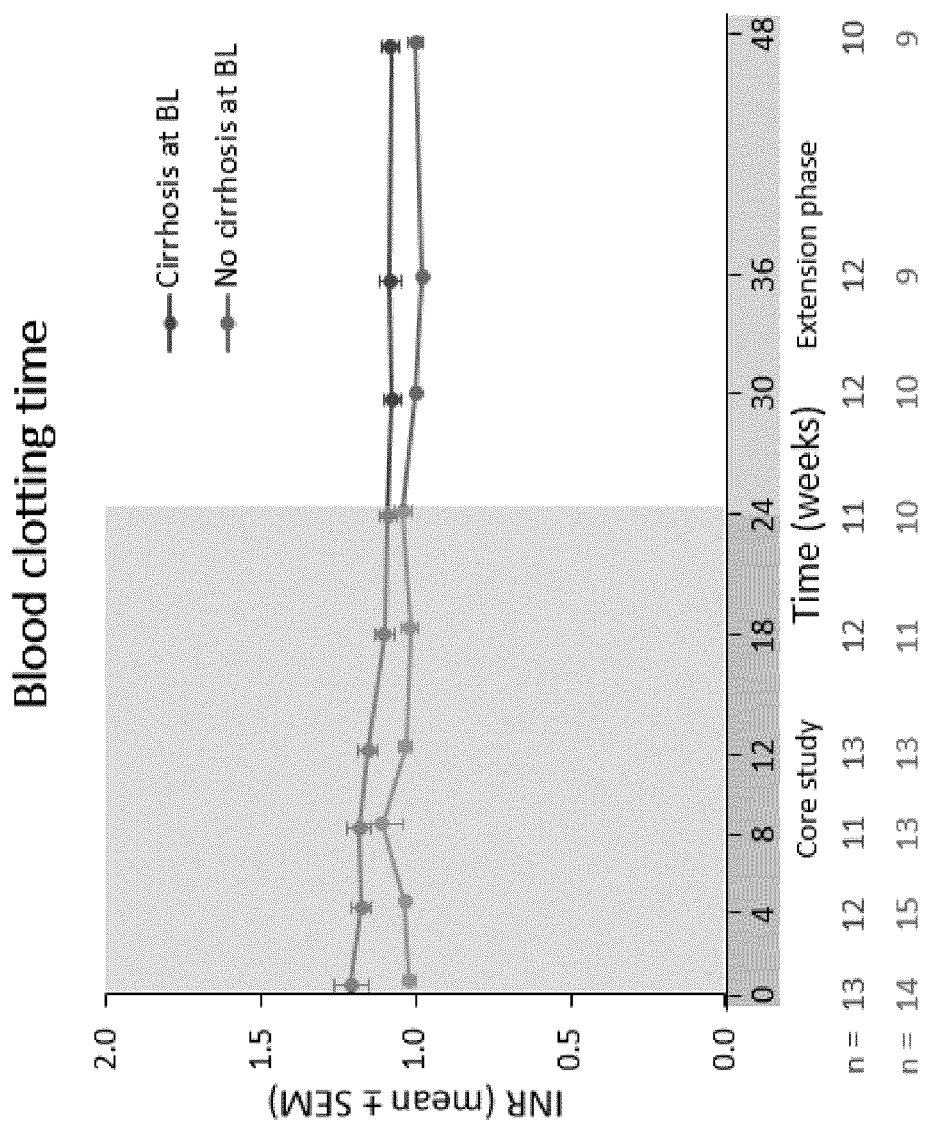
Figure 19A:
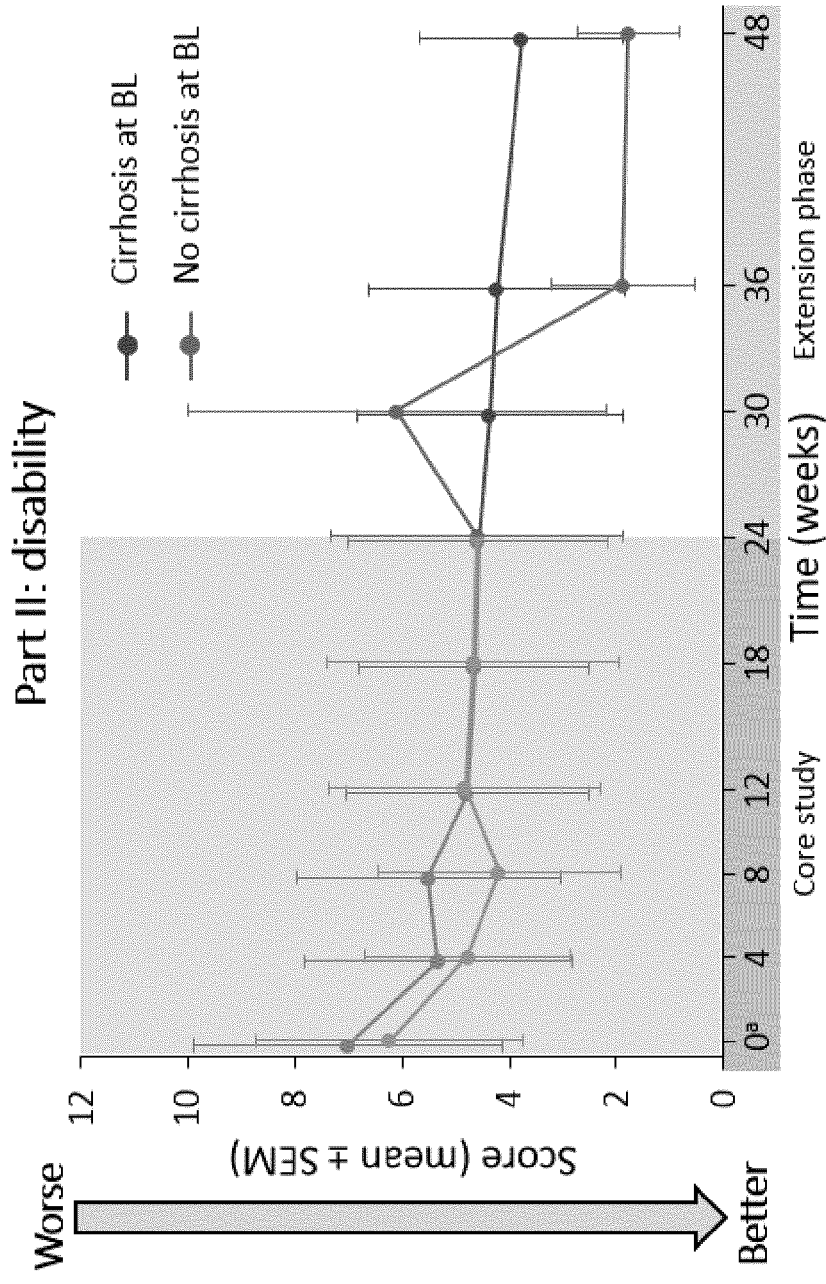
Figure 19B:
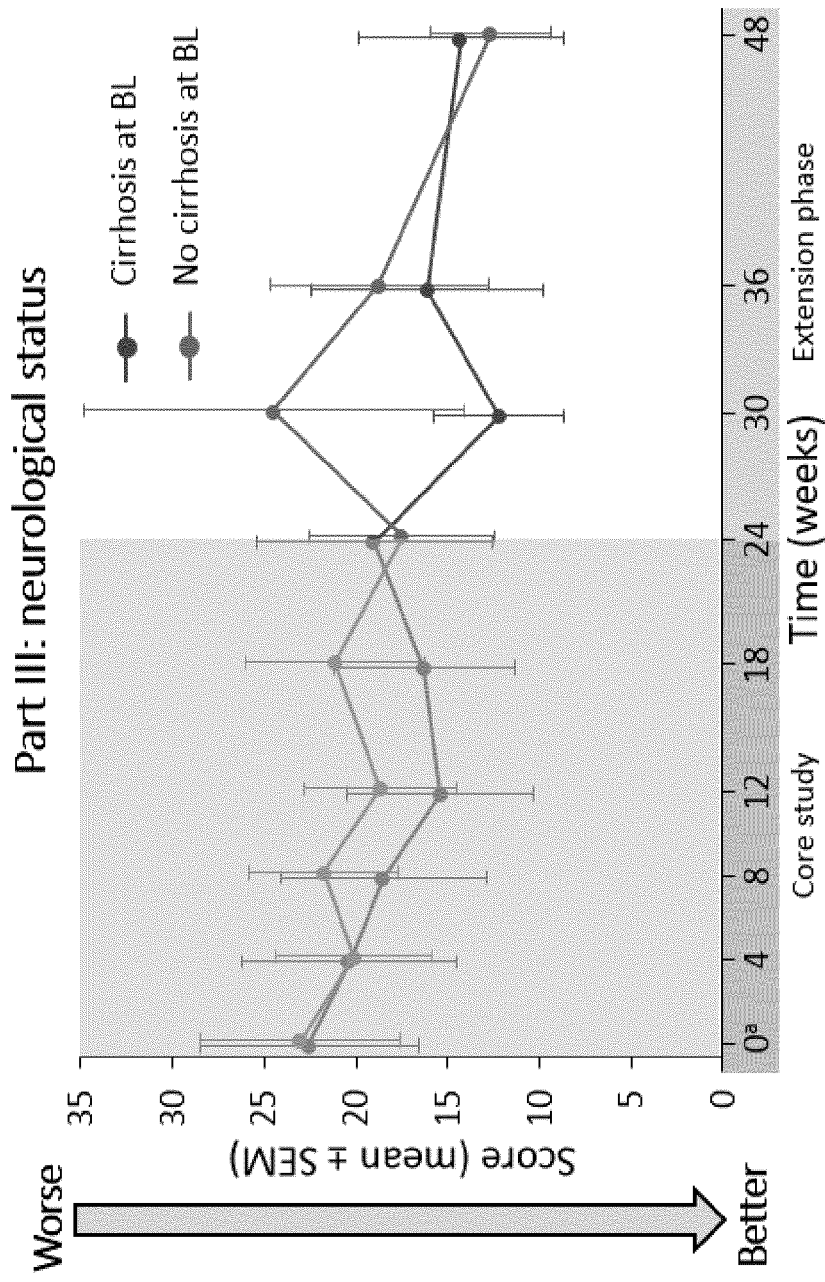

FIG. 17A depicts albumin levels for patients with and without cirrhosis. FIG. 17B depicts international normalized ratio for patients with and without cirrhosis. BL, baseline; INR, international normalized ratio; SEM, standard error of the mean FIG. 18 depicts blood clotting time for patients with and without cirrhosis. BL, baseline; INR, international normalized ratio; SEM, standard error of the mean FIGS. 19A-19B depict UWDRS for part II (measures disability based on patient-reported activities of daily living; score range, 0-40) (FIG. 19A) and part III (measures neurological status as assessed by a clinician (score range; 0-143) (FIG. 19B). Higher scores indicate worse condition.

DETAILED DESCRIPTION

Certain aspects of the present disclosure are based on the surprising discovery that one may reduce adverse events associated with treatment of Wilson Disease by administering a 15 mg dosage form of bis-choline tetrathiomolybdate or by modifying a daily dose of bis-choline tetrathiomolybdate in order to control abnormal liver function in the patient. The ammonium salt of tetrathiomolybdate is generally administered in larger dosages, e.g., 90 to 220 mg per day. Brewer et al. Initial Therapy of Patients with Wilson's Disease with Tetrathiomolybdate. Arch. Neurol. 48:42-47 (1991). According to the present disclosure, administration of bis-choline tetrathiomolybdate at the same, or similar, dosages to dosages of ammonium tetrathiomolybdate generally known in the art is associated with adverse events which the methods of the present disclosure reduce.

The disclosure provides methods for administering a therapeutically effective dose of bis-choline tetrathiomolybdate to a patient that has exhibited abnormal test results after the patient has been treated with bis-choline tetrathiomolybdate. Because liver function abnormalities can be indicative of drug-induced liver injury (hepatotoxicity), it is important to determine whether the abnormalities reflect liver injury or merely indicate limited toxicity that will resolve over time while continuing to take the drug. According to the present disclosure, even patients that exhibit abnormal liver function may continue taking bis-choline tetrathiomolybdate at the same dose, or continue taking the bis-choline tetrathiomolybdate at a reduced dose, optionally after discontinuing bis-choline tetrathiomolybdate for a period of time. This administration regimen has the advantage of maximizing the time on the full target dose of drug and therefore the potential for a beneficial therapeutic effect.

The methods of the disclosure optionally include identifying abnormal liver function in a patient receiving bis-choline tetrathiomolybdate, and monitoring liver test results in a patient receiving a reduced dose of bis-choline tetrathiomolybdate. In any of the methods described herein, ALT may be elevated, e.g. to a level greater than 34 IU/mL or 64 IU/mL or 170 IU/mL prior to dose reduction. Alternatively, hemoglobin may be decreased, or platelets may be decreased, or neutrophils may be decreased prior to dose reduction.

The methods of the disclosure optionally include measuring copper levels in the body. Various means of measuring copper levels in the body are known in the art. In one embodiment, free copper concentrations in serum or plasma ultrafiltrate is measured by inductively coupled mass spectrometry to assist with diagnosis and monitoring Wilson Disease. In another embodiment, the free concentration in urine is determined. In another embodiment, biliary secretion of copper is determined by measurement of copper concentration in feces. In another embodiment, the copper content of hair is determined. In a further embodiment, the amount of free serum copper is determined as the amount of unbound copper circulating in the blood, which is copper unbound by Ceruloplasmin. It will be understood that this is the copper that is free to accumulate in the liver and other organs. In a preferred embodiment, Non-Ceruloplasmin-Bound Copper or NCC is determined by inductively coupled mass spectrometry or other methods known in the art. In any of the methods described herein, $NCC_{corrected}$ may be elevated, e.g. greater than 2.3 μm/L.

While the ranges for the above-referenced test-results and levels in healthy individuals can vary depending on the testing conditions and lab methodology, it is generally known that healthy individuals, exhibit the following: ALT levels in the range of 6-34 U/L, 9-34 U/L, or 6-41 U/L; hemoglobin in the range of 11.6-16.4 g/dL, 13.6-18.0 g/dL, or 12.0-16.0 g/dL; platelets in the range of 140-400×$10^3$/μL; neutrophils in the range of 1.96-7.23×$10^3$/μL; and bilirubin in the range of 0.2-1.2 mg/dL or 0.10-1.10 mg/dL. Further information on the clinical laboratory methods for diagnosis and treatment of Wilson's Disease is provided in the European Association for the Study of the Liver (EASL) Clinical Practice Guidelines: Wilson's Disease; *J. Hepatology* 56:671-685 (2012), which is incorporated into this disclosure in its entirety.

In some embodiments the disclosure relates to methods of treating Wilson Disease in a patient by administering 15 mg of bis-choline tetrathiomolybdate once daily or once every day. The once daily dose may be given in the form of a single dose, or two doses, optionally two doses divided equally, or three or four or five doses. The dose may be delivered oral, intravenously, intramuscularly or in any other manner known in the art.

In some embodiments the disclosure relates to methods of treating Wilson Disease in a patient by administering from 30 to 90 mg of bis-choline tetrathiomolybdate daily, where the patient has one or more of the following: an $NCC_{corrected}$ greater than 2.3 μm/L, alanine aminotransferase (ALT) level less than 80 IU/mL, hemoglobin of greater than 8 g/dL, platelets greater than 30,000/4, or neutrophils greater than 1,000/μL or 1×$10^3$/μL. The patient may have $NCC_{corrected}$ greater than 2.3 μm/L and alanine aminotransferase (ALT) level less than 80 IU/mL, or $NCC_{corrected}$ greater than 2.3 μm/L and hemoglobin of greater than 8 g/dL, or any other combination of two or more of these parameters. In some embodiments, one or more of the parameters will be measured. In an embodiment, $NCC_{corrected}$ is measured. In another embodiment, two or more of the parameters are measured. In another embodiment, all parameters are measured.

In some embodiments the disclosure relates to methods of treating Wilson Disease in a patient by administering from 30 to 90 mg of bis-choline tetrathiomolybdate daily, where the patient has one or more of the following: an $NCC_{corrected}$ greater than 2.0, 2.1, 2.2, 2.3, 2.4, 2.5 μm/L or the upper limit of normal (ULN) of the $NCC_{corrected}$, alanine aminotransferase (ALT) level less than 50, 55, 60, 65, 70, 75, 80, 85, 90, 95, 100 IU/mL or twice the upper limit of normal (ULN) of ALT, hemoglobin of greater than 6, 7, 8, 9, or 10 g/dL, platelets greater than 20,000, 25,000, 30,000, 35,000, or 40,000/4, or neutrophils greater than 0.5×$10^3$, 1×$10^3$, 1.5×$10^3$, 2×$10^3$ or 2.5×$10^3$/μL. In certain embodiments, the patient may combination of two or more of these parameters. In some embodiments, one or more of the parameters will be measured. In another embodiment, $NCC_{corrected}$ is measured. In further embodiments, two or more of the parameters are measured. In yet further embodiments, all are measured.

In some embodiments the disclosure relates to methods of modifying bis-choline tetrathiomolybdate administration to a patient with Wilson Disease undergoing bis-choline tetrathiomolybdate treatment by increasing the daily dose of bis-choline tetrathiomolybdate. In some embodiments of the disclosure, the dose of bis-choline tetrathiomolybdate is increased in a patient exhibiting certain test results. In some embodiments, the daily dose of bis-choline tetrathiomolybdate is increased in increments of 15 mg. In some embodiments the disclosure the daily dose is increased when the patient has one or more of the following: an $NCC_{corrected}$ greater than 2.3 μm/L, alanine aminotransferase (ALT) level less than 80 IU/mL, hemoglobin of greater than 8 g/dL, platelets greater than 30,000/4, or neutrophils greater than 1,000/4 or 1×$10^3$/μL. In further embodiments, the dose is increased when the patient has one or more of the following: an $NCC_{corrected}$ greater than 2.0, 2.1, 2.2, 2.3, 2.4, 2.5 μm/L or the upper limit of normal (ULN) of the $NCC_{corrected}$, alanine aminotransferase (ALT) level less than 50, 55, 60, 65, 70, 75, 80, 85, 90, 95, 100 IU/mL or twice the upper limit of normal (ULN) of ALT, hemoglobin of greater than 6, 7, 8, 9, or 10 g/dL, platelets greater than 20,000, 25,000, 30,000, 35,000, or 40,000/4, or neutrophils greater than 0.5×$10^3$, 1×$10^3$, 1.5×$10^3$, 2×$10^3$, or 2.5×$10^3$/μL. The patient may have $NCC_{corrected}$ greater than 2.3 μm/L and alanine aminotransferase (ALT) level less than 80 IU/mL, or $NCC_{corrected}$ greater than 2.3 μm/L and hemoglobin of greater than 8 g/dL, or any other combination of two or more of these parameters. In some embodiments, one or more of the parameters will be measured. In an embodiment, $NCC_{corrected}$ is measured. In another embodiment, two or more of the parameters are measured. In another embodiment, all parameters are measured. In certain embodiments, the daily dose is increased by increments of 15 mg of bis-choline tetrathiomolybdate. In particular embodiments, the daily dose is increased during treatment initiation, typically the first 3, 4, 5, or 6 months of treatment with bis-choline tetrathiomolybdate. In certain aspects of the disclosure, a patient's dose is increased once. In further aspects of the disclosure, a patient's dose is increased twice. In still further aspects of the disclosure, a patient's dose is increased three or more times.

In some embodiments the disclosure relates to methods of modifying bis-choline tetrathiomolybdate administration to a patient with Wilson Disease undergoing bis-choline tetrathiomolybdate treatment by decreasing the daily dose of bis-choline tetrathiomolybdate. In some embodiments, the daily dose of bis-choline tetrathiomolybdate is decreased in increments of 15 mg. In one embodiment, the daily dose is decreased by administering the dose every other day. In another embodiment, the daily dose is decreased by administering 15 mg every other day so that the patient receives on average 7.5 mg of bis-choline tetrathiomolybdate per day.

In one aspect, the present disclosure further provides methods for decreasing the daily dose of bis-choline tetrathiomolybdate in a patient exhibiting an abnormal test result. In certain aspects of the disclosure, administration of bis-choline tetrathiomolybdate is temporarily interrupted when a patient exhibits certain abnormal test results, and resumed, optionally at a lower dose, when the patent exhibits improved test results. In one embodiment the test is a test of liver function. Any of the tests of liver function known in the art may be employed. In an embodiment, alanine aminotransferase (ALT) or bilirubin levels are used. In one embodiment the test is a test of bone marrow suppression caused by long-term over-decoppering leading to cytopenia. In an embodiment, hemoglobin level, platelet level, or neutrophils level may be used as the test. In an embodiment, two or more tests test results are used. In an embodiment, several tests are used. In particular embodiments, the dose is reduced when two consecutive test results are abnormal.

In certain embodiments, the daily dose of bis-choline tetrathiomolybdate in a patient exhibiting an abnormal test result is decreased by 15 mg, such that the dose of a patient taking 15 mg of bis-choline tetrathiomolybdate daily prior to the abnormal test result would be decreased to 15 mg of bis-choline tetrathiomolybdate every other day, the dose of a patient taking 30 mg of bis-choline tetrathiomolybdate daily prior to the abnormal test result would be decreased to 15 mg daily, the dose of a patient taking 45 mg of bis-choline tetrathiomolybdate daily prior to the abnormal test result would be decreased to 30 mg daily, the dose of a patient taking 60 mg of bis-choline tetrathiomolybdate daily prior to the abnormal test result would be decreased to 45 mg daily, the dose of a patient taking 75 mg of bis-choline tetrathiomolybdate daily prior to the abnormal test result would be decreased to 60 mg daily, and the dose of a patient taking 90 mg of bis-choline tetrathiomolybdate daily prior to the abnormal test result would be decreased to 75 mg daily. In other embodiments, the daily dose of bis-choline tetrathiomolybdate in a patient exhibiting an abnormal test result is decreased by half. In still other embodiments, the dose of bis-choline tetrathiomolybdate in a patient exhibiting an abnormal test result taking 30-90 mg of bis-choline tetrathiomolybdate daily prior to the abnormal test result is reduced to a daily 15 mg dose of bis-choline tetrathiomolybdate, and the dose of bis-choline tetrathiomolybdate in a patient exhibiting an abnormal test result taking 15 mg of bis-choline tetrathiomolybdate daily prior to the abnormal test result is reduced to a dose of 15 mg of bis-choline tetrathiomolybdate every other day.

In particular embodiments, administration of bis-choline tetrathiomolybdate is temporarily interrupted when a patient exhibits certain abnormal test results and resumed when test results meet a particular threshold. In certain embodiments dosing is interrupted when two consecutive test results are abnormal. In further embodiments, dosing is resumed when two consecutive test results meet a particular threshold. In certain embodiments, the daily dose of bis-choline tetrathiomolybdate is resumed at the level prior to interruption. In further embodiments, the daily dose of bis-choline tetrathiomolybdate is resumed at decreased dosage level as described above. In yet further embodiments of the disclosure, the daily dose is resumed at 15 mg of bis-choline tetrathiomolybdate. In still further embodiments of the disclosure, the daily dose is resumed at 15 mg of bis-choline tetrathiomolybdate if the patient was taking 30-90 mg of bis-choline tetrathiomolybdate daily prior to the abnormal test result. In even further embodiments of the disclosure, the dose is resumed at 15 mg of bis-choline tetrathiomolybdate every other day if the patient was taking 15 mg of bis-choline tetrathiomolybdate daily prior to the abnormal test result.

An abnormal test result may be defined in terms of a set threshold above or below which liver function or bone marrow function is said to be normal. In an optional aspect, an Upper Limit of Normal (ULN) is defined for a test result. In an optional aspect, dosing is modified when a patient exhibits two consecutive abnormal test results. Administration of bis-choline tetrathiomolybdate may be modified due to a test result greater than the ULN, or twice the ULN, or three times the ULN, or four times the ULN, or five times the ULN, or any multiple of the ULN, or due to a test of liver function greater than any fractional multiple of ULN between one, two, three, four, or five times the ULN. In an embodiment, daily administration of bis-choline tetrathiomolybdate is reduced when the test result is two to five times the ULN. In an embodiment, daily administration of bis-choline tetrathiomolybdate is discontinued when the test result is greater than five times the ULN. In another embodiment, the test of liver function is ALT. Optionally, administration of bis-choline tetrathiomolybdate is resumed when ALT is less than twice the ULN. Optionally, the daily dose of bis-choline tetrathiomolybdate is resumed at a lower dosage when ALT is less than twice ULN. In one embodiment, the ULN and lower limit of normal (LLN) of ALT are depend on the particular assay used. In one embodiment, the ULN of ALT is 30-45 IU/mL or 30-33 IU/mL or 33-36 IU/mL or 36-39 IU/mL or 39-42 IU/mL or 42-45 IU/mL. In an embodiment, the ULN of ALT is 30, 31, 32, 33, 34, 35, 36, 37, 38, 39, 40, 41, 42, 43, 44, or 45 IU/mL, or any fractional number in between. In another embodiment, the ULN of ALT is 34 IU/mL. In another embodiment, the ULN of ALT is 40 IU/mL.

In another optional aspect, the daily dose of bis-choline tetrathiomolybdate is modified when a liver result decreases below a baseline measurement of the test taken before administration of bis-choline tetrathiomolybdate begins. Optionally, this baseline is patient specific. Optionally, this baseline is determined by medical judgment. Optionally, this baseline is determined by clinical trial results. Optionally, dosing is modified when a patient exhibits two consecutive abnormal test results. In an embodiment, the threshold for modifying the dose of bis-choline tetrathiomolybdate is 50% or 60% or 70% or 80% or 90% of baseline or any percentage between. In another embodiment, the threshold is 65% or 70% or 75% of baseline. In an embodiment, the threshold is 70% of baseline. In an optional aspect, the dose of bis-choline tetrathiomolybdate is modified when the hemoglobin level of the patient is less than 70% of the baseline hemoglobin for that patient. In other optional aspect, the threshold is 70% of baseline platelets or 70% of baseline neutrophils.

In a further aspect, the dose of bis-choline tetrathiomolybdate is decreased or temporarily interrupted when the hemoglobin level of the patient is less than 6, 7, 8, 9, or 10 g/dL. In a still further aspect, the dose of bis-choline tetrathiomolybdate is decreased or temporarily interrupted when the hemoglobin level of the patient is less than 8 g/dL. In another aspect, the dose of bis-choline tetrathiomolybdate is decreased or temporarily interrupted when platelets are less than 20,000, 25,000, 30,000, 35,000, or 40,000/4. In yet another aspect, the dose of bis-choline tetrathiomolybdate is decreased or temporarily interrupted when platelets are less than 30,000/µL. In yet another aspect, the dose of bis-choline tetrathiomolybdate is decreased or temporarily interrupted when neutrophils are less than $0.5 \times 10^3$, $1 \times 10^3$, $1.5 \times 10^3$, $2 \times 10^3$ or $2.5 \times 10^3/\mu L$. In yet another aspect, the dose of bis-choline tetrathiomolybdate is decreased or temporarily interrupted when neutrophils are less than $1 \times 10^3$/pt. Optionally, dosing is modified when a patient exhibits two consecutive abnormal test results.

In particular embodiments, when the dose of bis-choline tetrathiomolybdate is temporarily interrupted, dosing is resumed when the patient exhibits one or more of the following: a hemoglobin level equal to or greater than 6, 7, 8, 9, or 10 g/dL; platelets greater or equal than 20,000, 25,000, 30,000, 35,000, or 40,000/µL; and/or neutrophils greater than or equal to $0.5 \times 10^3$, $1 \times 10^3$, $1.5 \times 10^3$, $2 \times 10^3$ or $2.5 \times 10^3/\mu L$. In further embodiments, when the dose of bis-choline tetrathiomolybdate is temporarily interrupted, dosing is resumed when the patient exhibits one or more of the following: a hemoglobin level equal to or greater than 8 g/dL; platelets greater or equal than 30,000/µL; and/or neutrophils greater than or equal to 1×10³/μL. In further embodiments, when the dose of bis-choline tetrathiomolybdate is temporarily interrupted, dosing is resumed when the patient exhibits baseline levels of one or more of hemoglobin, platelets, or neutrophils.

A person of skill will understand that this recital of liver function or bone marrow suppression tests is intended to be non-limiting. Other test of liver function or bone marrow suppression may be performed. New tests of liver function or bone marrow suppression may be developed and used in place of the liver function tests presently disclosed.

In another aspect, the present disclosure further provides methods for decreasing the daily dose of bis-choline tetrathiomolybdate in a patient exhibiting neurological worsening. In an embodiment, neurological worsening is assessed using the UWDRS Part III score. In an embodiment, a baseline UWDRS Part III is determined before bis-choline tetrathiomolybdate administration. In an embodiment, neurological worsening is defined as an increase in UWDRS Part III score over baseline of 1, 2, 3, 4, 5, 6, 7, or 8 points. In another embodiment, neurological worsening is defined as an increase in UWDRS Part III score over baseline of 4, 5 or 6. In another embodiment, neurological worsening is defined as an increase in UWDRS Part III score over baseline of 4 when the baseline UWDRS Part III was less than 20. In another embodiment, neurological worsening is defined as an increase in UWDRS Part III score over baseline of 6 when the baseline UWDRS Part III was 20 or greater. In an optional aspect, modification comprises discontinuing bis-choline tetrathiomolybdate. In an optional aspect, modification comprises after said patient no longer exhibits neurological worsening, administering a modified dose of bis-choline tetrathiomolybdate. In a certain aspect, a patient no longer exhibits neurological worsening when it is determined that said patient's UWDRS Part III score has stabilized. In one embodiment, the modified dose is a reduced dose. In some embodiments, the modified dose is half the daily dose administered before the patient exhibits neurological worsening. In other embodiments, the modified dose is less than the daily dose administered before the patient exhibits neurological worsening, such as 15 mg less than the daily dose administered before the patient exhibits neurological worsening. In some embodiments, if the patient was on a 15 mg once daily dose of bis-choline tetrathiomolybdate, 15 mg bis-choline tetrathiomolybdate every other day; if the patient was on a 30 mg once daily dose of bis-choline tetrathiomolybdate, 15 mg bis-choline tetrathiomolybdate once daily; if the patent was on a 45 mg once daily dose of bis-choline tetrathiomolybdate, 15 to 30 mg bis-choline tetrathiomolybdate once daily; if the patent was on a 60 mg once daily dose of bis-choline tetrathiomolybdate, 30 mg bis-choline tetrathiomolybdate once daily; if the patent was on a 75 mg once daily dose of bis-choline tetrathiomolybdate, 30 to 45 mg bis-choline tetrathiomolybdate once daily; or if the patent was on a 90 mg once daily dose of bis-choline tetrathiomolybdate, 45 mg bis-choline tetrathiomolybdate once daily.

In some embodiments, the disclosure relates to increasing or decreasing the dose of bis-choline tetrathiomolybdate by a fixed increment. In an embodiment, the method comprises administering to a patient a first dose level comprising about 15 to about 90 mg per day of bis-choline tetrathiomolybdate for a time period, followed by administering a second dose level comprising at least about 15 mg per day less bis-choline tetrathiomolybdate than the amount of bis-choline tetrathiomolybdate in the first dose level for a second period of time. In an embodiment, the second dose level is 15 mg every other day. Dose level and daily dose may be used interchangeably. A dose level may comprising one, two, three, four, five, or more doses, given at different times or the same time of day. A dose may optionally be a single tablet or two tablets. Optionally a dose may be provided as a tablet, capsule, or other pill. Optionally, a dose may be in liquid form.

In some embodiments, the first dose level is 15 mg or 30 mg or 45 mg or 60 mg or 75 mg or 90 mg. In an optional aspect, the first dose level may be more than 90 mg. In some embodiments, the second dose level is 15 mg or 30 mg or 45 mg or 60 mg or 75 mg or 90 mg. In an optional aspect, the second dose level may be more than 90 mg. A personal of skill will understand that this list of dose levels is non-limiting. Optionally, the dose may be adjusted based upon the weight of the subject. Optionally, the dose may be adjusted by measuring bioavailability of the drug such as by measuring the serum concentration of tetrathiomolybdate after administration of bis-choline tetrathiomolybdate. Optionally, the dose may be adjusted by measuring copper in the serum of the patient. Optionally, the dose may be adjusted by measuring $NCC_{corrected}$.

In an embodiment, the first dose level is 90 mg and the second dose level is 15 mg. In an embodiment, the first dose level is 90 mg and the second dose level is 75 mg. In other embodiments the first dose level is 90 mg or 75 mg or 60 mg or 45 mg and the second dose level is 15 mg less than the first dose level. In another embodiment, the second dose level is 30 mg less than the first dose level. In other embodiments, treatment with bis-choline tetrathiomolybdate is discontinued between the first dose level and the second dose level. In an embodiment, treatment is discontinued after an abnormal test results. In an embodiment, treatment with the second dose level occurs after the patient exhibits no abnormal test result.

In another aspect the present disclosure provides pharmaceutical compositions for treating Wilson Disease in a patient comprising bis-choline tetrathiomolybdate. Certain pharmaceutical compositions of bis-choline tetrathiomolybdate are provided by U.S. Pat. No. 7,189,865, which is incorporated by reference in its entirety. Pharmaceutical compositions are described generally by Remington: The Science and Practice of Pharmacy, 22nd edition (2012).

In some embodiments, the pharmaceutical composition comprises bis-choline tetrathiomolybdate and a second pharmaceutically active ingredient. In an embodiment the second pharmaceutically active ingredient is zinc. Zinc may be provided as zinc acetate or zinc sulfite. In an embodiment the second pharmaceutically active ingredient is tetrathiomolybdate salt other than the bis-choline salt. Optionally, the second pharmaceutically active ingredient is ammonium tetrathiomolybdate. In another embodiment the second pharmaceutically active ingredient is copper chelator. In an optional embodiment, the second pharmaceutically active ingredient is 2,3,2-Tetramine or D-penicillamine.

In some embodiments, the compositions and methods of the disclosure relate to salts of tetrathiomolybdate other than a bis-choline salt of tetrathiomolybdate. In some embodiments, the tetrathiomolybdate salt is a salt of tetrathiomolybdate and any pharmaceutically acceptable counterion. Exemplary counterions include, without limitation, ammonium, choline, and acetylcholine. The counterion may be, for example, a positively charged organic acid. Dosing is adjusted according to the molecular weight of the salt.

In another aspect the present disclosure provides kits for treating Wilson Disease, comprising at least three sets of pharmaceutical dosage units; and instructions for use. In an embodiment, the kit comprising sufficient tablets for a 7-day or 30-day or 90-day course of treatment with instructions for use. In an embodiment, the instructions for use indicate test of liver functions and thresholds for increasing or decreasing the number of pharmaceutical dosage units or fractional units of the pharmaceutical dosage unit to administered each day. In an embodiment, the kit further comprises zinc tablets. In an embodiment, the kit further comprises a copper chelator other than bis-choline tetrathiomolybdate. In another aspect the present disclosure provides compositions for use in any of the methods of the disclosure. In another aspect the present disclosure provides compositions for use in the manufacture of a medicament for use in any of the methods of the disclosure.

For oral administration, the pharmaceutical compositions of the present disclosure may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycolate and the like), wetting agents (e.g. sodium laurylsulphate) and the like. Such tablets may also be coated by methods well known in the art.

The dose administered may be adjusted according to age, weight and condition of the patient, as well as the route of administration, dosage form and regimen and the desired result. In some embodiments, doses administered to the subject are titrated until a desired endpoint is reached.

The compositions described above may be administered in the dosage forms as described above in single or divided doses of one to four times daily.

Dosage units including tablets, capsules and caplets, of various sizes can be prepared, e.g., of about 2 to 10000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

In some embodiments, bis-choline tetrathiomolybdate is provided in the same dosage unit in the form of a divisible dosage unit. For example, in some embodiments a scored tablet may provide the dosage unit. Under the direction of a physician or other medical professional, the subject may be directed to take one portion of the dosage unit, wherein the one portion will provide the desired dosage level for given interval. At the following interval, the patient may be instructed to take two or more portions of the dosage unit wherein the two or more portions will provide the desired dosage level for that interval.

Liquid formulations can also be prepared by dissolving or suspending one or the combination of active substances in a conventional liquid vehicle acceptable for pharmaceutical administration so as to provide the desired dosage in one to four teaspoonfuls.

Such dosage forms can be administered to the patient on a regimen of one to four doses per day.

Certain aspects of the disclosure are based on the surprising discovery that administering bis-choline tetrathiomolybdate in fed conditions results in a 60% to 75% decrease in absorption as compared to administering bis-choline tetrathiomolybdate under fasted conditions. In one aspect of the disclosure, bis-choline tetrathiomolybdate is administered in a fasted state to a patient suffering from Wilson Disease. In other embodiments, bis-choline tetrathiomolybdate is administered following an overnight fast. In yet other embodiments, bis-choline tetrathiomolybdate is administered on an empty stomach, after following an fast of about 1, 2, 3, 4, 5, 6, 7, or 8 hours. In certain embodiments, bis-choline tetrathiomolybdate is administered as an enterically coated formulation.

All of the features described herein (including any accompanying claims, abstract and drawings), and/or all of the steps of any method so disclosed, may be combined with any of the above aspects in any combination, except combinations where at least some of such features and/or steps are mutually exclusive. Specifically, any of the active agents and compositions described herein can be used in any of the described methods of treatment. Any and all such combinations are explicitly envisaged as forming part of the invention.

As used herein, the following terms shall have the following meanings:

"Bis-choline tetrathiomolybdate" refers to the bis-choline salt of tetrathiomolybdate or pharmaceutical compositions thereof. Bis-choline tetrathiomolybdate is also known as choline tetrathiomolybdate or ATN-224 or WTX101 or WTX-101 or DECUPRATE™. "WD" refers to Wilson Disease.

"QOD" or "quaque altera die" refers to administration of a treatment every other day, e.g. 15 mg QOD is understood in the art to indicate administration of a 15 mg dose every other day. "QD" or "quaque die" refers to administration of treatment once a day, e.g. 15 mg QD is understood in the art to indication administration of a 15 mg dose once a day. "SoC" refers to standard of care.

"Consecutive test results" or "consecutive abnormal test results" refers to the results of two or more measurements of the same parameter taken at two different time points. In certain embodiments, said measurements are taken one week apart. In other embodiments, said measurements are taken two weeks apart.

"Non-Ceruloplasmin-Bound Copper" or "NCC" refers the concentration of free copper in serum. In plasma, copper is either bound to ceruloplasmin, or more loosely bound to other plasma proteins, such as albumin or smaller circulating peptides. The loosely bound copper not bound to ceruloplasmin (i.e. non-ceruloplasmin bound copper, or NCC) is sometimes referred to as "free" copper. In the healthy situation (i.e., those without Wilson disease), generally more than 70% of the total plasma copper is bound to ceruloplasmin. Due to Wilson disease, ceruloplasmin bound copper levels are typically low in Wilson disease and may explain overall low total plasma copper levels observed in Wilson disease patients. However, when the free (that is, non-ceruloplasmin-bound) copper is calculated by subtracting the ceruloplasmin copper from the total serum copper level, this is usually found to be elevated above the upper limit of normal (>15 mg/dL). In untreated Wilson disease patients, NCC levels are typically more than 25 µg/dL. To calculate NCC level (in µg/dL), the ceruloplasmin (in mg/dL) is multiplied by 3; this value is then subtracted from the total serum copper level (in µg/dL).

"$NCC_{corrected}$" or "$NCC_{corr}$" refers to the NCC corrected for copper contained in tetrathiomolybdate-copper-albumin complexes. Exemplary methods for determining $NCC_{corr}$ are provided Weiss et al. Lancet Gastroenterol Hepatol. 2:869-876 (2017), which is incorporated into this disclosure in its entirety. Mechanisms of copper incorporation into ceruloplasmin are described in Hellman et al. *J. Bio. Chem.* 48:46632-38 (2002).

"Model for End-Stage Liver Disease" or "MELD" refers to a scoring system for assessing the severity of chronic liver disease. The MELD uses the subject's values for serum bilirubin, serum creatinine, and the international normalised ratio for prothrombin time (INR) to predict survival. It is calculated according to the following formula: MELD=3.78×ln[serum bilirubin (mg/dL)]+11.2×ln[INR]+9.57×ln[serum creatinine (mg/dL)]+6.43

"Modified Nazer Score" refers to an assessment of liver status and consists of a composite of 5 laboratory parameters: aspartate aminotransferase, international normalised ratio, bilirubin, albumin, and white blood cell count. The score has a total range of 0 to 20, and lower values indicate improvement.

"Fibrosis-4 Index/Transient Elastography" or "FIB-4 Index" refers to a formula used to predict liver fibrosis based on standard biochemical values (ALT, aspartate aminotransferase, and platelet count) and age.

"Transient elastography" refers to a non-invasive imaging method that evaluates the degree of liver fibrosis or fatty deposits in the liver, by determining the speed of sound waves through the liver utilizing a sonogram.

"Ceruloplasmin" refers to a ferroxidase enzyme that in humans is encoded by the CP gene. Ceruloplasmin is the major copper-carrying protein in the blood, and in addition plays a role in iron metabolism.

"Total Copper and Total Molybdenum" or "total Cu and total Mo analysis" refers to the measurement of the total concentration of copper and the total concentration of molybdenum (Mo) in the serum of a patient.

"Speciation Profiling" refers to Mo, Cu, and protein complex profiling with size exclusion chromatography.

"Unified Wilson Disease Rating Scale" or "UWDRS" refers to a clinical rating scale designed to evaluate the neurological manifestations of WD that generally can be divided into 3 movement disorder syndromes: a. dystonic, b. ataxic, and c. Parkinsonian syndrome. The UWDRS comprises three parts: UWDRS Part I (consciousness, item 1), UWDRS Part II (a historical review of daily activity items [disability], items 2 to 11), and UWDRS Part III (a neurological examination, items 12 to 34). The UWDRS Part I and Part III typically is assessed by a neurologist. The UWDRS Part II typically is reported by the subject or family. The UWDRS is described in Czlonkowska A et al. *Neurol Neurochir Pol* 41:1-12 (2007), which is incorporated into this disclosure in its entirety.

"Clinical Global Impression-Severity Scale" or "CGI-S" refers to a 7-point scale that requires the clinician to rate the severity of the subject's illness at the time of assessment, relative to the clinician's past experience with subjects who have the same diagnosis. Considering total clinical experience, a subject is assessed on severity of illness at the time of rating as: 1, normal, not at all ill; 2, borderline ill; 3, mildly ill; 4, moderately ill; 5, markedly ill; 6, severely ill; or 7, extremely ill.

"Clinical Global Impression-Improvement Scale" or "CGI-I" refers to a 7-point scale that requires the clinician to assess how much the subject's illness has improved or worsened relative to a baseline state at the beginning of the intervention and rated as: 1, very much improved; 2, much improved; 3, minimally improved; 4, no change; 5, minimally worse; 6, much worse; or 7, very much worse.

"Brief Psychiatric Rating Scale-24" or "BPRS-24" refers to a 24-item instrument that allows the rater to measure severity of psychiatric manifestations. The BPRS-24 assesses 24 psychiatric symptoms. The presence and severity of psychiatric symptoms are rated on a Likert scale ranging from 1 (not present) to 7 (extremely severe). The BPRS-24 can be performed by a trained physician.

"EuroQoL 5 Dimensions" or "EQ-5D" refers to testing that consists of the EQ-5D-5L Descriptive System and the EQ Visual Analogue Scale. The descriptive system comprises 5 dimensions (mobility, self-care, usual activities, pain/discomfort, and anxiety/depression) each of which has 5 levels of severity (no problems/slight problems/moderate problems/severe problems/extreme problems). For the scoring in the EQ-5D-5L Descriptive System, the respondent is asked to indicate his/her health state by ticking (or placing a cross) in the box against the most appropriate statement in each of the 5 dimensions. This decision results in a 1-digit number expressing the level selected for that dimension. The digits for 5 dimensions can be combined in a 5-digit number describing the respondent's health state.

"Treatment Satisfaction Questionnaire for Medication" or "TSQM-9" refers to a score used to assess the overall level of satisfaction or dissatisfaction with medication subjects are taking. This composite scale is comprised of 2 items on the TSQM-9 survey: How satisfied are you that good things about this medication outweigh the bad things? Taking all things into account, how satisfied or dissatisfied are you with this medication?

"Three Most Troublesome Symptoms" refers to a subject's 3 most troublesome symptoms. Each subject, or the subject and caregiver, identifies their 3 most troublesome symptoms, and these are documented on a written form as well as the impact these symptoms have on their activities of daily living. The 3 most troublesome symptoms are recorded via videotape from consenting subjects, where feasible and appropriate.

"Timed 25F Walk Test" refers to a quantitative mobility and leg function performance test based on a timed 25 foot walk. The subject is directed to one end of a clearly marked 25-foot course and is instructed to walk 25 feet as quickly as possible, but safely. The time is calculated from the initiation of the instruction to start and ends when the subject has reached the 25-foot mark. The task is immediately administered again by having the subject walk back the same distance. Scoring for the timed 25F Walk Test is the average of the 2 trials. Subjects may use assistive devices when doing this task.

"Nine-Hole Peg Test" or "9-HPT" refers to a brief, standardised, quantitative test of upper extremity function. Both the dominant and non-dominant hands are tested twice. The subject is seated at a table with a small, shallow container holding 9 pegs and a wood or plastic block containing 9 empty holes. On a start command when a stopwatch is started, the subject picks up the 9 pegs 1 at a time as quickly as possible, puts them in the 9 holes, and, once they are in the holes, removes them again as quickly as possible 1 at a time, replacing them into the shallow container. Two consecutive trials with the dominant hand are immediately followed by 2 consecutive trials with the non-dominant hand. The score for the 9-HPT is the average of the 4 trials.

"Non-Verbal Stroop Interference Test" refers to an effective measure of executive functioning, the ability to plan, apply knowledge, and make decisions. In psychology, the Stroop effect is a demonstration of interference in the reaction time of a task. There is no verbal communication during this test. The test is taught with non-verbal directions, using gestures and demonstration.

"Digit Span Test" refers to a test measured for forward and reverse-order (backward) recall of digit sequences and digit span sequencing. Digit sequences are presented beginning with a length of 2 digits and 2 trials are presented at increasing list length. Testing ceases when the subject fails to accurately report either trial at 1 sequence length or when the maximal list length is reached (9 digits, 8 backwards).

"Adverse Event" refers to any untoward medical occurrence in a clinical investigation subject administered a pharmaceutical product, which does not necessarily have a causal relationship with this treatment. An adverse event can therefore be any unfavourable and/or unintended sign (including an abnormal laboratory finding), symptom, or disease temporally associated with the use of an investigational medicinal product, whether or not related to the investigational medicinal product. Clinically significant abnormal laboratory or other examination findings, including neurological examination findings are reported as adverse events. The person of skill will exercise his or her medical and scientific judgment in deciding whether an abnormal laboratory finding or other abnormal assessment is clinically significant. Any abnormal test that is determined to be an error does not require reporting as an adverse event.

The severity of all adverse events is graded according to the Common Terminology Criteria for Adverse Events (CTCAE). These criteria can be found at http://ctep.cancer.gov/reporting/ctc.html. For those adverse events not listed in the CTCAE, the following grading system is used: Mild (CTCAE Grade 1): Transient symptoms, awareness of sign/symptom, but easily tolerated and no interference with subject's daily activities. Moderate (CTCAE Grade 2): Marked signs/symptoms that interfere with subject's usual activities, but still acceptable. Severe (CTCAE Grade 3): Incapacitating signs/symptoms which cause considerable interference with the subject's daily activities, unacceptable. Life-threatening (CTCAE Grade 4): Life threatening or disabling adverse event. Death (CTCAE Grade 5): Death-related adverse event.

"Adverse (Drug) Reaction" refers to all noxious and unintended responses to a medicinal product related to any dose should be considered an adverse drug reaction. "Responses" to a medicinal product means that a causal relationship between a medicinal product and an adverse event is at least a reasonable possibility, i.e., the relationship cannot be ruled out.

"Unexpected Adverse Drug Reaction" refers to an adverse reaction, the nature or severity of which is not consistent with the applicable product information.

"Pharmacologic Properties" refers to absorption, distribution, metabolism, and excretion of a drug should be considered.

"Adverse Events of Special Interest" refers to any new neurological symptom or clinically significant worsening of an ongoing neurological symptom after initiation of study drug therapy will be designated to be an AESI, whether serious or non-serious.

"Serious Adverse Events" refers to an adverse event or adverse reaction that results in any of the following outcomes: death or a life-threatening adverse event, requires hospitalisation or prolongation of existing hospitalisations, a persistent or significant disability/incapacity or substantial disruption of the ability to conduct normal life functions, a congenital anomaly/birth defect, or an important medical event.

An adverse event or adverse reaction is considered "life-threatening" if, in view of either the Investigator or Sponsor, its occurrence places the subject at immediate risk of death. It does not include an event that, had it occurred in a more severe form, might have caused death.

Any hospital admission with at least 1 overnight stay will be considered an inpatient hospitalisation. An emergency room visit without hospital admission will not be recorded as an SAE under this criterion, nor will hospitalisation for a procedure scheduled or planned before signing of informed consent. However, unexpected complications and/or prolongation of hospitalisation that occur during elective surgery should be recorded as adverse events and assessed for seriousness. Admission to the hospital for social or situational reasons (i.e., no place to stay, live too far away to come for hospital visits) is not considered inpatient hospitalisations.

Important medical events that may not result in death, be life-threatening, or require hospitalisation may be considered an SAE when, based upon appropriate medical judgment, they may jeopardise the subject and may require medical or surgical intervention to prevent one of the outcomes listed above. Examples of such medical events include allergic bronchospasm requiring intensive treatment in an emergency room or at home, blood dyscrasias or convulsions that do not result in inpatient hospitalisations, or the development of drug dependency.

"Medical History" refers to information on prior and concomitant medication, prior and current diagnoses, conditions, and surgeries that are considered significant, tobacco, alcohol, and drug use.

"Clinical Laboratory Evaluations" or "Clinical laboratory measures" include chemistry, hematology, coagulation, and urinalysis (with microscopy).

"Electrocardiogram parameters" refer to heart rate, RR interval, PR interval, QRS width, and QT interval.

"Vital Signs" refer to heart rate, blood pressure, respiration rate, temperature, and weight.

"Physical Examination" refers to an assessment of the following: general appearance, respiratory, cardiovascular, abdomen, skin, head and neck (including ears, eyes, nose, and throat), lymph nodes, thyroid, and musculoskeletal (including spine and extremities) systems. Unified Wilson Disease Rating Scale Part III is the neurological examination used in this study.

The term "score" as used herein refers to a relative value, level, strength, or degree of an assay result. It can be artificially created by a person of skill in the art or by using an algorithm, sometimes using samples with known analytes, optionally using samples with known concentrations or titers of the known analytes. It can be a number assigned manually by a person of skill in the art or generated with a formula or algorithm. It can also be a symbol, e.g., "−", "+", or "++". A score can be generated from calculation with a formula or algorithm, or can be assigned by visual inspection, measurement, or estimation of the assay result. When using samples with known concentrations or titers of known analytes, such samples can be assayed in diluted and undiluted conditions, and a range of scores or a standard curve of scores can be generated, which can be used to assign or estimate the scores of unknown samples assayed for the same analytes, in some embodiments using with the same assays.

EXAMPLES

Example 1: Bis-Choline Tetrathiomolybdate in Patients with Wilson's Disease: An Open-Label, Multicentre, Phase 2 Study Background Wilson's disease is a genetic disorder in which copper accumulates in the liver, brain, and other tissues. Therapies had been limited by efficacy, safety concerns, and multiple daily dosing. Bis-choline tetrathiomolybdate (WTX101) is an oral, first-in-class, copper-protein-aggregating molecule that targets hepatic intracellular copper and reduces plasma non-ceruloplasmin-bound copper (NCC) by forming tripartite complexes with albumin and by increasing biliary copper excretion. The efficacy and safety of WTX101 was assessed in the initial or early treatment of patients with Wilson's disease.

Methods

This open-label, phase 2 study was performed at 11 hospitals in the USA and in Europe. Patients (≥18 years) with Wilson's disease were enrolled who were untreated or who had received no more than 24 months of treatment with chelators or zinc, had a Leipzig score of 4 or more, and had NCC concentrations above the lower limit of the normal reference range (≥0·8 µmol/L). Eligible patients received WTX101 monotherapy at a starting dose of 15-60 mg/day on the basis of baseline NCC concentrations for the first 4-8 weeks, with response-guided individualised dosing for the remaining weeks up to week 24. Investigators, other hospital personnel, and patients were aware of the identity of the treatment. The primary endpoint was change in baseline NCC concentrations corrected for copper in tetrathiomolybdate-copper-albumin complexes ($NCC_{corrected}$) at 24 weeks, with treatment success defined as achievement or maintenance of normalized $NCC_{corrected}$ (≤2·3 µmol/L [upper limit of normal]) or achievement of at least a 25% reduction in $NCC_{corrected}$ from baseline at 24 weeks. This study is registered with ClinicalTrials.gov, number NCT02273596.

Findings

Twenty-eight patients were enrolled and received WTX101; 22 (79%) patients completed the study up to week 24. At 24 weeks, 20 (71%, 95% CI 51·3-86·8; p<0·0001) of 28 patients met the criteria for treatment success: 16 (57%) treated with WTX101 either achieved or maintained normalised $NCC_{corrected}$ concentrations and 4 (14%) had at least a 25% reduction from baseline $NCC_{corrected}$. Mean $NCC_{corrected}$ was reduced by 72% from baseline to week 24 (least squares mean difference –2·4 µmol/L [SE 0·4], 95% CI –3·2 to –1·6; p<0·0001). Surprisingly, no cases of paradoxical drug-related neurological worsening were recorded. Liver function was stable in all patients, although reversible increased concentrations of asymptomatic alanine or aspartate aminotransferase, or γ-glutamyltransferase, without increased bilirubin, occurred in 11 (39%) of 28 patients who received at least 30 mg/day WTX101. 11 serious adverse events were reported in seven (25%) patients, and included psychiatric disorders (six events in four patients), gait disturbance (one event), elevated liver aminotransferases (two events in two patients, one with agranulocytosis), and decline in neurological functioning (one event, likely due to natural disease progression although causality could not be ruled out). The seven serious adverse events categorised as psychiatric disorders and as gait disturbance were assessed as unlikely to be related to the study drug, whereas the remaining four events were possibly or probably related.

Interpretation

The results indicated that WTX101 might be a promising new therapeutic approach for Wilson's disease, with a unique mode of action. In view of its once-daily dose and favourable safety profile, WTX101 could improve the treatment of patients with this debilitating condition.

Introduction

Wilson's disease is an autosomal recessive disorder of impaired copper transport that leads to copper accumulation in the liver, brain, and other tissues. The disease is caused by mutations in the ATP7B gene, which encodes a copper-transporting ATPase. Decreased ATP7B function leads to reduced copper incorporation into ceruloplasmin and impaired biliary copper excretion. Wilson's disease affects about one in 30000 people, but prevalence varies among populations, and underdiagnosis could be significant. Clinical presentation differs widely, and includes forms of liver disease, neurological and psychiatric manifestations, and Kayser-Fleischer corneal rings. Abnormal laboratory findings include raised concentrations of free non-ceruloplasmin-bound-copper (NCC) in plasma and low concentrations of circulating ceruloplasmin.

If left undiagnosed and untreated, Wilson's disease is universally fatal. Oral treatments approved several decades ago to reduce copper concentrations include chelators (penicillamine and trientine), which increase urinary excretion of copper, or zinc, which inhibits gastrointestinal copper absorption.

Few, if any, prospective studies have been done with these treatments, and there are considerable unmet needs with respect to efficacy, safety, and simplicity of dosing regimens. Furthermore, patients with neurological presentation who initiate treatment with penicillamine or trientine can have paradoxical early worsening of neurological disease, with rapid appearance of new neurological signs or worsening of existing neurological signs, which leads to marked disability. In clinical studies, the proportion of patients with neurological Wilson's disease affected by early worsening after chelator initiation ranges from 19% to 35%. Early neurological worsening can be irreversible and might be due to rapid mobilisation of free copper.

Bis-choline tetrathiomolybdate (WTX101) is an oral first-in-class copper-protein-binding molecule under investigation as once-daily monotherapy for Wilson's disease. A previous form of the drug, ammonium tetrathiomolybdate, rapidly controlled copper concentrations in clinical studies; however, it is too unstable for routine use. The bis-choline moiety is a major advance since it has improved stability and, unlike other available treatments, WTX101 seems to have direct intracellular activity in hepatocytes, in which it binds excess copper and promotes biliary copper excretion. WTX101 also rapidly binds free plasma copper, creating a stable tripartite complex of tetrathiomolybdate with copper and albumin.

Methods

The open-label, phase 2 study was performed at 11 hospitals. Eligible patients were aged 18 years or older, with a diagnosis of Wilson's disease established by a Leipzig score of 4 or more. At enrolment, patients had received no previous treatment for Wilson's disease or had been treated with chelation or zinc for no longer than 24 months, and had NCC concentrations above the lower limit of the normal reference range (≥0·8 µmol/L). Patients with decompensated hepatic cirrhosis, a MELD score greater than 11, or a modified Nazer score (revised King's score) greater than 6 were excluded.

The protocol and all amendments were approved by local institutional review boards and ethics committees. Study conduct was monitored by an independent data and safety monitoring committee. All participants provided written informed consent in accordance with the Declaration of Helsinki.

Investigators, other hospital personnel, patients, and the study sponsor were aware of the identity of the treatment.

Previously treated patients had a 48-h washout period before WTX101 initiation. Patients received a starting dose of WTX101 of 15-60 mg/day on the basis of baseline NCC concentrations for the first 4-8 weeks, with subsequent response-guided individualised dosing over the remaining 24 weeks. Although dosing of WTX101 was initially twice daily, an early protocol amendment implemented once-daily dosing (if deemed appropriate by the investigator).

After a high alanine aminotransferase (ALT) concentration in a patient receiving 120 mg/day, the dose regimen was amended to decrease the maximum dose from 300 mg/day to 60 mg/day.

At the discretion of the principal investigator, the dose of WTX101 could be adjusted by predefined increments on the basis of various factors, including clinical chemistry and hematology, clinical assessment, safety, and NCC concentrations. Up-titration was stepwise, with each increase restricted to double the previous dose, and not permitted if NCC was within or below the normal range. The dose was temporarily reduced or interrupted after two consecutive reports of ALT or aspartate aminotransferase (AST) concentrations that were at least 2-5 times above the normal range, a reduction of 30% or more in baseline hemoglobin, or an increase of 4 points or more in neurological signs based on the Unified Wilson Disease Rating Scale (UWDRS) part III (an accepted and validated quantitative neurological scoring system developed specifically for Wilson's disease).

Using values for plasma total copper and ceruloplasmin concentrations, NCC was calculated by subtracting the amount of copper bound to ceruloplasmin from total copper concentrations (determined with inductively coupled plasma mass spectrometry). NCC measurements were then corrected by subtracting the amount of copper bound in the tetrathiomolybdate-copper-albumin complex after WTX101 treatment, since this is not part of the reactive toxic copper pool. The correction method used the average molar ratio of copper to molybdenum in the tripartite complex, which was determined using the relationship between NCC and plasma molybdenum concentrations and confirmed by two independent methods. The NCC correction method was validated using random selections of test and validation samples.

The primary endpoint was change in $NCC_{corrected}$ from baseline to 24 weeks, which was measured as NCC concentrations corrected for copper contained in tetrathiomolybdate-copper-albumin complexes ($NCC_{corrected}$). Treatment success was defined as achievement or maintenance of normalised concentrations of $NCC_{corrected}$ (≤2·3 μmol/L [upper limit of normal]) or achievement of at least a 25% reduction in $NCC_{corrected}$ from baseline at 24 weeks.

Secondary endpoints were safety and tolerability, change in and time to normalisation of $NCC_{corrected}$ level clinical neurological disease, liver function, clinical symptoms, health-related quality of life (HRQoL), psychiatric status, and pharmacokinetics and exchangeable copper, speciation profiling, and urinary copper. Psychiatric status, pharmacokinetics data, and copper endpoints were also measured. Neurological disease was assessed as patient-reported disability, measured with UWDRS part II, and also as trained-rater-assessed neurological status, measured with UWDRS part III. Liver synthetic function was assessed by monitoring of international normalised ratio (INR) and albumin concentrations. Additionally, changes in liver function were assessed by modified Nazer score (based on bilirubin, INR, AST, albumin, and white blood cell count) and, in a post-hoc analysis, by the MELD score (based on bilirubin, creatinine, INR, and cause of liver disease). HRQoL was measured with the EuroQoL 5 Dimensions Visual Analogue Scale (EQ VAS).

Adverse event (AE) data was collected for onset, duration, seriousness, and severity, with relation to study medication determined by the investigator.

Planned enrollment was 30 patients, with at least 15 patients expected to have received limited (≤90 days) previous treatment with chelators or zinc. Since the aim of the study was to present primarily descriptive statistics, no formal power calculations were performed. Changes in copper concentrations and scores were summarised over time with descriptive statistics. Mixed-model repeated-measures analysis with a fixed-effect term were applied for clinic visit, and a spatial power covariance structure was applied to model the within-participant errors. A spatial power covariance structure was selected because it assumes that the within-participant correlation decays as the time distance increases between repeated measures. SAS (version 9.3) was utilised to provide change in least-squares mean over time, and the associated 95% CIs, SE, and two-sided p values.

Figure 1:
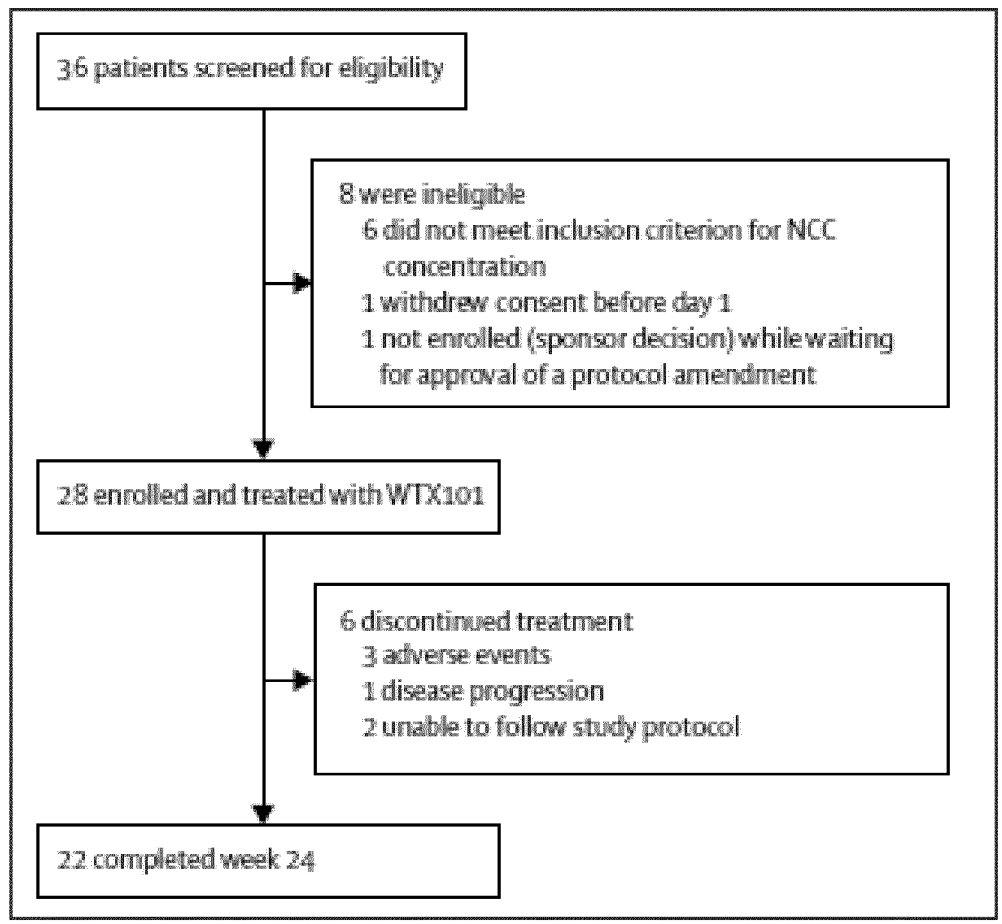

Twenty-eight patients were enrolled and treated with WTX101; 22 (79%) patients completed the study up to week 24 (FIG. 1). At baseline, 15 (54%) patients were women and the mean age was 34.1 years (SD 11·86) and ranged from 18 to 64 years. Nine (32%) patients had received no previous treatment for Wilson's disease. Nine (32%) patients had been treated for less than 28 days, and ten (36%) patients had been treated for between 28 days and 2 years (median 100 days [range 7-714]). Most patients had varying degrees of neurological signs at enrolment, most commonly dysarthria (19 [68%]), postural tremor (18 [64%]), impaired alternating movements of the hands (18 [64%]), and abnormal gait (17 [61%]), with abnormal gait primarily driven by ataxia (12 [43%]). Mean UWDRS part III score at baseline was 22.8 (SD 21.0; range 0-83) with only three (11%) patients scoring 0 (no neurological abnormalities). At baseline, 13 (46%) patients had liver cirrhosis, based on medical history (seven patients) or by estimates of AST-to-platelet ratio index (six patients). 14 (50%) patients had 26 instances of a liver-test abnormality at study entry (12 ALT, nine AST, one bilirubin, and four INR). Of these abnormalities, 24 were within 1-2 times and two were within 3-5-times the upper limit of normal.

At week 24, or at last dose received for patients with early discontinuation, the daily doses were 15 mg for six (21%) patients, 30 mg for 13 (46%) patients, and 60 mg (32%) for nine patients. More than 80% of the total dosing of WTX101 in the study was once daily.

Figure 2:
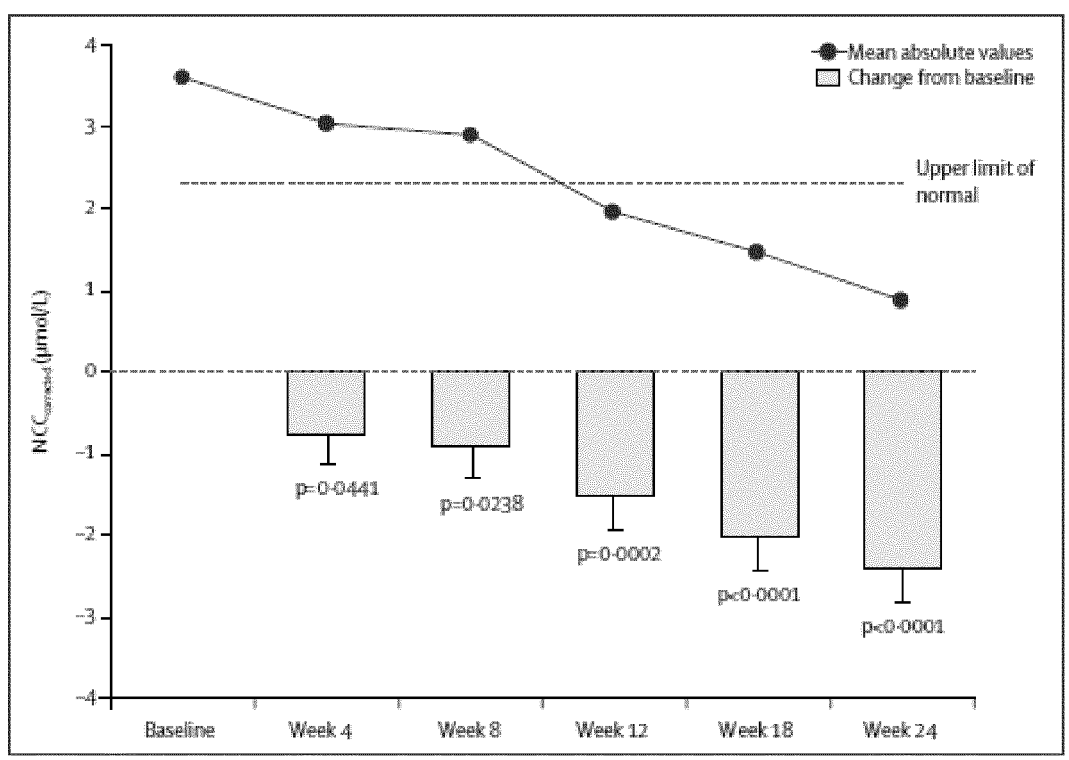

Treatment with WTX101 was associated with rapid improvements in $NCC_{corrected}$, such that mean $NCC_{corrected}$ concentrations were below the upper limit of normal by week 12 (FIG. 2). At 24 weeks, 20 (71%, 95% CI 51·3-86·8; p<0·0001) of 28 patients had achieved treatment success: 16 (57%) achieved or maintained normalised $NCC_{corrected}$ concentrations and 4 (14%) had a reduction of at least 25% in $NCC_{corrected}$ from baseline. Overall, mean $NCC_{corrected}$ was reduced by 72% from baseline to week 24 (least squares mean difference −2·4 μmol/L [SE 0·4], 95% CI −3·2 to −1·6; p<0·0001; Table 1, FIG. 2).

TABLE 1

Changes from baseline to week 24 in primary and secondary endpoints

|  | n | Baseline Mean (SD) | n | Week 24 Mean (SD)† | Change from baseline (SE, 95% CI)* | p value |
|---|---|---|---|---|---|---|
| NOC$_{corrected}$ (μmol/L) | 25 | 3.6 (2.1) | 23 | 0.9 (1.0) | −2.4 (0.4, −3.2 to −1.6) | <0.0001 |
| UWDRS part II score | 28 | 6.6 (10.0) | 21 | 4.1 (8.2) | −3.7 (0.9, −5.5 to 1.8) | 0.0003 |
| UWDRS part III score | 28 | 22.8 (21.0) | 21 | 16.6 (17.7) | −8.7 (1.9, −12.5 to −5.0) | <0.0001 |
| Albumin (g/L) | 28 | 39.2 (5.4) | 23 | 40.9 (3.2) | 2.3 (0.5, 1.26 to 3.42) | <0.0001 |
| INR | 27 | 1.11 (0.16) | 22 | 1.06 (0.08) | −0.05 (0.01, −0.08 to −0.02) | 0.0010 |
| Bilirubin (mg/dL) | 28 | 0.51 (0.29) | 23 | 0.49 (0.27) | 0.02 (0.03, −0.05 to 0.08) | 0.6352 |
| ALT (U/L) | 28 | 42.6 (32.8) | 23 | 36.8 (18.7) | 48.4 (13.6, 21.38 to 75.48) | 0.0006 |
| AST (U/L) | 28 | 36.6 (27.6) | 23 | 28.2 (9.9) | 3.8 (3.4, −2.89 to 10.59) | 0.2590 |
| GGT (U/L) | 28 | 70.1 (64.0) | 23 | 97.5 (77.7) | 60.7 (19.1, 22.79 to 98.62) | 0.0020 |
| Platelets (1 × 10$^9$/L) | 28 | 155.5 (72.5) | 23 | 147.9 (63.2) | 2.3 (3.4, −4.38 to 8.95) | 0.4975 |
| MELD score‡ | 27 | 7.7 (1.9) | 21 | 7.2 (1.8) | −0.5 (0.2, −0.86 to −0.08) | 0.0180 |
| Modified Nazer score | 28 | 1.4 (1.0) | 21 | 1.1 (0.6) | −0.4 (0.2, −0.91 to 0.08) | 0.0960 |
| EQVAS | 28 | 65.9 (23.0) | 23 | 74.3 (16.9) | 9.2 (2.9, 3.36 to 14.98) | 0.0024 |

*Based on a mixed-model repeated-measures analysis that used all patient data collected at baseline and all visits thereafter, up to and including week 24.
†Absolute mean values on an observed-case basis that do not include missing data or data from discontinued patients; one patient discontinued at week 23 but within the specified window for inclusion of plasma measurements and EQVAS scores as week 24 values.
‡Post-hoc analysis.

Data in Table 1 are absolute mean values on an observed-case basis that do not include missing data or data for patients who discontinued. NCC$_{corrected}$ refers to non-ceruloplasmin copper levels corrected for copper in tetrathiomolybdate-copper-albumin complexes. UWDRS refers to Unified Wilson Disease Rating Scale. INR refers to international normalised ratio. ALT refers to alanine aminotransferase. AST refers to aspertate aminotransferase. GGT refers to γ-glutamyltransferase. EQVAS refers to EuroQoL Visual Analogue Scale.

Figure 3:
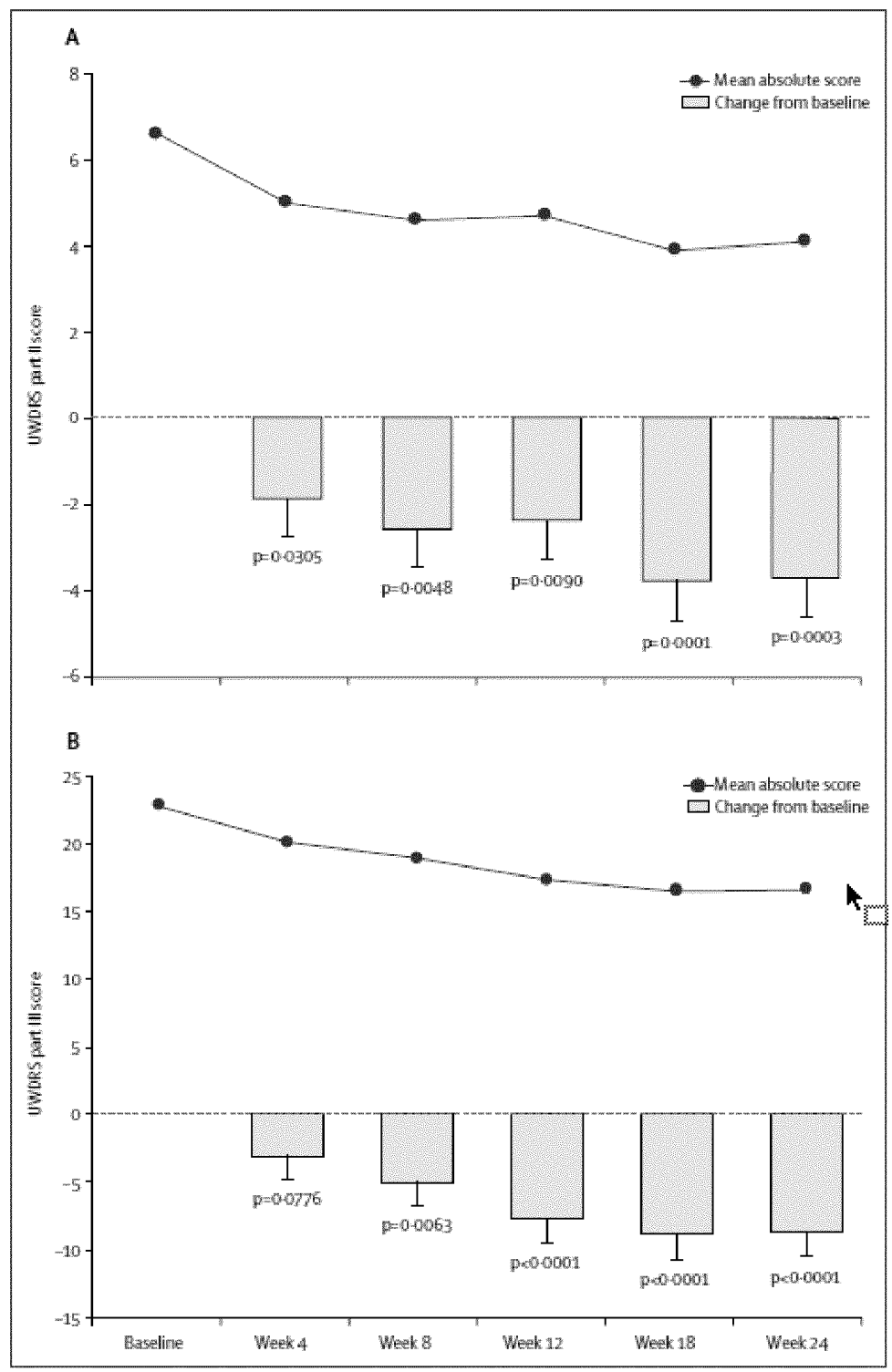

Disease-related disability was significantly improved after treatment with WTX101 (Table 1, FIG. 3). Mean UWDRS part II scores improved from 6·6 (SD 10·0) at baseline to 4·1 (8·2) at week 24 (Table 1, FIG. 3A). UWDRS part II score improved by at least one point in 12 (57%) patients and was unchanged in nine (43%) patients; no patient reported deterioration except for a patient who discontinued treatment at 21 weeks because of further decline of existing neurological disease.

Mean scores for UWDRS part III significantly improved from 22·8 (21·0) at baseline to 16·6 (17·7) at week 24 (Table 1, FIG. 3B). UWDRS part III score improved by 4 or more points in 14 (67%) patients and stabilised (within 3 points of baseline) in five (24%) patients at week 24. There was deterioration by five points in two (10%) patients: one patient scored 19 at baseline with fluctuations between 16 and 27 during the study, and the second patient scored 3 at baseline and 8 at weeks 18 and 24; disability was rated 0 throughout in these patients. Surprisingly, no cases of paradoxical neurological worsening attributed to the study drug were recorded in the 12 weeks after treatment initiation.

Although improvements in INR and albumin from baseline to week 24 were statistically significant, they were numerically small, indicating stable liver function (Table 1). Liver status, as estimated by MELD and modified Nazer score, was also largely unchanged throughout the study (Table 1).

Clinical improvements were reflected by significantly increased mean EQ VAS scores (Table 1).

Treatment with WTX101 was generally well tolerated and most adverse events were mild or moderate in intensity (summarised in Table 2). We recorded increased enzyme concentrations, primarily ALT, AST, or γ-glutamyltransferase, in the liver function tests of 11 (39%) of 28 patients receiving WTX101 at 30 mg/day or greater, without increased bilirubin. These increases usually occurred after 4-10 weeks, and were mostly mild or moderate, all asymptomatic, and normalised within 1-2 weeks after dose adjustments or treatment interruption of up to 6 weeks. Median peak ALT in these 11 patients was 197 U/L (range 101-1341), a 7·2-times increase from baseline. Three (11%) patients with ALT increases of between 14·3 times and 29·3 times from baseline discontinued treatment. The second highest ALT signal (615 U/L) occurred in one of the first enrolled patients, who received WTX101 at 120 mg/day. The per-protocol dose regimen was subsequently amended to lower the maximum dose to 60 mg/day. The patient with the most pronounced ALT signal (1341 U/L) received WTX101 30 mg/day and had ALT elevations (peak 400 U/L) with previous penicillamine treatment before enrolment. In the three patients in whom the drug was discontinued because of increased ALT concentrations, abnormal results from liver tests were reversible and not associated with notable increases in bilirubin.

TABLE 2

Adverse events and serious adverse events during treatment

|  | Number of Patients (%) |
|---|---|
| Patients reporting at least one treatment-emergent adverse event | 17 (61%) |
| ALT increased | 8 (29%) |
| GGT increased | 8 (29%) |
| AST increased | 7 (25%) |
| Hepatic enzyme increased | 4 (14%) |
| Blood alkaline phosphatase increased | 3 (11%) |
| Headache | 2 (7%) |
| Tremor | 2 (7%) |
| Nausea | 2 (7%) |
| Dry Skin | 2 (7%) |
| Leukopenia | 2 (7%) |
| Patients reporting at least one treatment-emergent serious adverse event | 7 (25%) |
| Psychotic disorder | 1 (4%) |
| Abnormal behavior | 1 (4%) |
| Adjustment disorder | 1 (4%) |
| Affective disorder | 1 (4%) |
| Mania | 1 (4%) |
| Personality disorder | 1 (4%) |
| ALT increased | 1 (4%) |
| Hepatic enzyme increased (severe increase in ALT or AST) | 1 (4%) |
| Gait disturbance | 1 (4%) |
| Agranulocytosis | 1 (4%) |
| Decline in Neurological functioning | 1 (4%) |

Listed are treatment-emergent adverse events that were reported by the investigator in at least two patients and all treatment-emergent serious adverse events. A patient could have had more than one adverse event or serious adverse event. The seven serious adverse events categorized as psychiatric disorders and as gait disturbance were assessed as unlikely to be related to the study drug, whereas the remaining four events were possibly or probably related. Adjustment disorder was reported in one patient, who then had a recorded exacerbation of the acute situation disturbance 6 weeks later (listed here as one serious adverse event). In a different patient, mania was reported on two separate occasions within a 3-week period during the 24-week study (listed here as one serious adverse event). ALT refers to alanine aminotransferase. GGT refers to γ-glutamyltransferase. AST=aspartate aminotransferase.

Two (7%) patients had leukopenia and one (4%) had thrombocytopenia reported as probably, possibly, or definitely related to the study drug; however, all recovered after dose adjustments. Few patients reported gastrointestinal or skin adverse events related to study treatment (Table 2).

Eleven serious adverse events were reported in seven (25%) patients: psychiatric disorders (six events in four patients), elevated liver aminotransferases (two events in two patients, one with agranulocytosis), gait disturbance (one event), and decline in neurological functioning (one event; Table 2). Psychiatric serious adverse events and gait disturbance were assessed as remote or unlikely to be related to study drug because of pre-existing neurological or psychiatric disease manifestations, whereas the other four serious adverse events were possibly or probably related to treatment.

One previously treated patient who had neurological worsening before enrolment had further neurological decline after week 12, despite study treatment, and discontinued at week 21, with a three-point increase in UWDRS part II and an 11-point increase in UWDRS part III from baseline. The neurological decline was assessed as probably due to natural disease progression, although causality could not be ruled out. Investigators discontinued treatment for two (7%) patients because psychiatric or behavioral symptoms led to their inability to follow the protocol. These patients had improved or unchanged UWDRS part III scores.

Discussion

Results show that WTX101 induced rapid copper control with significant $NCC_{corrected}$ reductions after approximately 3 months, accompanied by significant early improvements in neurological symptoms and function in most patients. This study was the first multinational prospective trial done in patients with Wilson's disease and aimed to assess treatment with a new oral medication, WTX101, with significant advantages in administration and dosing.

Previously available treatments could take several years to show clinical improvement in patients with Wilson's disease. Liver function might normalize over 1-2 years of the previous treatment regimens in most patients with liver disease or compensated cirrhosis at presentation, whereas symptom improvement in those with neurological disease was slower and might not improve or resolve as often as liver function. Without being bound by any particular theory, it is possible that rapid biochemical and clinical improvements observed with WTX101 are possibly related to its novel, copper-specific, and direct hepatic mechanism of action of lowering concentrations of toxic free copper in plasma. Treatment of patients who presented with neurological symptoms was particularly challenging because about half of those with neurological disease at presentation still have residual signs, even after years of chelation therapy. Furthermore, the paradoxical early neurological worsening might be observed in patients with neurological Wilson's disease even after treatment initiation with standard chelators, and neurological deficiencies can be irreversible in a third to a half of patients. In a study by Litwin and colleagues, early neurological worsening was observed in 12 (29%) of 42 patients with neurological Wilson's disease treated with penicillamine, with a mean time to neurological worsening from initiation of 2·3 months. Litwin et al. Early neurological worsening in patients with Wilson's disease. *J. Neurol Sci* 355:162-67 (2015). Potentially, the binding of WTX101 to copper in an inert and large protein complex that cannot redistribute to the CNS could be responsible for the apparent absence of early neurological worsening within the first 12 weeks of treatment. One possibility is that previously treated patients could have received chelation therapy for a sufficiently long duration that neurological worsening was not observed with subsequent WTX101 treatment; however, no cases of early neurological worsening were recorded in treatment-naive patients. One previously treated patient (<28 days of zinc) with neurological worsening before enrolment had further neurological decline, despite dose escalation, due to an inadequate clinical response to WTX101, and study treatment was discontinued at week 21. Although the neurological decline was assessed as probably due to natural disease progression, causality could not be ruled out. In addition to the patient who discontinued at week 21, two other participants discontinued treatment with WTX101 for neurological or psychiatric reasons. Neurological, psychiatric, or a combination of both neurological and psychiatric manifestations occur frequently in patients with Wilson's disease and were responsible for these two participants becoming unable to follow study procedures. Pre-existing psychiatric conditions also required several hospital admissions during the study, which by definition were documented as severe adverse events. Indeed, eight of the 11 reported severe adverse events were neurological or psychiatric in nature and occurred in five patients.

Synthetic liver function appeared to be stable with WTX101 over the 24-week study, as shown by results for INR and albumin concentrations. This finding was noted in all patients, regardless of whether they had evidence of cirrhosis. Of note, reversible increases in liver function tests were observed in 39% of patients in our study, independent of the stage of liver disease. Increases occurred 4-10 weeks after initiation, at 30 mg/day or higher, and were mostly mild or moderate. Patients who had elevations were all asymptomatic with respect to their liver disease. Results from liver function tests normalised within 1-2 weeks after dose adjustments or treatment interruption. There were no notable increases in bilirubin in patients with increased liver function test results, including those who discontinued the drug, indicating the absence of severe drug-induced liver injury. Similar dose-dependent, early, reversible aminotransferase increases occurred in patients with Wilson's disease treated with ammonium tetrathiomolybdate, which also responded to dose reduction or treatment interruption. However, similar liver test abnormalities were not reported with use of tetrathiomolybdate in patients without liver disease or primary biliary cirrhosis, suggesting that the observed effects are specific to Wilson's disease. One mechanism for the raised liver enzyme levels in response to WTX101 treatment could relate to its copper-modulating activity, such that removal of copper from hepatic pools, including metallothionein, led to a subsequent transient increase in hepatic aminotransferases. However, the exact mechanism remains to be elucidated.

Previously available treatments for Wilson's disease were subject to other potentially serious adverse events that frequently led to discontinuation and changes in treatment. In a retrospective study, 32% of patients on chelators, and 11% of patients on zinc, discontinued treatment because of adverse events. Penicillamine is associated with early sensitivity reactions, such as fever and rash, and various skin reactions, and later reactions including lupus-like syndrome and nephrotoxicity. Gastrointestinal adverse events are frequently reported with zinc treatment; 40% of children treated with zinc had gastrointestinal adverse events in a Polish cohort. Wiernicka et al., Gastrointestinal side effects in children with Wilson's disease treated with zinc sulphate. *World J Gastroenterol* 19:4356-62 (2013). In our study, two patients each reported nausea or dry skin deemed related to study treatment, but these were generally mild or moderate, and did not lead to discontinuation. Six patients discontinued study treatment. These discontinuations reflect the chronic life-limiting nature of symptomatic patients with Wilson's disease, with most enrolled patients having various degrees of neurological or psychiatric manifestations, and the exploratory approach in which the initial dosing regimen had to be amended.

Previously available treatments for Wilson's disease were prescribed as multiple daily doses, up to four times daily, and must be taken without food. Studies suggest that up to 45% of patients treated with current therapies have poor or problematic long-term adherence. Failure to comply with lifelong therapy could lead to symptom recurrence and progression of liver disease, or neurological or psychiatric symptoms, although there is individual variability in timeframe. Once-daily oral dosing is possible with WTX101, and might lead to improved adherence to treatment and better patient outcomes.

Although the sample size is sufficient for a phase 2 trial in an orphan disease, it is relatively small when assessing outcomes in a clinically heterogeneous disease. However, all results were consistent regardless of the assessment parameter applied, supporting the overall beneficial effect of WTX101 in the population studied. Patients with decompensated hepatic disease with increased MELD scores were excluded. A mixed population of treatment-naive and previously treated patients was necessary because of the enrolment difficulties associated with a rare disease, and since Wilson's disease is often treated very quickly after diagnosis. Inclusion of this population in our study also permitted evaluation of the effects of WTX101 in patients who previously received chelation therapy or zinc. The trial was uncontrolled and open label. Although an internal control is desirable, this is not always feasible in early drug development for rare diseases. However, there were improvements in results not susceptible to bias, including copper control and liver function. While the trial was of relatively short duration, extension studies to further investigate the long-term safety and efficacy of WTX101 are ongoing.

In conclusion, WTX101 treatment rapidly lowered free copper in patients with Wilson's disease, and this copper control was associated with reduced disability, improved neurological status, and stable liver function over 24 weeks. With dose adjustments, WTX101 showed a favourable safety profile with a simple once-daily oral dosing regimen without food effects. WTX101 therefore has the potential to address several unmet clinical needs.

Example 2: Long-Term Efficacy and Safety of WTX101 in Wilson Disease: Data from an Ongoing Extension of a Phase 2 Study In Example 1, oral once-daily WTX101 monotherapy rapidly lowered and controlled NCC, improved disability and neurological status, without early drug-induced neurological worsening and stabilized liver function in patients with WD after 24 weeks. 72-week efficacy and safety data from the ongoing extension period of the phase 2 study represents the first prospective report on long-term disease control with WTX101 in WD.

Example 1 was an open-label multicenter single-arm phase 2 trial conducted in 28 adults with a diagnosis of WD established by a Leipzig score of ≥4. For inclusion, NCC levels had to be above the lower limit of the normal reference range (≥0.8 µM). Participants had either no prior treatment for WD (n=9) or ≤24 months' prior treatment with chelation or zinc (<28 days, n=9; 28 days to 2 years, n=10). Participants received WTX101 for 24 weeks using a response-guided dosing regimen with individualized doses between 15 and 120 mg/day based on NCC levels, clinical assessments, and safety criteria.

Data were collected from the first 72 weeks of the extension period for the following parameters: (a) NCC levels, corrected for bound copper contained in tetrathiomolybdate-copper-albumin complexes ($NCC_{corrected}$); (b) Liver status, measured using standard laboratory measures and also by Model for End-Stage Liver Disease (MELD) score (based on bilirubin, creatinine and international normalized ratio [INR]); (c) Patient-reported disability using Unified Wilson Disease Rating Scale (UWDRS) part II, and neurological status using UWDRS part III; and (d) Safety is shown below.

At baseline of the core study, 46% of patients had cirrhosis of the liver based on medical history (n=7) or by estimates of AST to platelet ratio index (n=6). At week 24, or at last dose received for patients with early discontinuation, the daily dosages were 15 mg for 6 patients, 30 mg for 13 patients, and 60 mg for 9 patients. All 22 patients who completed the initial 24-week core study participated in the extension period described in this Example.

Twenty patients completed treatment to week 72. One patient discontinued treatment due to her wish to conceive. One patient was unable to comply with study procedures due to a progressive disease course despite ongoing treatment.

TABLE 3

Demographic and characteristics of participants at baseline of the core and extension periods.

| Characteristic | Baseline of core period (week 0) N = 28 | Beginning of extension period (week 24) N = 22 |
| --- | --- | --- |
| Mean age (range), years | 34.1 (18-64) | 36.5 (18-64) |
| Female sex, n (%) | 15 (54) | 12 (55) |
| $NCC_{corrected}$, µM | 3.6 ± 0.4 | 0.9 ± 0.2 |
| UWDRS part II score | 6.6 ± 1.9 | 4.1 ± 1.8 |
| UWDRS part III score | 22.8 ± 4.0 | 16.6 ± 3.9 |
| MELD score | 7.7 ± 0.4 | 7.2 ± 0.4 |
| ALT, U/L | 42.6 ± 6.2 | 36.8 ± 3.9 |
| Albumin, g/L | 39.2 ± 1.0 | 40.9 ± 0.7 |
| INR 1 | .11 ± 0.0 | 1.06 ± 0.0 |

Mean ± standard error unless stated

Free Copper Levels in Plasma

Figure 4:
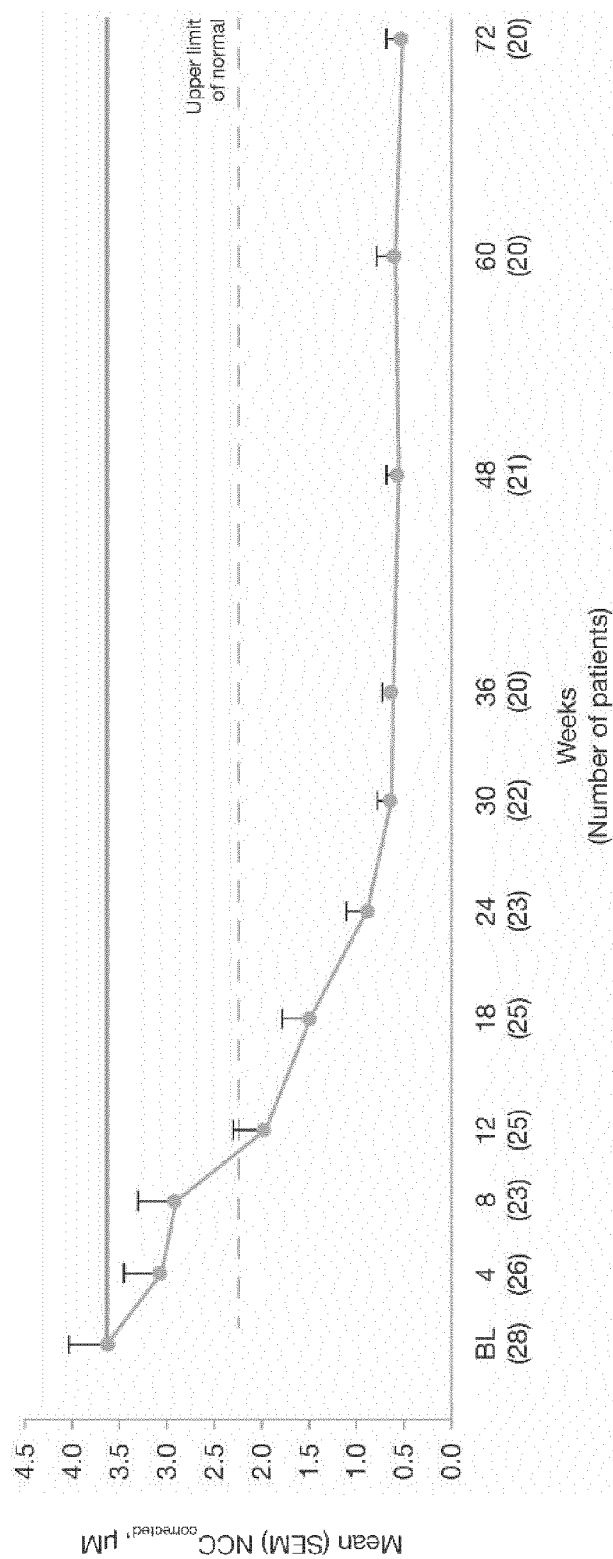
FIG. 4 depicts $NCC_{corrected}$ levels with once-daily WTX101 treatment.

Elevated mean (SEM) $NCC_{corrected}$ at baseline (3.6 [0.4] µM) was reduced and controlled at week 24 (0.9 [0.2] µM) and remained controlled at week 72 (0.5 [0.2] µM) (FIG. 4).

Liver Function

Figure 5:
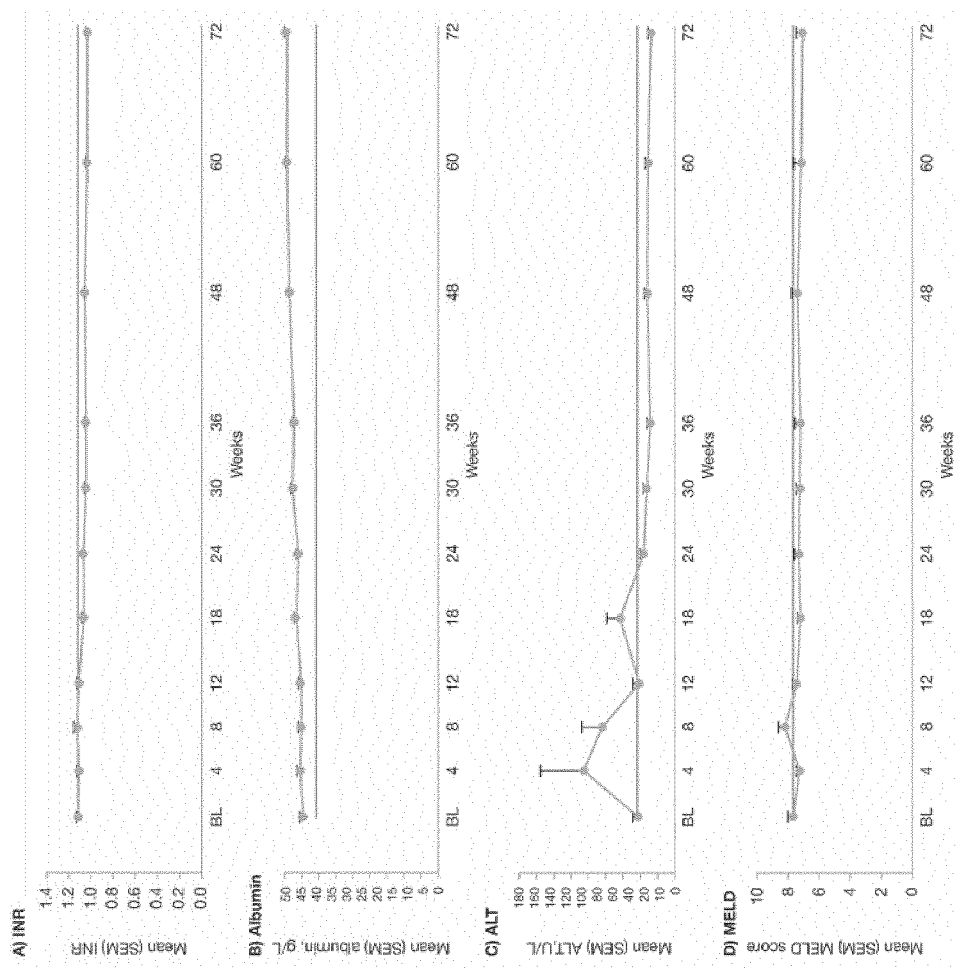
FIG. 5 depicts changes in measures of liver stability with once-daily WTX101 treatment.

Mean INR, albumin, ALT levels, and MELD score appeared improved or unchanged between week 24 and week 72, indicating stability of liver function (FIG. 5).

Reversible ALT elevations requiring dose adjustments, observed in 39% of patients (at ≥30 mg/day) to week 24 (Example 1), were not observed in the extension.

Figure 6:
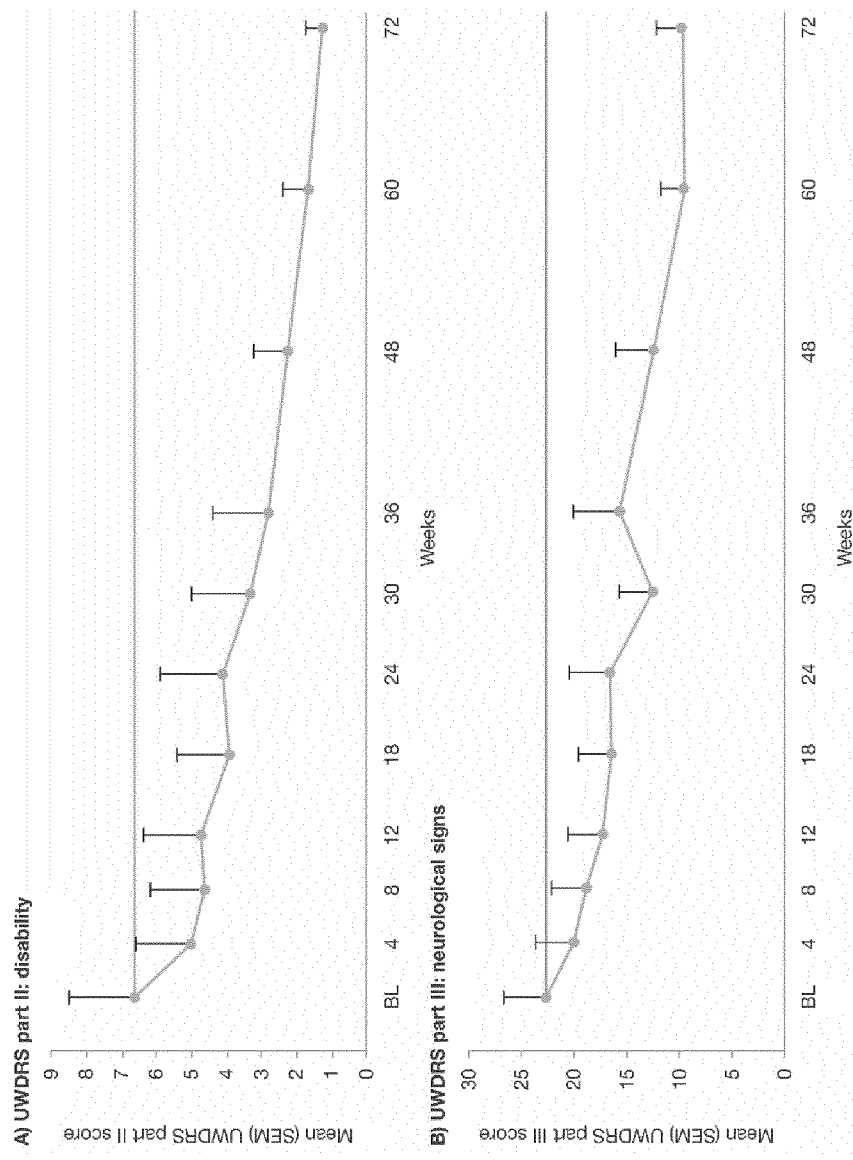
FIG. 6 depicts changes in disability and neurological signs with once-daily WTX101 treatment.

Patients showed continued improvements in mean UWDRS disability score and neurological signs score from week 24 to 72 (FIG. 6).

Figure 7:
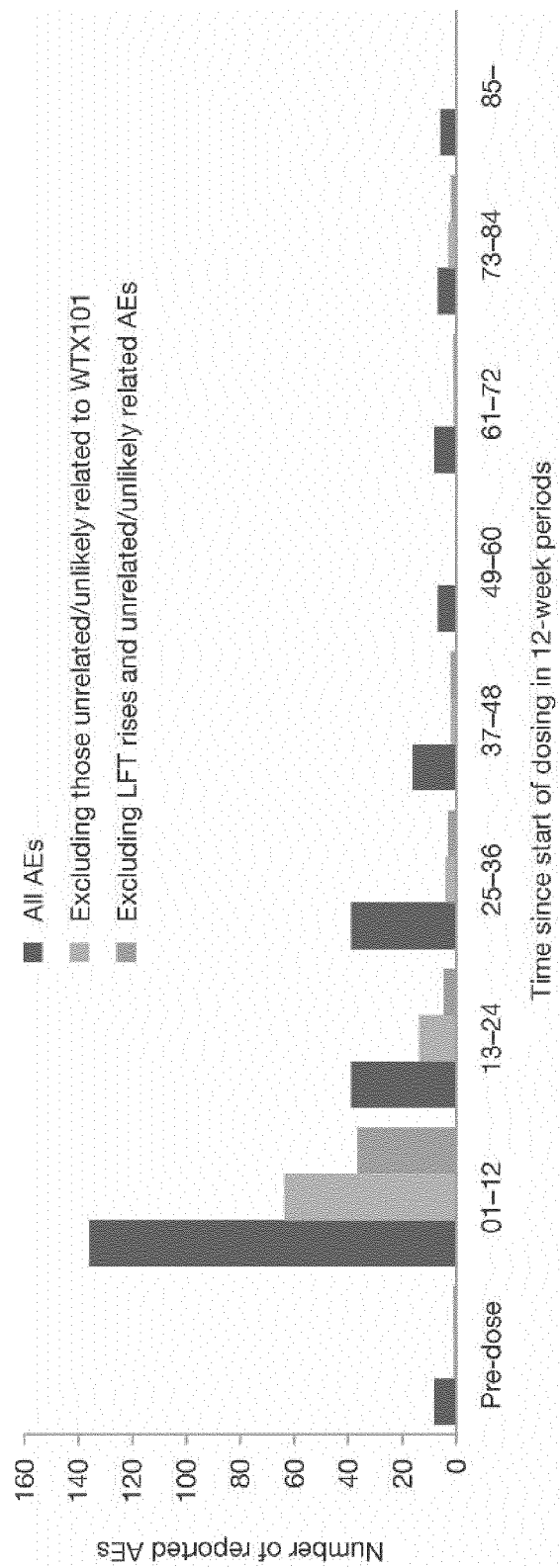
FIG. 7 depicts the Number of reported adverse events (AEs) during the core and extension periods.

WTX101 was generally well tolerated over 72 weeks of treatment. Overall, the number of reported adverse events (AEs) and serious AEs (SAES) decreased by around 50% from weeks 1-24 to weeks 25-72 (FIG. 7, Table 4). Between week 24 and 72, 89% of AEs were mild or moderate, with 89% considered unrelated or unlikely related to therapy.

At baseline, low platelet (56%) and neutrophil (32%) counts were common, with similar reporting throughout follow-up. Most occurrences were not accompanied by low NCC levels and were unlikely to reflect copper deficiency. Over the follow-up period, low hemoglobin was infrequent: 5.2% of measurements fell below the normal range and 7 patients had low hemoglobin at some point but no measurements were below 100 g/L. Two subjects had evidence of neutropenia accompanied by mild anemia and low NCC levels, potentially consistent with copper deficiency at week 36 and 72, respectively; both responded rapidly to dose reduction.

TABLE 4

SAEs during the core and extension periods

| Number of patients with ≥1 SAEs by preferred term reported by the investigator | WTX101 | Relationship to the study drug as deemed by the investigator |
| --- | --- | --- |
| Baseline to week 24 | 11 events in 7 patients | |
| Psychotic disorder | 1 | Unrelated |
| Abnormal behavior | 1 | Unrelated |
| Adjustment disorder | 1 | Unrelated |
| Affective disorder | 1 | Unrelated |
| Mania | 1 | Unlikely |
| Personality disorder | 1 | Unlikely |
| ALT increased | 1 | Possible |
| Hepatic enzyme increased (severe ALT/AST elevation) | 1 | Probable |
| Gait disturbance | 1 | Unlikely |
| Agranulocytosis | 1 | Probable |
| Decline in neurological functioning | 1 | Possible (likely due to disease progression) |
| After week 24 | 6 events in 5 patients | |
| Mania (week 38) | 1 | Unlikely |
| Acute lower back pain (week 37) | 1 | Unrelated |
| Exacerbation of WD* (week 46) | 1 | Possible (likely due to disease progression) |
| Neutropenia† (week 36) | 1 | Possible |
| Dizziness‡ (week 113) | 1 | Possible |
| Loss of consciousness‡ (week 113) | 1 | Possible |

*One patient with a progressive disease course experienced neuropsychiatric exacerbation despite ongoing treatment. Although the SAE was assessed as likely due to WD progression, causality could not be ruled out and the investigator deemed the SAE as possibly related to study drug; the dose was maintained.
†Grade 1 neutropenia normalized with dose reduction.
‡One patient reported feeling lightheaded, dizzy and then fainted and was hospitalized overnight (cause unknown).

Initial improvements in free copper levels, and hepatic and neurological status were preserved or further improved with WTX101 between weeks 24 and 72, demonstrating that once-daily WTX101 provides long-term disease control in WD. WTX101 is well tolerated in patients with WD beyond 24 weeks of treatment. These findings, together with its simple dosing regimen, indicate that WTX101 addresses several unmet needs in the treatment of WD.

Example 3: A Phase 3, Randomised, Rater-Blinded, Multi-Centre Study to Evaluate the Efficacy and Safety of WTX101 Administered for 48 Weeks Versus Standard of Care in Wilson Disease Subjects Aged 18 and Older with an Extension Phase of Up to 60 Months Summary of Study Design A randomised, rater-blinded, multi-centre study assessing the efficacy and safety of an individualised WTX101 dosing regimen administered for 48 weeks, compared to SoC, will be performed in WD subjects aged 18 and older.

Approximately 102 subjects will be enrolled at approximately 5 to 10 North American sites and 15 to 25 sites in the Rest of the World.

Eligible subjects with WD, who have received SoC therapy (i.e., chelation therapy with penicillamine or trientine, Zn therapy, or a combination of both chelation and Zn therapy) for >28 days (Cohort 1), or who are treatment naïve or who have received SoC therapy (i.e., chelation therapy with penicillamine or trientine, Zn therapy, or a combination of both chelation and Zn therapy) for ≤28 days (Cohort 2), will be randomised in a 2:1 ratio to treatment with WTX101 or SoC (either as continued therapy in Cohort 1 or as continued or initial therapy in Cohort 2). Randomisation will be stratified by prior SoC therapy.

Subjects meeting all inclusion and no exclusion criteria will be enrolled into the study and studied as outpatients. Previously treated subjects that are randomised to receive WTX101 will be required to undergo a ≥48-hour washout of prior SoC therapy immediately prior to initiation of treatment with WTX101. Eligible subjects randomised to WTX101 will receive WTX101 as delayed-release tablets for oral administration at doses ranging from 15 mg every other day (QOD) to 60 mg QD. A maximum dose of up to 90 mg QD must be discussed and agreed upon with the Medical Monitor and only if the following criteria are met: $NCC_{corrected}$ is >upper limit of normal (ULN); alanine aminotransferase (ALT) is <2×ULN; and hematological parameters (hemoglobin, platelets, and neutrophils) remain above the thresholds that require dose modification according to Table 1. Efficacy and safety assessments will be performed at scheduled visits, while adverse events and concomitant medications will be monitored continuously throughout the study.

The visit scheme will consist of the Screening Visit, Enrolment Visit, the Treatment Phase, and an End of Study (EOS) (or Early Termination [ET]) Visit. The visit schedule is summarised below.

The Screening Visit will occur within 28 days prior to the Enrolment Visit (Day 1). After the Day 1 Visit, a phone assessment will occur on Week 1, Week 2, Week 30, and Week 42 (Day 8, Day 15, Day 211, and Day 295, respectively) followed by study visits on Week 4, Week 6, Week 8, Week 12, Week 18, Week 24, Week 36, and Week 48 (Day 29, Day 43, Day 57, Day 85, Day 127, Day 169, Day 253, and Day 337, respectively).

Subjects who have completed the 48-week treatment period will be offered the opportunity to participate in an Extension Phase of the study to evaluate the long-term safety and durability of treatment effect of WTX101. If the subject does not choose to participate in this Extension Phase, he/she will be assisted in their transition to SoC for WD under the guidance of their local physician.

The EOS Visit will be conducted at Week 52 (Day 365) only for subjects who do not enter the Extension Phase. For each subject who does not enter the Extension Phase, the main study phase will end approximately 52 weeks (~365 days) after initiation of treatment on Day 1 (48 weeks of treatment with an EOS Visit 4 weeks after the date of last dose). For each subject who enters the Extension Phase, the main study phase will end approximately 48 weeks (Day 337) after initiation of treatment on Day 1.

Dose Modification for Individual Subjects

Specific criteria for temporary interruption of dosing or restriction of dose increases of WTX101 are detailed in Table 5.

TABLE 5

Individual Dose Modification

| Test | Result | Conditions | Action With WTX101 Dosing | Changes in Safety Monitoring[a] | Re-Challenge[b, c] |
|---|---|---|---|---|---|
| ALT | >5 × increase from baseline | ALT above normal range at baseline | Temporary interruption | Contact subject within 48 hours to arrange repeat testing Weekly repeat testing | At 15 mg QD when ALT <2 × increase from baseline |
| | >5 × ULN | ALT within normal range at baseline | Temporary interruption | Contact subject within 48 hours to arrange repeat testing Weekly repeat testing | At 15 mg QD when ALT <2 × ULN |
| | >2 × increase from baseline | ALT above normal range at baseline | Reduce dose to previous dose level if up-titration has occurred or reduce dose to 15 mg QOD if on 15 mg QD. No further dose increase until resolution of Changes in abnormality. | Weekly repeat testing | Not applicable. |
| | >2 × ULN | ALT above normal range at baseline | Reduce dose to previous dose level if up-titration has occurred or reduce dose to 15 mg QOD if on 15 mg QD. No further dose increase until resolution of abnormality. | Weekly repeat testing | Not applicable. |

TABLE 5-continued

Individual Dose Modification

| Test | Result | Conditions | Action With WTX101 Dosing | Changes in Safety Monitoring[a] | Re-Challenge[b, c] |
|---|---|---|---|---|---|
| Hemoglobin | <8 g/dL in the absence of bleeding | None | Temporary interruption | Weekly repeat testing | At 15 mg QD when Hgb and other heme parameters (neutrophils and platelets) are at baseline level. |
| | >30% decrease from baseline | None | Reduce dose to previous dose level if up-titration has occurred or reduce dose to 15 mg QOD if on 15 mg QD. No further dose increase until resolution of abnormality. | Weekly repeat testing | Not applicable. |
| Platelets | <30,000 μL | None | Temporary interruption | Weekly repeat testing | At 15 mg QD when Hgb and other heme parameters (neutrophils and platelets) are at baseline level. |
| | >30% decrease from baseline | Platelets below normal range at baseline | Reduce dose to previous dose level if up-titration has occurred or reduce dose to 15 mg QOD if on 15 mg QD. No further dose increase until resolution of abnormality. | Weekly repeat testing | Not applicable. |
| Neutrophils | $<1.0 \times 10^3/\mu$ | None | Temporary interruption | Weekly repeat testing | At 15 mg QD when Hgb and other heme parameters (neutrophils and platelets) are at baseline level. |
| | >30% decrease from baseline | Neutrophils below normal range at baseline | Reduce dose to previous dose level if up-titration has occurred or reduce dose to 15 mg QOD if on 15 mg QD. No further dose increase until resolution of abnormality. | Weekly repeat testing | Not applicable. |
| Bilirubin | >2 × ULN and ALT >3 × ULN | None | Temporary interruption | Weekly repeat testing | At 15 mg QD when bilirubin below ULN. |

TABLE 5-continued

Individual Dose Modification

| Test | Result | Conditions | Action With WTX101 Dosing | Changes in Safety Monitoring[a] | Re-Challenge[b, c] |
|---|---|---|---|---|---|
| UWDRS Part III neurological examination | ≥4 point increase if baseline <20, ≥6 point increase if baseline ≥20, OR clinically significant signs of neurological worsening | 2 or more time-points, OR clear pattern of worsening | Temporary interruption | Weekly repeat UWDRS testing | At 50% of previous dose when UWDRS has stabilized as demonstrated by 2 consecutive assessments with no increase and after discussion with the Medical Monitor. |

[a]For changes in safety monitoring, weekly repeat testing for laboratory parameters can be completed by a home healthcare nurse if a routine study visit is not scheduled during this time period.
[b]A maximum of 3 re-challenges will be allowed.
[c]For re-challenges, patients who were on 15 mg QOD should be re-challenged at the 15 mg QOD dose.
ALT = alanine aminotransferase; Heme = Hematologic; Hgb = hemoglobin; QD = once daily; QOD = every other day; ULN = upper limit of normal; UWDRS = Unified Wilson Disease Rating Scale.

Two consecutive results (i.e., obtained at 2 consecutive study visits) on pre-specified parameters consistent with toxicity or worsening of specific laboratory parameters or UWDRS Part III, must be obtained for the Dose Modification Criteria to apply. Weekly repeat testing will continue until results are either back to baseline or within normal range limits. Testing will then be repeated 2 weeks later. If results remain at baseline or normal range limits, then per-protocol schedule timings will be reinitiated.

Study Duration

For each subject, the main study phase will end approximately 52 weeks (~365 days) after initiation of treatment on study Day 1 (48 weeks of treatment with an EOS Visit occurring 4 weeks after the date of last dose, if the subject does not enter the Extension Phase). Subjects who have completed the 48-week treatment period will be offered the opportunity to participate in an Extension Phase to evaluate the long-term safety and efficacy of WTX101. If the subject chooses not to participate in the Extension Phase, he/she will be assisted in their transition to SoC for WD under the guidance of their local physician.

If additional clinical evaluation outside of the visit schedule is deemed necessary by the Investigator, or if the subject meets dose modification criteria, then unscheduled visits can occur. Additionally, if there is clear neurological deterioration, as demonstrated by signs or symptoms of neurological worsening, then additional neurological assessments will be performed at the discretion of the Investigator.

All subjects who complete the 48-week period of randomised treatment in WTX101-301 will be offered the opportunity to participate in an up to 60-month open-label Extension Phase in which they will receive WTX101 therapy. The purpose of the Extension Phase is to evaluate the durability and establish long-term safety and efficacy of WTX101. Subjects will only be eligible to remain in the Extension Phase until WTX101 is commercially available within their respective country.

Treatment Groups

Subjects will be treated with 15 mg QOD to 60 mg QD of WTX101 or SoC therapy. Subjects will be randomised to 1 of 2 cohorts: Cohort 1—subjects treated for >28 days with chelation or Zn therapy or a combination of both chelation and Zn therapy, or Cohort 2—subjects who are treatment naïve or have been previously treated with chelation or Zn therapy or a combination of both chelation and Zn therapy for ≤28 days.

Rationale for Dosing

The dose of WTX101 will be adjusted in individual subjects, as appropriate, based on protocol specified guidelines. A detailed dosing guide for WTX101 dose modifications is outlined Table 5.

The WTX101 starting dose is 15 mg QD for all subjects. After 4 weeks, subsequent WTX101 dosing will be individualised. The dosing guidance is based on a variety of factors, including clinical chemistry and hematology, clinical assessment, safety, and $NCC_{corrected}$.

Dose increases are possible at the discretion of the Principal Investigator in 15 mg increments at least 4 weeks apart if the disease is not adequately controlled, taking into account the subject's clinical status and free blood Cu levels, as measured by $NCC/NCC_{corrected}$, and none of the Dose Modification Criteria apply. After dose escalation, subjects will be monitored for adverse events and laboratory assessments every 2 weeks for a 4-week period. If a routine study visit is not scheduled during this time period, a home healthcare nurse may complete these assessments.

When $NCC_{corrected}$ levels have fallen to within the normal range (≤2.3 µmol/L), and the clinical status of the subject is stable or improved for 2 consecutive assessments, WTX101 dosage may be maintained or reduced at the discretion of the Principal Investigator. To avoid over-treatment, the dose may be reduced at any time, at the discretion of the Principal Investigator, guided by the following: if the subject's clinical status indicates possible over-treatment and/or $NCC/NCC_{corrected}$ values are below the normal range. However, the use of $NCC_{corrected}$ as a criterion for dose adjustment is optional, reflecting the different clinical practice across sites in the global study. The dose should be lowered or interrupted if any of the Dose Modification Criteria are met.

Study Drug Administration

WTX101 will be provided as tablets containing 15 mg of bis-choline tetrathiomolybdate for oral administration.

WTX101 will be administered at doses ranging from 15 mg QOD to 60 mg QD. A maximum dose of up to 90 mg QD must be discussed and agreed upon with the Medical Monitor and only if the following criteria are met: $NCC_{corrected}$ is >ULN; ALT is <2×ULN; and hematological parameters (hemoglobin, platelets, and neutrophils) remain above the thresholds that require dose modification according to Table 1.

WTX101 will be administered for the 48-week treatment period QD or QOD (dosed in the morning), in the fasted state (1 hour before or 2 hours after meals). Additionally, details on WTX101 administration are included below.

Individualised WTX101 dosing will be utilised throughout the study based on the following parameters: Clinical criteria: dose-titration based on hepatic and neurological status; $NCC_{corrected}$: dose-titration instructed based on NCC levels adjusted for the amount of Cu bound to the WTX101 TPC; and Safety monitoring: dose modification criteria are based on regularly scheduled assessments for recognised hematological effects of Cu lowering, hepatic testing, and neurological testing.

The WTX101 dose may also be lowered should an adverse event occur which requires a dose reduction. Dosing guidance associated with specific events is provided in the Dose Modification Criteria (Table 5); dose reductions for other events will be handled by the site Principal Investigator (or Sub Investigator, if appropriate) on a case-by-case basis in collaboration with the Medical Monitor.

In all subjects, WTX101 will be administered at a 15 mg QD starting dose on Day 1 continuing for the first 4 weeks. After 4 weeks, up-titration to 30 mg QD may be performed at the discretion of the Principal Investigator, if the disease is not adequately controlled, taking into account the subject's clinical status and free blood Cu levels, as measured by $NCC/NCC_{corrected}$, and none of the Dose Modification Criteria apply. Further dose increases are possible at the discretion of the Principal Investigator in 15 mg increments at least 4 weeks apart following the same aforementioned criteria.

When $NCC_{corrected}$ levels have fallen to within the normal range (<2.3 µmol/L), and/or the clinical status of the subject is stable or improved for 2 consecutive assessments, WTX101 dosage may be maintained or reduced at the discretion of the Principal Investigator. To avoid over-treatment, the dose may be reduced at any time, at the discretion of the Principal Investigator, guided by the following: if the subject's clinical status indicates possible over-treatment and/or $NCC/NCC_{corrected}$ values are below the normal range. However, the use of $NCC_{corrected}$ as a criterion for dose adjustment is optional, reflecting the different clinical practice across sites in the global study. The dose should be lowered or interrupted if any of the Dose Modification Criteria are met.

The expected maximum dose is 60 mg QD, but higher doses may be considered on a case-by-case basis in collaboration with the Medical Monitor. A maximum dose of up to 90 mg QD must be discussed and agreed upon with the Medical Monitor and only if the following criteria are met: $NCC_{corrected}$ is >ULN; ALT is <2×ULN; and hematological parameters (hemoglobin, platelets, and neutrophils) remain above the thresholds that require dose modification according to Table 5.

For accuracy in measurements, the following parameters are followed. Oestrogens may interfere with biliary Cu excretion. Vitamin E has been used as an adjunctive therapy in WD treatment regimens. Subjects must not use vitamins and/or minerals containing Cu, Zn, or Mo. Gadolinium- and iodine-containing contrast media are known to interfere with tests on Mo. Gadolinium- and iodine-containing contrast media are requested not to be used within the 96 hours prior to Mo testing. Barium-containing contrast media are known to interfere with tests on Cu. Barium-containing contrast media are requested not to be used within the 96 hours prior to Cu testing. Subjects should avoid intake of foods and drinks with high contents of Cu throughout the study duration.

Following randomisation and washout (if applicable), subjects will return for visits and procedures: the Week 1 to Week 30 Visits and Week 42 Visit will occur within ±3 days of the scheduled time; the Week 36 and Week 48 Visit will occur within ±7 days of the scheduled time.

Efficacy Assessments

The primary efficacy assessment will be control of free Cu, measured as the percent change from baseline (Day 1) to 48 weeks in NCC levels. For WTX101-treated subjects, the NCC level will be corrected for the amount of Cu bound to the WTX101 Tripartite Complex (TPC).

The secondary efficacy assessments include the following: Hepatic status using the MELD score; Disability using UWDRS Part II; Neurological status using UWDRS Part III; Clinical status using Clinical Global Impression Scale (scale items 1 and 2); and NCC responder rate.

The tertiary efficacy assessments include the following: Individualised assessment of each subject's 3 most troublesome symptoms; Hepatic fibrosis using the FIB-4 Index and transient elastography; Hepatic status using the Modified Nazer Score; Psychiatric symptoms using the BPRS-24; and QoL/PRO endpoint measures using EQ-5D and TSQM-9. Exploratory efficacy assessments include the following:

Evaluations of Cu control using exploratory measures of total Cu, free Cu, PUF-Cu, and Cu speciation of plasma; Evaluation of Mo plasma levels; Evaluation of 24-hour urinary Cu and urinary Mo; Evaluation of the timed 25F Walk Test; Evaluation of the 9-HPT; Evaluation of the non-verbal Stroop Interference Test; and Evaluation of the Digit Span Test.

Statistics

All statistical analyses will be performed according to art-recognized procedures. A general description of the statistical methods to be used to analyse the efficacy and safety data is outlined below. Statistical analyses will be carried out using SAS®, Version 9.3 or later, SAS Institute, Cary, N.C., USA.

The primary endpoint is Cu control assessed as the percent change from baseline to 48 weeks in NCC levels; for WTX101-treated subjects, the NCC level will be corrected for the amount of Cu bound to the WTX101 TPC.

The percentage change from baseline in the NCC level will be analysed using mixed model repeated measures (MMRM) analysis stratified by cohort and prior SoC therapy. The change from baseline at Week 4, Week 8, Week 12, Week 24, Week 36, and Week 48 will be included. The Restricted Maximum Likelihood estimation will be used. The model will be stratified by cohort and prior SoC therapy. To better normalise the data, NCC may be log transformed prior to analysis. Fixed-effect terms will be included for randomised treatment (WTX101 or SoC), visit and randomised treatment by visit interaction, and baseline NCC level as a covariate. The treatment by visit interaction will remain in the model regardless of significance. An unstructured covariance matrix will be used to model the within-subject error and the Kenward-Roger approximation will be used to estimate the degrees of freedom. If the fit of the unstructured covariance structure fails to converge, the following covariance structures will be tried in order until convergence is reached: toeplitz with heterogeneity, autogressive with heterogeneity, toeplitz, and autoregressive. The principal contrast of interest will be between WTX101 versus SoC-treated subjects at Week 48. Model-based estimates of the difference between randomised treatments in mean percent change in the NCC level at Week 48, along with a 2-sided 95% confidence interval (CI) and p-value will be provided. If the lower 2-sided 95% CI excludes a difference of −15%, then non-inferiority will be concluded in the overall study population for WTX101 in relation to SoC; and if the lower 2-sided 95% CI excludes a difference of 0%, then superiority will be concluded in the overall study population for WTX101 over SoC. The least-squares (LS) mean changes from baseline and associated standard errors (SEs) at earlier time points (i.e., Week 4, Week 8, Week 12, Week 24, and Week 36) will be extracted and presented graphically by arm over time.

The supportive analysis of the primary endpoint within Cohort 1 will mirror that described for the overall population analysis except that the analysis will no longer be stratified for cohort.

The percentage change from baseline in NCC level will be analysed descriptively using MMRM analysis; there will be no formal statistical comparison made between the randomised treatment arms. The percentage change from baseline at Week 4, Week 8, Week 12, Week 24, Week 36, and Week 48 will be estimated using the same model terms as described for the analysis of Cohort 1 subjects. The principal output of interest will be the LS mean, SE, and p-value for the percent change from baseline in NCC level at Week 48 within each. Within arm LS mean changes and SEs from baseline earlier time points (i.e., Week 4, Week 8, Week 12, Week 24, and Week 36) will be extracted and presented graphically by arm over time.

The secondary efficacy endpoints include the following: Change from baseline in hepatic status at 48 weeks assessed by the MELD score; Change from baseline to 48 weeks in the UWDRS Part II score; Change from baseline to 48 weeks in the UWDRS Part III score; Change from baseline to 48 weeks in the CGI-I and CGI-S; and NCC responder rate at 48 weeks.

Secondary efficacy endpoints will be analysed in the same manner as the primary endpoint, via a cohort-stratified MMRM analysis with the principal contrast being between SoC versus WTX101-treated subjects at Week 48. A supportive, comparative analysis will also be performed in Cohort 1 subjects and a supportive, descriptive within arm analysis will be performed in Cohort 2 subjects. For endpoints b, c, and d, total scores will be analysed.

NCC response is defined as the proportion of subjects who achieve or maintain normalised levels of NCC or $NCC_{corrected}$ (0.8 µM to 2.3 µM) or reach a reduction of at least 25% in NCC or $NCC_{corrected}$ at 48 weeks. For WTX101-treated subjects, the NCC level will be corrected for the amount of Cu bound to the WTX101 TPC.

Subjects without 48-week values will be considered as non-responders. These data will be analysed via cohort-stratified logistic regression with terms for randomised treatment and baseline NCC level. Again, a supportive, comparative analysis will be performed in Cohort 1 subjects and a supportive, descriptive within arm analysis will be performed in Cohort 2 subjects.

Example 4: Absorption of Bis-Choline Tetrathiomolybdate after Single Dose Administration of an Enteric-Coated Formulation with and without Food and a Non-Coated Formulation Co-Administered with a Proton Pump Inhibitor without Food A single-center, open-label, randomized, 3-period, 3-treatment, 6-sequence crossover study evaluating the PK (pharmacokinetics) of single doses of bis-choline tetrathiomolybdate in healthy subjects based on the measurement of plasma total Mo concentration was conducted. Eighteen (18) healthy, non-tobacco using adult male and female subjects underwent Treatment A, B, or C over the course of 3-periods as described in the Study Diagram shown in FIGS. 8A and 8B. Subjects received each treatment on one occasion. Subjects were randomized to one of the following six treatment sequences: ABC, ACB, BAC, BCA, CAB, and CBA. All study medications were taken orally with approximately 240 mL of water. Subjects were instructed not to crush, split, or chew the study medication.

Treatment A: 60 mg bis-choline tetrathiomolybdate (2×bis-choline tetrathiomolybdate enteric coated (EC) tablets, 30 mg, see Table 6) at Hour 0 on Day 1, following an overnight fast.

Treatment B: 60 mg bis-choline tetrathiomolybdate (2×bis-choline tetrathiomolybdate 1 EC tablets, 30 mg) at Hour 0 on Day 1, 30 minutes after the start of a high-fat breakfast, preceded by an overnight fast.

Treatment C: 20 mg omeprazole (1×20 mg delayed-release capsule of a PPI (proton pump inhibitor)) QD in the morning of Days −5 to −1 following an overnight fast, 20 mg omeprazole delayed-release capsule at Hour −1 on Day 1 following an overnight fast, and 60 mg bis-choline tetrathiomolybdate (2×bis-choline tetrathiomolybdate uncoated (UC) capsules, 30 mg. See Table 7) at Hour 0 on Day 1.

TABLE 6

| Component | Quality Standard | Function | Composition (per Tablet Strength) | |
|---|---|---|---|---|
| | | | 10 mg | 30 mg |
| WTX101 | In-house | Active substance | 10 mg | 30 mg |
| Tribasic calcium phosphate | NF | Diluent | 81 mg | 79.2 mg |
| Sodium carbonate, anhydrous | NF | Buffer | 5.0 mg | 6.0 mg |
| Sodium starch glycolate | NF | Disintegrant | 2.0 mg | 2.4 mg |
| Magnesium stearate | NF | Lubricant | 2.0 mg | 2.4 mg |
| OPADRY ® Complete Film Coating System 03K19229 Clear | In-house | Pre-coat | 6.0 mg | 7.2 mg |
| Acryl-EZE White | In-house | Enteric coat | 7.7 mg | 8.9 mg |

TABLE 7

| Component | Quality Standard | Function | Composition (per capsule) |
|---|---|---|---|
| WTX101 | In-house | Active substance | 30 mg |
| Anhydrous dibasic calcium phosphate | USP | Diluent | 475 mg |
| Anhydrous sodium carbonate | NF | Buffer | 25 mg |
| Hydroxypropylmethylcellulose capsules (Size 1) | In-house | Capsule | 1 capsule |

All 18 subjects who were enrolled and completed the study were included in the safety and PK analysis. However, one subject was excluded from the PK descriptive statistics and statistical analyses for Treatment B due to a measurable predose plasma total Mo concentration>40% of the corresponding $C_{max}$ (maximum measured plasma concentration). The PK analysis population was therefore comprised of 18 subjects for the EC Tablet Fasted (Treatment A) and the UC+PPI Fasted (Treatment C) and 17 subjects for the EC Tablet Fed (Treatment B).

Pharmacokinetic Results

PK parameters for plasma total Mo were calculated as follows:

$AUC_{0-t}$: The area under the plasma concentration versus time curve, from time 0 to the last measurable concentration, as calculated by the linear trapezoidal method.

$AUC_{0\_inf}$: The area under the plasma concentration versus time curve from time 0 to infinity. $AUC_{0-inf}$ is calculated as the sum of $AUC_{0-t}$ plus the ratio of the last measurable plasma concentration to the elimination rate constant.

$C_{max}$: Maximum measured plasma concentration over the time span specified.

$t_{max}$: Time of the maximum measured plasma concentration. If the maximum value occurred at more than one time point, $t_{max}$ was defined as the first time point with this value.

$\lambda z$: Apparent first-order terminal elimination rate constant calculated from a semi-log plot of the plasma concentration versus time curve. The parameter was calculated by linear least-squares regression analysis using the maximum number of points in the terminal log-linear phase (e.g., 3 or more non-zero plasma concentrations), beginning with the last non-zero concentration.

$t\frac{1}{2}$: Apparent first-order terminal elimination half-life was calculated as $0.693/\lambda z$.

$T_{lag}$: Absorption lag time

CL/F: Apparent oral clearance

Vz/F: Apparent oral volume of distribution

Figures 8A, 8B:
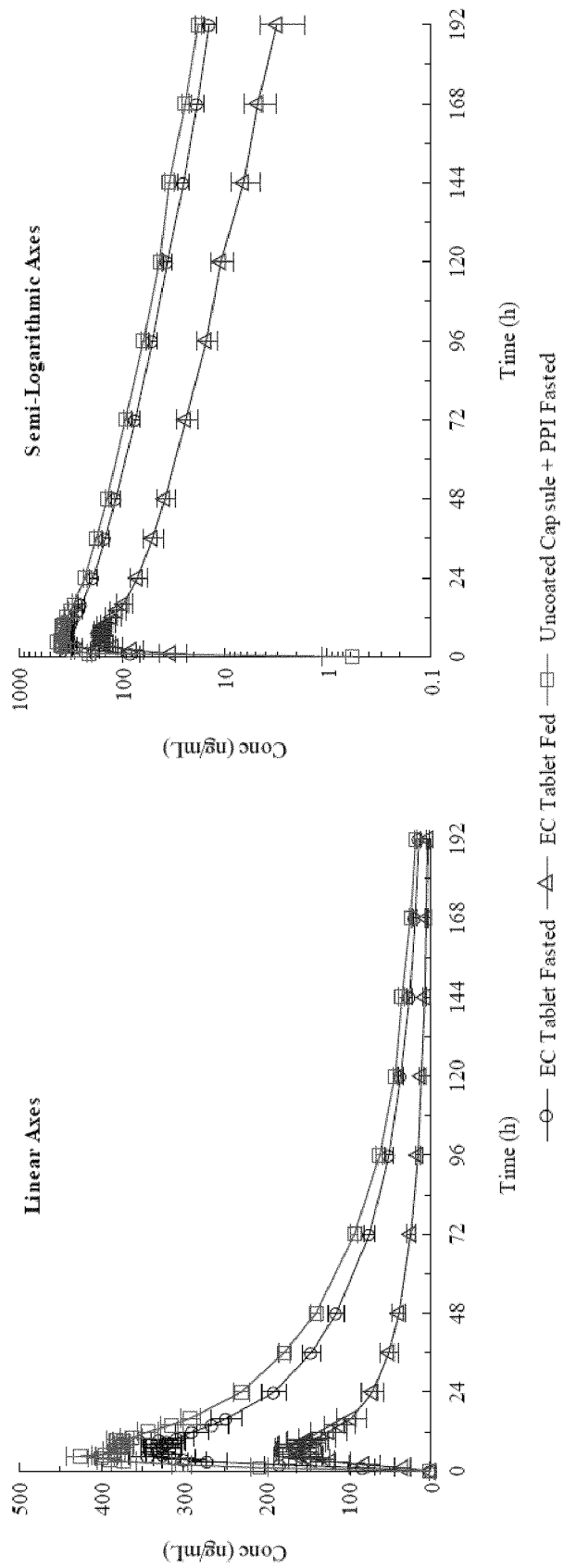
FIGS. 8A-8B depicts Mean±Standard Error plasma concentrations of total Mo after administration of a single 60 mg (2×30 mg) dose of WTX101 EC tablets under fasted (Treatment A) and fed conditions (Treatment B) and UC+PPI under fasted conditions (Treatment C). Data is plotted on linear axes (FIG. 8A) and semi-logarithmic (FIG. 8B).

As shown in FIGS. 8A and 8B, the mean±standard error plasma concentrations of total Mo were slightly lower after administration of the EC Tablet Fasted (Treatment A) compared to the uncoated capsules (UC)+PPI Fasted (Treatment C). There was, however, variability among subjects, with 3 of the 18 showing much lower concentrations for the EC Tablet, 5 showing the same pattern as the mean data, and 10 showing more comparable or superimposable concentrations for both treatments.

Consistent with the mean plasma concentrations, the arithmetic (Table 8) and geometric (Table 7) mean values for $C_{max}$, $AUC_{0-t}$, and $AUC_{inf}$ were lower for the EC Tablet Fasted (Treatment A) than for the UC Capsule+PPI Fasted (Treatment C). The GMRs ranged from 75.81% to 87.16%, with lower limits of the associated 90% CIs<80.00% (Table 9), indicating a decrease in exposure on the average. The median $T_{max}$ was comparable for both treatments, 4.54 and 4.50 hours, respectively, with comparable ranges (Table 8).

Four (4) of the 18 subjects had an absorption lag time after administration of the EC Tablet Fasted, with a median (range) of 2.00 hours (2.00 to 3.00 hours) (Table 8).

Administration of the EC Tablet with food (Treatment B) resulted in a large decrease in the mean plasma total Mo concentrations (FIG. 5). This was also observed in all but 2 of the 17 subjects evaluable for this treatment. $C_{max}$, $AUC_{0-t}$, and $AUC_{inf}$ were lower after administration of the EC Tablet with food (Tables 4 and 5), with GMRs ranging from 25.20% to 40.49%, indicating a substantial decrease in absorption. The median $T_{max}$ was comparable with and without food, 4.55 and 4.54 hours, respectively, with comparable ranges (Table 8). Compared to the EC Tablet Fasted (Treatment A), more subjects (6 subjects) had an absorption lag time and increase in the median (range) to 3.00 hours (2.00 to 5.00 hours) (Table 8).

The mean $t_{1/2}$ was essentially the same for all 3 treatments (Table 8), with an overall mean of ~48 hours or 2 days. CL/F and Vz/F were also comparable for the 2 fasted treatments but, due to the lower bioavailability after administration of the EC Tablet Fed, are higher for that treatment.

The lowest between-subject coefficients of variation (BSCV) for $C_{max}$, $AUC_{0-t}$, and $AUC_{inf}$ were observed for the UC capsule+PPI Fasted (Treatment C), with values ranging from 15.8% to 19.1% (Table 8). Administration of the EC Tablet Fasted (Treatment A) resulted in higher BSCVs (26.1% to 35.2%; Table 8). The BSCVs were much higher, particularly for $AUC_{0-t}$ and $AUC_{inf}$—81.5% and 72.6%, respectively, (Table 8)—when the EC Tablet was administered after the high-calorie/high-fat meal. Compared to the EC Tablet Fasted, the BSCVs for the AUCs were ~2.2-fold higher when the EC Tablet was administered under fed conditions.

As illustrated in FIGS. 8A and 8B, there was a slight decrease in the mean±standard error plasma concentrations of total Mo after administration of the EC Tablet Fasted (Treatment A) compared to the UC+PPI fasted (Treatment C). Similar trends were observed with respect to $C_{max}$, $AUC_{(0-t)}$, and $AUC_{(inf)}$ (Tables 6 and 7). Nevertheless, examination of the individual subject data indicates that while a similar pattern was observed with some of the individual subjects, the majority had a total Mo concentration-time profile that was comparable for the bis-choline tetrathiomolybdate EC Tablet and bis-choline tetrathiomolybdate UC+PPI when both were administered under fasted conditions. However, administration of the bis-choline tetrathiomolybdate EC Tablet fed (Treatment B) resulted in a 60% to 75% decrease in absorption which was consistent among the majority of subjects.

TABLE 8

Summary of Total Mo PK Parameters After Administration of a Single 60 mg (2 × 30 mg) Dose of WTX101 EC Tablets Under Fasted (Treatment A) and Fed Conditions (Treatment B) and UC + PPI Under Fasted Conditions (Treatment C)

| | Treatment | | |
|---|---|---|---|
| Parameter* | EC Tablet Fasted | EC Tablet Fed | UC + PPI Fasted |
| $T_{lag}$ (h) | 2.00 (4) [2.00-3.00] | 3.00 (6) [2.00-5.00] | —† |
| $C_{max}$ (ng/mL) | 376 ± 98.0 (18) | 187 ± 118 (17) | 442 ± 69.6 (18) |
| $T_{max}$ (h) | 4.54 (18) [3.00-9.53] | 4.55 (17) [3.52-9.51] | 4.50 (18) [2.99-10.0] |

TABLE 8-continued

Summary of Total Mo PK Parameters After Administration of a Single 60 mg
(2 × 30 mg) Dose of WTX101 EC Tablets Under Fasted (Treatment A) and Fed Conditions
(Treatment B) and UC + PPI Under Fasted Conditions (Treatment C)

| | Treatment | | |
|---|---|---|---|
| Parameter* | EC Tablet Fasted | EC Tablet Fed | UC + PPI Fasted |
| $AUC_{(0-t)}$ (h × ng/mL) | 16,026 ± 5,635 (18) | 5,740 ± 4,681 (17) | 19,809 ± 3,509 (18) |
| $AUC_{(inf)}$ (h × ng/mL) | 17,258 ± 5,955 (18) | 6,973 ± 5,065 (15) | 21,047 ± 4,022 (17) |
| $\lambda z$ (1/h) | 0.0140 ± 0.0023 (18) | 0.0258 ± 0.0303 (15) | 0.0145 ± 0.0014 (17) |
| $t^{1/2}$ (h) | 51.0 ± 8.87 (18) | 43.5 ± 20.9 (15) | 48.2 ± 4.86 (17) |
| CL/F (L/h) | 0.92 ± 0.51 (18) | 6.34 ± 11.9 (15) | 0.66 ± 0.13 (17) |
| Vz/F (L) | 66.6 ± 34.0 (18) | 175 ± 98.1 (15) | 45.2 ± 8.31 (17) |

*Arithmetic mean ± standard deviation (N) except for $T_{max}$ for which the median (N) [Range] is reported
†Parameter could not be estimated for any subject for this treatment.

TABLE 9

Statistical Analysis of Total Mo PK Parameters After Administration of a Single 60 mg
(2 × 30 mg) Dose of WTX101 EC Tablets Under Fasted (Treatment A) and Fed Conditions
(Treatment B) and UC + PPI Under Fasted Conditions (Treatment C)

| | Least Squares Geometric Means | | Geometric Mean Ratio (%)* | | Within-Subject |
|---|---|---|---|---|---|
| Parameter | Test | Reference | Estimate | 90% Confidence Interval | CV (%) |
| EC Tablet Fasted vs. UC +PPI Fasted | | | | | |
| Cmax | 360.88 | 436.61 | 82.65 | 63.91 → 106.90 | 47.98 |
| AUC(0-t) | 14,790.84 | 19,511.14 | 75.81 | 52.23 → 110.02 | 73.76 |
| AUC(inf) | 15,997.76 | 18,353.45 | 87.16 | 64.59 → 117.63 | 55.30 |
| EC Tablet Fed vs. EC Tablet Fasted | | | | | |
| Cmax | 146.11 | 360.88 | 40.49 | 31.12 → 52.68 | 47.98 |
| AUC(0-t) | 3,726.71 | 14,790.84 | 25.20 | 17.21 → 36.89 | 73.76 |
| AUC(inf) | 5,071.14 | 15,997.76 | 31.70 | 23.12 → 43.47 | 55.30 |

*Based on analysis of natural log-transformed data.

TABLE 10

Summary of Between-Subject Coefficients of Variation of
Total Mo $C_{max}$, $AUC_{0-t}$, and $AUC_{inf}$ After Administration
of a Single 60 mg (2 × 30 mg) Dose of WTX101 EC Tablets
Under Fasted (Treatment A) and Fed Conditions (Treatment B)
and UC + PPI Under Fasted Conditions (Treatment C)

| | Treatment | | |
|---|---|---|---|
| Parameter* | EC Tablet Fasted | EC Tablet Fed | UC + PPI Fasted |
| Cmax (ng/mL) | 26.1 | 39.9 | 15.8 |
| AUC(0-t) (h × ng/mL) | 35.2 | 81.5 | 17.7 |
| AUC(inf) (h × ng/mL) | 34.5 | 72.6 | 19.1 |

*Between subject coefficient of variation (%).

Example 5: Neurological Improvement with WTX101 Treatment in a Phase 2, Multi-Center, Open Label Study in Wilson Disease The data collected during the Phase 2 study described in Example 1 was further analyzed to characterize the specific neurological changes after 24 weeks' treatment with WTX101.

Methods

Adult patients with WD (treatment naïve or ≤2 years with chelation or zinc therapy) received response-guided individual WTX101 dosing (15-120 mg once daily) for 24 weeks. Changes in neurological status were characterized using the Unified Wilson's Disease Rating Scale (UWDRS).

Results

Of the 28 enrolled patients, 25 had neurological manifestations. Baseline mean UWDRS Part II (disability) and III (neurological status) scores were 6.6 (SD 10.0; range 0-35) and 22.8 (SD 21.0; range 0-83), respectively. By week 24, both mean [SD] UWDRS Part II score (4.1 [8.2]; p<0.001) and Part III score (16.6 [17.7]; p<0.0001) improved. There was a highly significant predictive relationship between Parts II and III total scores taken over time (p<0.0001). Most common UWDRS Part III abnormalities at baseline were postural arm tremor (71%), dysarthria (68%), gait (61%) and limb dexterity and coordination scale items e.g. alternating hand movements (71%), finger taps (57%), handwriting (54%) and leg agility (54%). Most severely affected items were handwriting and dysarthria (mean [SD] scores 2.0 [0.8] and 1.8 [0.9], respectively). Largest mean improvements (% change) over 24 weeks were observed for handwriting (51.4%), leg agility (40.8%), postural arm tremor (39.5%) and alternating hand movements (35.0%). Grouping total tremor or limb dexterity and coordination items demonstrated similar improvements (34.2% and 29.2%, respectively). WTX101 was generally well tolerated and early drug-induced neurological worsening was not observed.

Conclusions

Neurological manifestations were common in this patient cohort with WD. WTX101 treatment rapidly improved disability and neurological status in a prospective 24-week Phase 2 trial in WD. Improved neurological status after WTX101 treatment correlated with reduced patient-reported disability.

Example 6: Neurological Improvement with WTX101 Treatment in a Phase 2, Multi-Center, Open Label Study in Wilson Disease The Phase 2 study of Example 1 was further analyzed to characterize the particulars of the neurological manifestations in Wilson Disease (WD) patients and the specific neurological changes after 24 weeks' treatment with WTX101. Analysis of this data was performed generally as described in Example 5.

Although neurological manifestations can very quickly become disabling, previously existing treatments did not always alleviate symptoms, sometimes caused the well-known paradoxical early worsening of the neurological disease, and/or were poorly tolerated by the patients. Bischoline tetrathiomolybdate (WTX101) in a 24-week, phase 2 study (NCT02273596; EudraCT 2014-001703-41), showed rapid control of non-ceruloplasmin-bound copper (NCC) levels and a favorable safety profile where the mean NCC level fell below the upper limit of normal by week 12.

Analysis of neurological manifestations, assessed using the unified Wilson's disease rating scale (UWDRS), showed improved symptoms without paradoxical early worsening. Changes in neurological manifestations in the study were scrutinized using data from part III (neurological status) of the UWDRS. Additionally, this Example explores the quantitative relationship between patient reported (part II) and clinically assessed (part III) neurological manifestations of Wilson disease.

Methods

Adults (aged≥18 years) diagnosed with Wilson disease (Leipzig score≥4) were included if they had received no previous treatment for Wilson disease, or had received chelation or zinc therapy for ≤24 months; and had an NCC concentration above the lower limit of the normal reference range (i.e. ≥0.8 µmol/L). Patients were excluded if they had decompensated hepatic cirrhosis, a model for end-stage liver disease (MELD) score>11, or a modified Nazer score (revised King's score)>6.

The 24-week, phase 2, open-label study was conducted in Europe and the USA. During the first 4-8 weeks, patients received WTX101 15-60 mg once daily, depending on baseline NCC concentrations adjusted for plasma molybdenum (except at baseline). Thereafter, dosing was tailored according to laboratory (including NCC concentrations adjusted for plasma molybdenum) and clinical assessments (maximum daily dose administered: 120 mg).

Disability and neurological status were assessed using parts II and III, respectively, of the UWDRS at baseline and weeks 4, 8, 12, 18, and 24: Disability (part II): 10-item patient-reported questionnaire (range for total scores: 0-40; higher scores indicate greater disability). Neurological status (part III): 23-item clinician-assessed score (range for total scores: 0-143; higher scores indicate worse neurological status). Data (total scores for UWDRS parts II and III, and AEs) are summarized briefly for context in Results.

The relationship between disability and neurological status total scores was examined to better understand and quantify the impact of treatment on neurological manifestations in order to provide optimal treatment regimens while minimizing AEs. UWDRS neurological status scores at baseline, week 24, and change from baseline to week 24 were calculated for: any individual item experienced by at least 50% of patients; and for item groups (i.e. collections of individual items that could be considered to represent particular patient phenotypes [Table 11]).

TABLE 11

Composition of UWDRS neurological item groups

| Item group | Individual neurological status items assigned to group (UWDRS item number) | Range for total score[b] |
|---|---|---|
| Total tremor | Resting tremor (15); head tremor (16); arms—postural tremor (21A) and wing-beating tremor (21B); postural tremor—legs (24); jaw tremor (31) | 0-45 |
| Total gait | Arising from chair (27); posture—trunk dystonia (28A[a]), ataxia of stance (28B), and parkinsonism (28C); gait—leg dystonia (29A[a]), ataxia (29B), and parkinsonism (29C) | 0-32 |
| Dystonia | Oromandibular dystonia (13A); cervical dystonia (25); arm and hand dystonia (26); trunk dystonia (28A[a]); gait—leg dystonia (29A[a]) | 0-28 |
| Limb agility and coordination | Finger taps (18); rapid alternate hand movements (19); handwriting (20); finger-to-nose test (22); leg agility (23) | 0-36 |
| Rigidity | Arms, legs, and neck (17) | 0-20 |

[a]Individual sub-item is not unique to one group;
[b]scores for individual items are summed to give a total score for the item group.

Least-squares mean (standard error [SE], 95% confidence intervals [CIs]) values were calculated for changes from baseline for UWDRS total scores using a mixed-model repeated-measures analysis; significance was assessed using two-sided p values. To investigate and quantify the relationship between UWDRS total scores for parts II and III, a random coefficients analysis was conducted using each patient's scores from all study visits. Summary statistics were calculated for other outcomes.

Results

In total, 28 patients received WTX101 (Table 12). Six patients discontinued treatment. Three experienced AEs of a non-neurological nature, two had psychiatric difficulties and could not adhere to the protocol, and one had neurological worsening due to disease progression.

TABLE 12

Baseline characteristics

| | Patients (N = 28) |
|---|---|
| Women, n (%) | 15 (54) |
| Age, years, mean (SD) [range] | 34.1 (11.86) [18-64] |
| UWDRS total scores, mean (SD) | |
| Part II (disability) | 6.6 (10.0) |
| Part III (neurological status) | 22.8 (21.0) |
| Neurological abnormalities[a], n (%) | 25 (89) |
| Previous treatment for Wilson disease, n (%) | |
| None | 9 (32) |
| Less than 28 days | 9 (32) |
| Between 28 days and 2 years | 10 (36) |

[a]Patients with a UWDRS part III score of ≥1 at baseline.

UWDRS Disability and Neurological Status: Total Scores

Mean (SD) total scores were improved at week 24: 4.1 (8.2) for disability and 16.6 (17.7) for neurological status. Improvements were significant in both cases (least-square mean [SE, 95% CI] change from baseline): −3.7 (0.9; −5.5 to −1.8; p=0.0003) for disability and −8.7 (1.9; −12.5 to −5.0; p<0.0001) for neurological status. There was a significant positive linear relationship between UWDRS part II and part III total scores (p<0.0001).

UWDRS Neurological Status: Individual Items and Item Groups

Baseline

Figure 9:
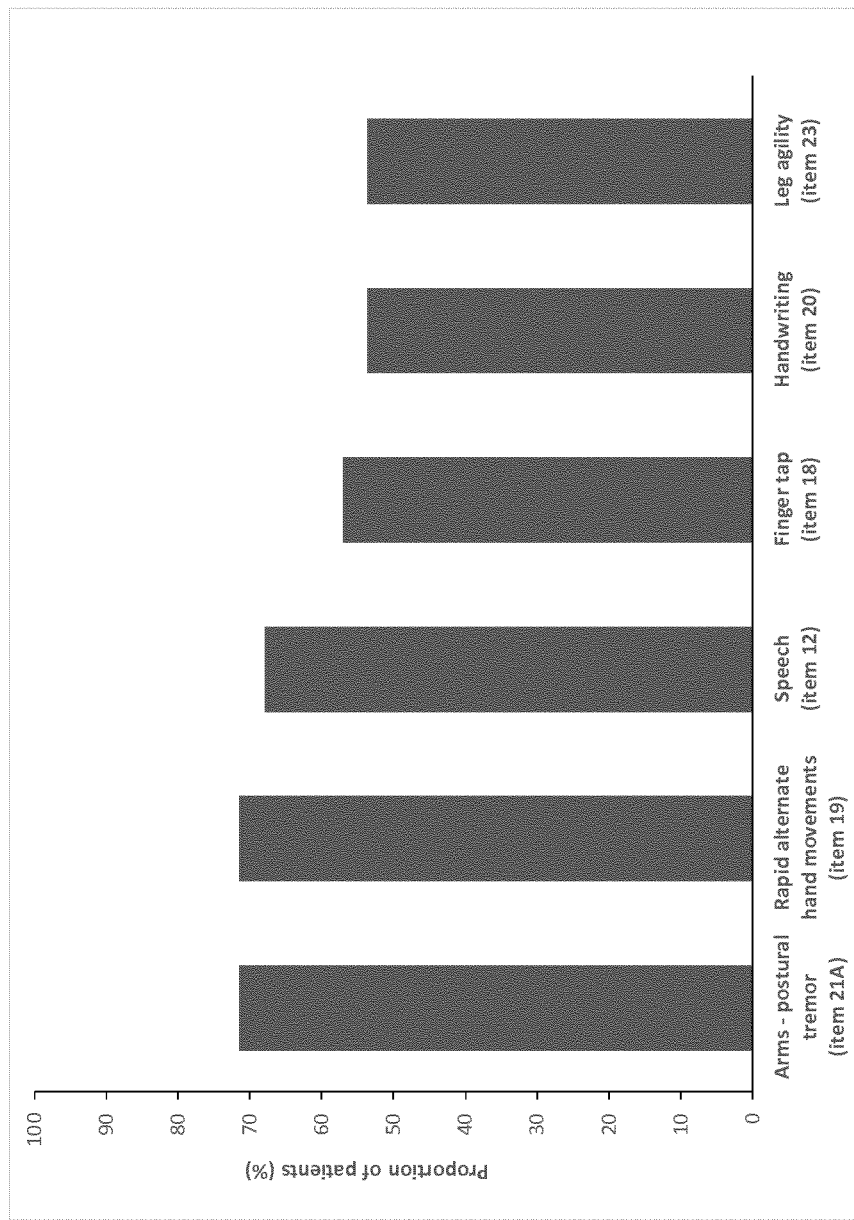
FIG. 9 depicts UWDRS neurological status (part III) symptoms experienced by at least 50% of patients at baseline. Data are expressed as a percentage of patients in the enrolled population (N=28).

Individual items: of six items affecting at least 50% of patients, postural arm tremor, rapid alternating hand movements, and dysarthria (speech) were the most common (FIG. 9). Allowing for differences in maximum possible scores among items (i.e. 4 or 8), handwriting and speech were the most severely affected (FIGS. 10A and 10B).

Item groups: tremor was reported for the greatest proportion of patients (23 patients, 82%), followed by gait (17, 61%), dystonia (15, 54%), limb agility and coordination (15, 54%), and rigidity (12, 43%). Allowing for differences in maximum possible scores among item groups (Table 11), rigidity was the most severely affected (mean [standard deviation, SD] score: 3.5 [2.9]), followed by tremor (7.4 [7.0]), dystonia (3.9 [4.4]), gait (4.4 [4.1]), and limb agility and coordination (1.3 [0.5]).

Changes from Baseline to Week 24

Individual items: Based on descriptive statistics, mean percentage improvements were greatest for handwriting and leg agility (FIGS. 11A and 11B) and few patients showed any deterioration in scores (FIG. 12). Two patients had a 2-point deterioration (finger taps); all other deteriorations were by 1 point.

Item groups: improvements for tremor (mean [SD], 34.2% [61.7]) and limb agility and coordination (29.2% [72.2]) were generally similar to those for individual items. Of 22 patients in the analyses, four and three, respectively, showed any deterioration in scores. (deterioration of 1 point in five cases, 3 points in one case [tremor] and 4 points in one case [limb agility and coordination]). Overall deteriorations for rigidity (26.9% [169.6]), dystonia (15.0% [135.2]), and gait (4.2% [77.8]) were attributable to four, three, and six individuals, respectively (deteriorations between 1 and 8 points for rigidity, 2 and 4 points for dystonia, and 1 and 6 points for total gait).

Conclusions

The phase 2 study showed that WTX101 treatment has the potential to address important unmet needs in Wilson disease. Improved neurological status after WTX101 treatment correlated with reduced patient-reported disability. WTX101 was associated with reduced disability and improved neurological status, and was well tolerated.

Example 7: Analysis of Patients with or without Cirrhosis

Mortality in Wilson disease is usually secondary to decompensated hepatic cirrhosis and liver failure; therefore, liver function is an important factor in determining appropriate treatment regimens. The outcome of patients with and without cirrhosis using in the patient pool of Example 1, supplemented with week 48 data generated in the 3-year extension phase of the initial trial, was analyzed. Example 1 was an open-label, single-arm, 24-week duration study using WTX101 15-60 mg/day initially, then response-guided individualized dosing (maximum administered, 120 mg/day). The extension phase is an open-label, single-arm, 3-year duration study using continued response-guided individualized dosing of WTX101 once daily.

For the analyses described in this example, patients were characterized as having cirrhosis based on medical history (biopsy or imaging) or based on estimates of AST to Platelet Ratio Index (APRI) (AST refers to aspartate aminotransferase). Summary statistics were calculated for Baseline demographics, $NCC_{corr}$ levels, ALT levels, MELD and modified Nazer scores, Albumin concentration, International normalized ratio (INR), Disability and neurological status using the unified Wilson's disease rating scale, and adverse events (AEs). Of 15 patients with cirrhosis, 13 completed the core study, all of which are continuing in extension study. Of 13 patients without cirrhosis, nine completed the core study, all of which are continuing in the extension study. Patient flow for the extension study is depicted in FIG. 12.

$NCC_{corr}$ at baseline was 3.6 μmol/L for patients with cirrhosis and 3.7 μmol/L for patients without cirrhosis. WTX101 reduced $NCC_{corr}$ levels by similar extents in patients with and without cirrhosis, from baseline to week 24, and improvements seen at week 24 were maintained to week 48. $NCC_{corr}$ levels are shown in FIG. 13.

In the core study, ALT elevations requiring dose adjustments occurred in five patients with cirrhosis and seven patients without cirrhosis. ALT elevations were associated with study withdrawal in three patients without cirrhosis. ALT elevations during the core study were not accompanied by increased bilirubin levels. From week 24 to week 48, no ALT elevations requiring dose adjustments occurred and ALT levels were stable regardless of cirrhosis status. ALT levels for patients with and without cirrhosis are shown in FIG. 14. The MELD score (liver disease severity; score range, 6-40) (FIG. 15) and modified Nazer score (prognostic index; score range, 0-20) (FIG. 16) were low at baseline and remained stable in the core study and to week 48.

Mean albumin concentration (FIG. 17A) and international normalized ratio (INR) (FIG. 17B) were stable in the core study and to week 48 in patients both with and without cirrhosis. Mean albumin concentration (FIG. 17A) and blood clotting time (FIG. 18) were within normal ranges at baseline. These remained stable in the core study and to week 48 in patients with and without cirrhosis. The UWDRS was used to assess patient-reported disability and clinician-rated neurological status. Improvements occurred during the core study and to week 48, regardless of cirrhosis status (FIGS. 19A and 19B). The tolerability profile of WTX101 was favourable and similar for patients with and without cirrhosis. During the core study, adverse events (AEs) occurred in 10 patients with cirrhosis and 12 without cirrhosis. The most common AEs were increased ALT and GGT levels (each in three patients with cirrhosis and five without cirrhosis), increased AST levels (four patients in each group), and tremor (four patients without cirrhosis). During the extension phase, fewer patients experienced AEs compared with the core study (nine patients with cirrhosis and six patients without cirrhosis). The most common AE was urinary tract infection (four patients with cirrhosis). Severe adverse events (SAEs) occurred in four patients with cirrhosis and six patients without cirrhosis during weeks 0-48. During the extension phase, two patients in the cirrhosis group experienced SAEs possibly related to WTX101. One patient had neutropenia and one patient had hepatolenticular degeneration.

In this analysis, improvements in control of copper levels with WTX101 treatment compared with baseline were maintained from week 24 to 48 weeks of WTX101 treatment in both patient groups. With WTX101, liver function was stable up to 48 weeks in patients with and without cirrhosis. The tolerability profile of WTX101 was favorable and was not influenced by the presence of cirrhosis. Therefore, WTX101 treatment continues to be effective and well tolerated, regardless of whether treated patients were with or without liver cirrhosis prior to treatment.

One of skill in the art would understand that the particular thresholds disclosed herein may vary somewhat depending on the particular conditions of testing and assay methods. Furthermore, one of skill in the art would understand that thresholds that are described as "greater than" or "less than," could, in certain embodiments, be "equal to or greater than" or "equal to or less than," respectively. Similarly, one of skill in the art would understand that thresholds that are described as "equal to or greater than" or "equal to or less than," could, in certain embodiments be "greater than" or "less than," respectively The foregoing detailed description has been given for clearness of understanding only and no unnecessary limitations should be understood there from as modifications will be obvious to those skilled in the art.

While the instant invention has been described in connection with specific embodiments thereof, it will be understood that it is capable of further modifications and this application is intended to cover any variations, uses, or adaptations of the invention following, in general, the principles of the disclosure, and including such departures from the present disclosure as come within known or customary practice within the art to which the invention pertains and as may be applied to the essential features hereinbefore set forth and as follows in the scope of the appended claims.

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestions that they constitute valid prior art of form part of the common general knowledge in any country in the world.

What is claimed:

1. A method of treating Wilson Disease in a patient in need thereof, comprising administering 15 mg of bis-choline tetrathiomolybdate once daily.

2. The method of claim 1, wherein the 15 mg of bis-choline tetrathiomolybdate is administered as a delayed-release dosage form.

3. The method of claim 2, wherein the dosage form is a tablet or capsule.

4. The method of claim 3, wherein the dosage form is a tablet.

5. The method of claim 1, wherein the patient exhibits a reduction in $NCC_{corrected}$ as measured after 24 weeks of administration as compared to the patient's $NCC_{corrected}$ as measured prior to administration.

6. The method of claim 5, wherein the patient exhibits at least a 20% reduction in $NCC_{corrected}$ as measured after 24 weeks of administration as compared to the patient's $NCC_{corrected}$ as measured prior to administration.

7. The method of claim 1, wherein the patient exhibits a reduction in $NCC_{corrected}$ as measured after 48 weeks of administration as compared to the patient's $NCC_{corrected}$ as measured prior to administration.

8. The method of claim 7, wherein the patient exhibits at least a 20% reduction in $NCC_{corrected}$ as measured after 48 weeks of administration as compared to the patient's $NCC_{corrected}$ as measured prior to administration.

9. A method of treating Wilson Disease in a patient in need thereof, comprising administering from 30 to 90 mg of bis-choline tetrathiomolybdate daily, wherein the patient has one or more of the following:
   a) an $NCC_{corrected}$ greater than 2.3 µm/L;
   b) alanine aminotransferase (ALT) level less than 80 IU/mL;
   c) hemoglobin of greater than 8 g/dL;
   d) platelets greater than 30,000/µL; and
   e) neutrophils greater than $10^3$/µL.

10. The method of claim 5, further comprising measuring at least one of said patient's:
    a) $NCC_{corrected}$ level;
    b) alanine aminotransferase (ALT) level;
    c) hemoglobin level;
    d) platelets level; and
    e) neutrophils level.

11. The method of claim 1, wherein bis-choline tetrathiomolybdate is administered in the fasted state.

12. The method of claim 4, wherein the tablet is an enterically coated tablet.

13. The method of claim 1, wherein the patient has cirrhosis.

14. The method of claim 1, wherein the patient does not have cirrhosis.

15. A method of treating Wilson Disease in a patient in need thereof, comprising administering 15 mg of bis-choline tetrathiomolybdate to the patient once every other day.

16. The method of claim 15, wherein the 15 mg of bis-choline tetrathiomolybdate is administered as a delayed-release dosage form.

17. The method of claim 16, wherein the dosage form is an enterically coated tablet.

18. The method of claim 15, wherein bis-choline tetrathiomolybdate is administered in the fasted state.

19. The method of claim 16, wherein the dosage form is a capsule.

20. The method of claim 15, wherein the patient has cirrhosis.

21. The method of claim 15, wherein the patient does not have cirrhosis.

* * * * *